(12) United States Patent
Leung

(10) Patent No.: US 11,952,413 B2
(45) Date of Patent: Apr. 9, 2024

(54) DIMERIZING AGENT REGULATED IMMUNORECEPTOR COMPLEXES COMPRISING INTERLEUKIN RECEPTOR SIGNALING DOMAINS

(71) Applicant: 2seventy bio, Inc., Cambridge, MA (US)

(72) Inventor: Wai-Hang Leung, Seattle, WA (US)

(73) Assignee: 2SEVENTY BIO, INC., Cambridge, MA (US)

( * ) Notice: Subject to any disclaimer, the term of this patent is extended or adjusted under 35 U.S.C. 154(b) by 244 days.

(21) Appl. No.: 16/771,402

(22) PCT Filed: Dec. 14, 2018

(86) PCT No.: PCT/US2018/065786
§ 371 (c)(1),
(2) Date: Jun. 10, 2020

(87) PCT Pub. No.: WO2019/118895
PCT Pub. Date: Jun. 20, 2019

(65) Prior Publication Data
US 2020/0392204 A1    Dec. 17, 2020

Related U.S. Application Data

(60) Provisional application No. 62/598,923, filed on Dec. 14, 2017.

(51) Int. Cl.
*C07K 14/54*     (2006.01)
*A61K 35/17*    (2015.01)
(Continued)

(52) U.S. Cl.
CPC .......... *C07K 14/7155* (2013.01); *A61K 35/17* (2013.01); *A61K 38/00* (2013.01);
(Continued)

(58) Field of Classification Search
None
See application file for complete search history.

(56) References Cited

U.S. PATENT DOCUMENTS 4,751,180 A    6/1988  Cousens et al.
4,935,233 A    6/1990  Bell et al.
(Continued)

FOREIGN PATENT DOCUMENTS

WO    WO 1999/036553 A2    7/1999
WO    WO 1999/041258 A1    8/1999
(Continued)

OTHER PUBLICATIONS

Leung et al., Abstract 1708_ Effective and reversible control of anti-tumor activity in vivo with a drug-regulated CAR T cell platform (DARIC), Cancer Res. 77(13 Suppl):Abst 1703, Jul. 1, 2017.*
(Continued)

*Primary Examiner* — Claire Kaufman
(74) *Attorney, Agent, or Firm* — McCarter & English, LLP; Marcie B. Clarke, Esq.; Dylan M. Blumenthal, Esq.

(57) ABSTRACT

The present disclosure provides improved compositions for adoptive T cell therapies for treating, preventing, or ameliorating at least one symptom of a cancer, infectious disease, autoimmune disease, inflammatory disease, and immunodeficiency, or condition associated therewith.

7 Claims, 5 Drawing Sheets

Specification includes a Sequence Listing.

(51) Int. Cl.

| | | |
|---|---|---|
| *A61K 38/00* | (2006.01) | |
| *A61P 35/00* | (2006.01) | |
| *C07K 14/705* | (2006.01) | |
| *C07K 14/715* | (2006.01) | |
| *C07K 14/73* | (2006.01) | |

(52) U.S. Cl.
CPC ........ *A61P 35/00* (2018.01); *C07K 14/70514* (2013.01); *C07K 14/70517* (2013.01); *C07K 14/70575* (2013.01); *C07K 2319/70* (2013.01)

(56) References Cited

U.S. PATENT DOCUMENTS

| | | | |
|---|---|---|---|
| 5,871,753 | A | 2/1999 | Crabtree et al. |
| 5,910,573 | A | 6/1999 | Pluckthun et al. |
| 6,291,158 | B1 | 9/2001 | Winter et al. |
| 6,291,161 | B1 | 9/2001 | Lerner et al. |
| 6,423,498 | B1 | 7/2002 | Markland et al. |
| 6,649,595 | B2 | 11/2003 | Clackson et al. |
| 6,692,736 | B2 | 2/2004 | Yu et al. |
| 6,972,193 | B1 | 12/2005 | Crabtree et al. |
| 9,587,020 | B2 | 3/2017 | Wu et al. |
| 10,196,444 | B2 | 2/2019 | Jarjour et al. |
| 10,428,142 | B2 | 10/2019 | Clackson et al. |
| 10,457,731 | B2 | 10/2019 | Jarjour et al. |
| 10,596,274 | B2* | 3/2020 | Frost .................... C12N 15/113 |
| 2003/0147869 | A1 | 8/2003 | Riley et al. |
| 2007/0065431 | A1 | 3/2007 | Coia et al. |
| 2013/0287752 | A1 | 10/2013 | Davila et al. |
| 2015/0266973 | A1 | 9/2015 | Jarjour et al. |
| 2016/0311901 | A1* | 10/2016 | Jarjour ..................... A61P 37/06 |
| 2018/0244797 | A1* | 8/2018 | Pulé ............... A61K 39/001135 |
| 2019/0112372 | A1 | 4/2019 | Jarjour et al. |
| 2019/0350974 | A1* | 11/2019 | Boyerinas ................ A61P 29/00 |
| 2020/0071399 | A1 | 3/2020 | Jarjour et al. |
| 2020/0071401 | A1 | 3/2020 | Jarjour et al. |
| 2021/0236546 | A1* | 8/2021 | Jarjour .................. C07K 14/705 |
| 2022/0025014 | A1* | 1/2022 | Jarjour ..................... A61P 35/02 |
| 2022/0031750 | A1* | 2/2022 | Jarjour ............... C07K 14/7151 |

FOREIGN PATENT DOCUMENTS

| | | |
|---|---|---|
| WO | WO 03/057171 A2 | 7/2003 |
| WO | WO 2006/072620 A1 | 7/2006 |
| WO | WO 2006/095164 A1 | 9/2006 |
| WO | WO 2007/098934 A1 | 9/2007 |
| WO | WO 2012/082841 A2 | 6/2012 |
| WO | WO 2014/127261 A1 | 8/2014 |
| WO | WO 2015/017214 A1 | 2/2015 |
| WO | WO 2016/100241 A2 | 6/2016 |
| WO | 2017/029512 A1 † | 2/2017 |
| WO | WO 2017/032777 A1 | 3/2017 |
| WO | WO 2017/123556 A1 | 7/2017 |
| WO | WO 2017/180993 A1 | 10/2017 |
| WO | WO 2017/205726 A1 | 11/2017 |
| WO | WO 2018/102795 A2 | 6/2018 |
| WO | WO 2019/118885 A1 | 6/2019 |
| WO | WO 2020/123933 A1 | 6/2020 |
| WO | WO 2020/123936 A1 | 6/2020 |
| WO | WO 2020/123938 A1 | 6/2020 |
| WO | WO 2020/123947 A1 | 6/2020 |

OTHER PUBLICATIONS

Wu et al., Remote control of therapeutic T cells through a small molecule-gated chimeric receptor, Science, 350(6258):aab4077-1-10, Oct. 16, 2015.*

Leung et al., Small Molecule-Regulated Antigen Recognition System for Inducible T Cell Targeting of Cancer Cells. Mol. Ther. 24(Suppl1):S110, Abstarct 277, May 2016.*

Tsutsumi et al., The structural basis for receptor recognition of human interleukin-18, Nat. Commun. DOI: 10.1038/ncomms6340, pp. 1-13, plus Supplementary Information pp. 1-11, Dec. 15, 2014.*

Stanton et al., Chemically induced proximity in biology and medicine, Science, 359:eaao5902, pp. 1-9, Mar. 9, 2018.*

UniProt Database, Q13478, IL18R1, Retrieved online: <URhttps://www.uniprot.org/uniprotkb/Q13478/entry>, retrieved on Jan. 20, 2023. 2023.*

UniProt Database, Q9Z2B1, IL18RA, Retrieved online: <URL:https://www.uniprot.org/uniprotkb/Q9Z2B1/entry>, retrieved on Jan. 20, 2023. 2023.*

Abate-Daga and Davila, "CAR models: next-generation CAR modifications for enhanced T-cell function." Oncolytics (2016); 3 (16014): 1-7.

Alder, M. et al., "Antibody responses of variable lymphocyte receptors in the lamprey", Nat Immunol. (2008); 9(3):319-327.

Banaszynski, L.A., et al., "Characterization of the FKBP Rapamycin FRB Ternary Complex." Journal of the American Chemical Society (2005); 127.13: 4715-4721.

Baral, et al., "Experimental therapy of African trypanosomiasis with a nanobody-conjugated human trypanolytic factor", Nat Med. (2006); 12(5): 580-584.

Barthelemy, PA. et al., "Comprehensive analysis of the factors contributing to the stability and solubility of autonomous human VH domains", J Biol Chem. (2008); 283(6):3639-3654.

Bayle, J.H., et al., "Rapamycin analogs with differential binding specificity permit orthogonal control of protein activity." Chemistry & Biology (2006); 13.1: 99-107.

Beavil, A. et al., "Alpha-helical coiled-coil stalks in the low-affinity receptor for IgE (Fc epsilon RII/CD23) and related C-type lectins", Proc Natl Acad Sci U S A. (1992); 89(2):753-757.

Belshaw, P.J., et al., "Controlling protein association and subcellular localization with a synthetic ligand that induces heterodimerization of proteins." Proc. Natl. Acad. Sci. USA (1996); 93: 4604-4607.

Beste, G. et al., "Small antibody-like proteins with prescribed ligand specificities derived from the lipocalin fold", Proc Natl Acad Sci U S A. (1999); 96(5):1898-903.

Binz, HK, et al., "Designing repeat proteins: well-expressed, soluble and stable proteins from combinatorial libraries of consensus ankyrin repeat proteins", J. Mol. Biol. (2003); 332(2): 489-503.

Binz, HK, et al., "Engineering novel binding proteins from nonimmunoglobulin domains", Nat. Biotechnol. (2005); 23(10): 1257-1268.

Bird, Robert E., et al. "Single-chain antigen-binding proteins." Science (1988); 242.4877: 423-427.

Brentjens, R. et al., "Safety and persistence of adoptively transferred autologous CD19-targeted T cells in patients with relapsed or chemotherapy refractory B-cell leukemias", Blood (2011); 118(18): 4817-4828.

Brentjens, R. et al., "CD19-Targeted T Cells Rapidly Induce Molecular Remissions in Adults with Chemotherapy-Refractory Acute Lymphoblastic Leukemia." Science Translational Medicine (2013); 5(177): 177ra38.

Brown, E. et al., "A mammalian protein targeted by G1-arresting rapamycin-receptor complex", Nature (1994); 369(6483): 756-758.

Capon, D. et al., "Designing CD4 immunoadhesins for AIDS therapy", Nature (1989); 337(6207): 525-531.

Carpenito, C. et. al., "Control of large, established tumor xenografts with genetically retargeted human T cells containing CD28 and CD137 domains", Proc Natl Acad Sci USA (2009); 106(9):3360-3365.

Challita, P. et al., "Multiple modifications in cis elements of the long terminal repeat of retroviral vectors lead to increased expression and decreased DNA methylation in embryonic carcinoma cells", J Virol. (1995) 69(2): 748-755.

Chaudhary, Vuay K., et al. "A rapid method of cloning functional variable-region antibody genes in *Escherichia coli* as single-chain immunotoxins." Proceedings of the National Academy of Sciences (1990); 87.3: 1066-1070 (and correction).

Cooper, Laurence JN, et al. "T-cell clones can be rendered specific for CD19: Toward the selective augmentation of the graft-versus-B-lineage leukemia effect." Blood (2003); 101.4: 1637-1644.

Cortez-Retamozo, V. et al., "Efficient cancer therapy with a nanobody-based conjugate", Cancer Res. (2004); 64(8):2853-2857.

(56) References Cited

OTHER PUBLICATIONS

Craik, D. et al., "Plant cyclotides: A unique family of cyclic and knotted proteins that defines the cyclic cystine knot structural motif", J. Mol. Biol. (1999); 294(5): 1327-1336.
Curran, K.J., et al., "Chimeric antigen receptors for T cell immunotherapy: current understanding and future directions." Journal of Gene Medicine (2012); 14(6): 405-415.
De Felipe et al., "Targeting of proteins derived from self-processing polyproteins containing multiple signal sequences." Traffic (2004); 5.8: 616-626.
Desjarlais et al., "Use of a zinc-finger consensus sequence framework and specificity rules to design specific DNA binding proteins." Proceedings of the National Academy of Sciences (1993); 90.6: 2256-2260.
Desjarlais et al., "Length-encoded multiplex binding site determination: application to zinc finger proteins," Proceedings of the National Academy of Sciences (1994); 91.23: 11099-11103.
Donnelly, M. et al., "The 'cleavage' activities of foot-and-mouth disease virus 2A site-directed mutants and naturally occurring '2A-like' sequences", J Gen Virol. (2001); 82 (Pt 5):1027-1041.
Dotti, et al., "Design and development of therapies using chimeric antigen receptor-expressing T cells." Immunol Rev. (2014); 257 (1): 107-126, 35 pages. First published: Dec. 13, 2013.
Duke et al., Sequence and structural elements that contribute to efficient encephalomyocarditis virus RNA translation, J Virol. Mar. 1992;66(3):1602-9.
Duong, C. et al., "Enhancing the specificity of T-cell cultures for adoptive immunotherapy of cancer", Immunotherapy (2011); 3(1): 33-48.
Extended European Search Report for European Application No. 14832043.5 dated Feb. 10, 2017, 11 pages.
Fegan, Adrian, et al. "Chemically controlled protein assembly: techniques and applications." Chemical Reviews (2010); 110.6: 3315-3336.
Ghahroudi, et al., "Selection and identification of single domain antibody fragments from camel heavy-chain antibodies", FEBS Lett. (1997); 414(3):521-526.
Grünberg, Raik, et al., "Building blocks for protein interaction devices." Nucleic Acids Research (2010); 38.8: 2645-2662.
Grupp, S.A. et al., "Chimeric antigen receptor-modified T cells for acute lymphoid leukemia", N Engl J Med. (2013); 368(16): 1509-1518.
Haas et al., "The Moloney murine leukemia virus repressor binding site represses expression in murine and human hematopoietic stem cells," J Virol. Sep. 2003; 77(17): 9439-9450.
Hackel, B. et al., "Picomolar affinity fibronectin domains engineered utilizing loop length diversity, recursive mutagenesis, and loop shuffling", J Mol Biol. (2008); 381(5):1238-1252.
Hamers-Casterman, C. et al., "Naturally occurring antibodies devoid of light chains", Nature (1993); 363(6428):446-448.
Herrin, B. et al., "Structure and specificity of lamprey monoclonal antibodies", Proc Natl Acad Sci U S A. (2008); 105(6):2040-2045.
Hu, S. et al., "Minibody: A novel engineered anti-carcinoembryonic antigen antibody fragment (single-chain Fv-CH3) which exhibits rapid, high-level targeting of xenografts" Cancer Res. (1996); 56(13):3055-3061.
Huang, C. et al., "Scorpion-toxin mimics of CD4 in complex with human immunodeficiency virus gp120 crystal structures, molecular mimicry, and neutralization breadth", Structure (2005); 13(5):755-768.
Hoet, R. et al., "Generation of high-affinity human antibodies by combining donor-derived and synthetic complementarity-determining-region diversity", Nat Biotechnol. (2005); 23(3):344-348.
Hsu, C. et al., "Primary human T lymphocytes engineered with a codon-optimized IL-15 gene resist cytokine withdrawal-induced apoptosis and persist long-term in the absence of exogenous cytokine", J Immunol. (2005); 175(11):7226-34.
Huez et al., "Two independent internal ribosome entry sites are involved in translation initiation of vascular endothelial growth factor mRNA," Mol Cell Biol. Nov. 1998;18(11):6178-90.

International Application No. PCT/US2014/047852, International Search Report and Written Opinion dated Nov. 21, 2014, 11 pages.
International Application No. PCT/US2014/047852, International Preliminary Report on Patentability dated Feb. 2, 2016, 8 pages.
International Search Report and Written Opinion dated Mar. 5, 2019, for International Application No. PCT/US2018/065786, 11 pages.
Irion, S. et al., "Identification and targeting of the ROSA26 locus in human embryonic stem cells", Nat Biotechnol. (2007); 25(12):1477-1482.
Jackson, et al., "The novel mechanism of initiation of picornavirus RNA translation", Trends Biochem Sci. (1990); 15(12): 477-483.
Jackson, et al., "Internal initiation of translation in eukaryotes: the picornavirus paradigm and beyond", RNA. (1995); 1(10): 985-1000.
Janeway, C. et al., "The Immune System in Health and Disease", Immunobiology (1999); 4th edition, Current Biology Publications p. 148, 149, and 172.
Jespers, L. et al., "Aggregation-resistant domain antibodies selected on phage by heat denaturation", Nat Biotechnol. (2004); 22(9):1161-1165.
June, C. et al., "T-cell therapy at the threshold", Nat Biotechnol. (2012); 30(7): 611-614.
Kalos, et al., "T Cells with Chimeric Antigen Receptors Have Potent Antitumor Effects and Can Establish Memory in Patients with Advanced Leukemia", Sci Transl Med. Aug. 10, 2011; 3(95): 95ra73. doi:10.1126/scitranslmed.3002842.
Kay, J.E. "Structure-function relationships in the FK506-binding protein (FKBP) family of peptidylprolyl cis-trans isomerases", Biochem J. (1996); 314 ( Pt 2):361-385.
Kim, Yang-Gyun, et al., "Hybrid restriction enzymes: zinc finger fusions to Fok I cleavage domain." Proceedings of the National Academy of Sciences (1996); 93.3: 1156-1160.
Kochenderfer, J et al., "Treating B-cell cancer with T cells expressing anti-CD19 chimeric antigen receptors", Nat Rev Clin Oncol. (2013); 10(5):267-276.
Kochenderfer, J. et al., "B-cell depletion and remissions of malignancy along with cytokine-associated toxicity in a clinical trial of anti-CD19 chimeric-antigen-receptor-transduced T cells", Blood (2012); 119(12):2709-2720.
Kowolik, C. et al., "CD28 costimulation provided through a CD19-specific chimeric antigenreceptor enhances in vivo persistence and antitumor efficacy of adoptively transferred T cells", Cancer Res. (2006); 66(22): 10995-11004.
Lee, S. et al., "Design of a binding scaffold based on variable lymphocyte receptors of jawless vertebrates by module engineering", Proc Natl Acad Sci U S A. (2012); 109(9):3299-3304.
Leung, Wai-Hang et al., "Small molecule-regulated antigen recognition system for inducible T cell targeting of cancer cells." Bluebird Bio, Cambridge, MA, United States. Molecular Therapy, (Apr. 2016) vol. 24, Supp. Suppl. 1, pp. S110, Abstract No. 277, 2 pages.
Liu, Qiang, et al. "Design of polydactyl zinc-finger proteins for unique addressing within complex genomes." Proceedings of the National Academy of Sciences (1997); 94.11: 5525-5530.
Main, E. et al., "Design of stable alpha-helical arrays from an idealized TPR motif", Structure (2003); 11(5):497-508.
Manzke, O. et al., "CD3X anti-nitrophenyl bispecific diabodies: universal immunotherapeutic tools for retargeting T cells to tumors", Int J Cancer. (1999); 82(5):700-708.
Maratea et al., "Deletion and fusion analysis of the phage phi X174 lysis gene E," Gene. 1985;40(1):39-46.
Martin, L. et al., "Rational design of a CD4 mimic that inhibits HIV-1 entry and exposes cryptic neutralization epitopes", Nat. Biotechnol. (2003); 21(1): 71-76.
Milone, M. et al., "Chimeric receptors containing CD137 signal transduction domains diate enhanced survival of T cells and increased antileukemic efficacy in vivo", Mol Ther. (2009); 17(8):1453-64.
Murphy et al., "Genetic construction, expression, and melanoma-selective cytotoxicity of a diphtheria toxin-related alpha-melanocyte-stimulating hormone fusion protein," Proc Natl Acad Sci USA. Nov. 1986;83(21):8258-62.
Nguyen, V. et al., "Heavy-chain antibodies in Camelidae; a case of evolutionary innovation", Immunogenetics (2002); 54(1): 39-47.

(56) References Cited

OTHER PUBLICATIONS

Nguyen, V. et al., "The specific variable domain of camel heavy-chain antibodies is encoded in the germline", J. Mol. Biol. (1998); 275(3): 413-418.
Nord, K. et al., "A combinatorial library of an alpha-helical bacterial receptor domain", Protein Eng. (1995); 8(6): 601-608.
Nord, K. et al., "Binding proteins selected from combinatorial libraries of an alpha-helical bacterial receptor domain", Nat. Biotechnol. (1997); 15(8): 772-777.
Nord, K. et al., "Recombinant human factor VIII-specific affinity ligands selected from phage-displayed combinatorial libraries of protein A", Eur J Biochem. (2001); 268(15):4269-4277.
Parker, M. "Antibody mimics based on human fibronectin type three domain engineered for thermostability and high-affinity binding to vascular endothelial growth factor receptor two", Protein Eng Des Sel. (2005); 18(9):435-444.
Patel, S. et al., "Impact of chimeric immune receptor extracellular protein domains on T cell function." Gene Ther (1999); 6(3): 412-419.
Pomerantz, et al., "Structure-based design of transcription factors." Science (1995); 267.5194: 93-96.
Pomerantz, et al., "Analysis of homeodomain function by structure-based design of a transcription factor," Proc Natl Acad Sci U S A. Oct. 10, 1995;92(21):9752-6.
Pule, M.A et al., "A chimeric T cell antigen receptor that augments cytokine release and supports clonal expansion of primary human T cells", Mol Ther. (2005); 12(5):933-941. Epub Jun. 23, 2005.
Quintarelli, C. "Co-expression of cytokine and suicide genes to enhance the activity and safety of tumor-specific cytotoxic T lymphocytes", Blood (2007); 110(8):2793-2802.
Restifo, N.P. et al., "Adoptive immunotherapy for cancer: harnessing the T cell response", Nat Rev Immunol. (2012); 12(4):269-281.
Richards, J. et al., "Engineered fibronectin type III domain with a RGDWXE sequence binds with enhanced affinity and specificity to human avb3 integrin", J. Mol. Biol. (2003); 326(5): 1475-1488.
Roux, K. et al., "Structural analysis of the nurse shark (new) antigen receptor (NAR): molecular convergence of NAR and unusual mammalian immunoglobulins", Proc Natl Acad Sci U S A. (1998); 95(20):11804-11809.
Ryan, M. et al., "Virus-encoded proteinases of the picornavirus super-group", J Gen Virol. (1997); 78 (Pt 4): 699-723.
Sato, A. et al., "Genes encoding putative natural killer cell C-type lectin receptors in teleostean fishes", Proc Natl Acad Sci U S A. (2003); 100(13): 7779-7784.
Schonfeld, D. et al., "An engineered lipocalin specific for CTLA-4 reveals a combining site with structural and conformational features similar to antibodies", Proc Natl Acad Sci U S A. (2009); 106(20):8198-8203.
Skerra, A. "Alternative binding proteins: anticalins—harnessing the structural plasticity of the lipocalin ligand pocket to engineer novel binding activities", FEBS J. (2008); 275(11):2677-2683.
Schlessinger, J., "Cell Signaling by Receptor Tyrosine Kinases." Cell (2000); 103: 211-225.
Spencer, David M., et al. "Controlling signal transduction with synthetic ligands." Science (1993); 262: 1019-1024.
Standaert, R. et al., "Molecular cloning and overexpression of the human FK506-binding protein FKBP", Nature (1990); 346(6285): 671-674.
Stephan, M. et al., "T cell-encoded CD80 and 4-1BBL induce auto- and transcostimulation, resulting in potent tumor rejection", Nat Med. (2007); 13(12): 1440-1449.
Stumpp, M et al., "Designing repeat proteins: modular leucine-rich repeat protein libraries based on the mammalian ribonuclease inhibitor family", J. Mol. Biol. (2003); 332(2): 471-487.
Szymczak, Andrea L., et al. "Correction of multi-gene deficiency in vivo using a single 'self-cleaving' 2A peptide-based retroviral vector." Nature Biotechnology (2004); 22.5: 589-594.
Tal, et al., "An NCR1-based chimeric receptor endows T-cells with multiple anti-tumor specificities." Oncotarget (2014); 5 (21): 10949-10958.
Till, B. et al., "CD20-specific adoptive immunotherapy for lymphoma using a chimeric antigen receptor with both CD28 and 4-1BB domains: pilot clinical trial results". Blood (2012); 119(17):3940-3950.
U.S. Appl. No. 14/608,098, Office Action dated Jun. 28, 2016, 25 pages.
Varadamsetty, G, et al., "Designed Armadillo repeat proteins: library generation,characterization and selection of peptide binders with high specificity", J. Mol. Biol. (2012); 424(1-2): 68-87.
Vincke, C. et al., "General strategy to humanize a camelid single-domain antibody and identification of a universal humanized nanobody scaffold", J Biol Chem. (2009); 284(5):3273-3284.
Vita, C. et al., "Scorpion toxins as natural scaffolds for protein engineering", Proc Natl Acad Sci U S A. (1995); 92(14):6404-6408.
Weisel, J. et al., "A model for fibrinogen: domains and sequence", Science (1985); 230(4732): 1388-1391.
White, I. et al., "Comparison of the glycosyl-phosphatidylinositol cleavage/attachment site between mammalian cells and parasitic protozoa", J Cell Sci. (2000); 113 (Pt 4):721-727.
Wilkie, S. et al., "Dual targeting of ErbB2 and MUC1 in breast cancer using chimeric antigen receptors engineered to provide complementary signaling", J. Clin. Immunol. (2012); 32(5): 1059-1070.
Zelensky and Gready. "The C-type lectin-like domain superfamily", FEBS J. (2005); 272(24):6179-6217.
Shi et al., Chimeric antigen receptor for adoptive immunotherapy of cancer: latest research and future prospects. Mol Cancer. Sep. 21, 2014;13:219.
Dinarello, Interleukin-18 and IL-18 binding protein. Front Immunol. Oct. 8, 2013;4:289, 11 pages.
Ogawa et al., Construction of unnatural heterodimeric receptors based on IL-2 and IL-6 receptor subunits. Biotechnol Prog. Nov.-Dec. 2013;29(6):1512-8.
Trinchieri, Interleukin-12 and the regulation of innate resistance and adaptive immunity. Nat Rev Immunol. Feb. 2003;3(2):133-46.

\* cited by examiner
† cited by third party

SEQUENCE LISTING

```
<160> NUMBER OF SEQ ID NOS: 43

<210> SEQ ID NO 1
<211> LENGTH: 333
<212> TYPE: PRT
<213> ORGANISM: Artificial Sequence
<220> FEATURE:
<223> OTHER INFORMATION: Synthesized IL-18R DARIC signaling component

<400> SEQUENCE: 1

Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
            20                  25                  30

Gly Leu Glu Glu Ala Ser Arg Leu Tyr Phe Gly Glu Arg Asn Val Lys
        35                  40                  45

Gly Met Phe Glu Val Leu Glu Pro Leu His Ala Met Met Glu Arg Gly
    50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
            100                 105                 110

Arg Ile Ser Lys Ala Ser Gly Met Ile Ile Ala Val Leu Ile Leu Val
```

-continued

```
            115                 120                 125
Ala Val Val Cys Leu Val Thr Val Cys Val Ile Tyr Arg Val Asp Leu
    130                 135                 140

Val Leu Phe Tyr Arg His Leu Thr Arg Arg Asp Glu Thr Leu Thr Asp
145                 150                 155                 160

Gly Lys Thr Tyr Asp Ala Phe Val Ser Tyr Leu Lys Glu Cys Arg Pro
                165                 170                 175

Glu Asn Gly Glu Glu His Thr Phe Ala Val Glu Ile Leu Pro Arg Val
            180                 185                 190

Leu Glu Lys His Phe Gly Tyr Lys Leu Cys Ile Phe Glu Arg Asp Val
        195                 200                 205

Val Pro Gly Gly Ala Val Val Asp Glu Ile His Ser Leu Ile Glu Lys
    210                 215                 220

Ser Arg Arg Leu Ile Ile Val Leu Ser Lys Ser Tyr Met Ser Asn Glu
225                 230                 235                 240

Val Arg Tyr Glu Leu Glu Ser Gly Leu His Glu Ala Leu Val Glu Arg
                245                 250                 255

Lys Ile Lys Ile Ile Leu Ile Glu Phe Thr Pro Val Thr Asp Phe Thr
            260                 265                 270

Phe Leu Pro Gln Ser Leu Lys Leu Leu Lys Ser His Arg Val Leu Lys
        275                 280                 285

Trp Lys Ala Asp Lys Ser Leu Ser Tyr Asn Ser Arg Phe Trp Lys Asn
    290                 295                 300

Leu Leu Tyr Leu Met Pro Ala Lys Thr Val Lys Pro Gly Arg Asp Glu
305                 310                 315                 320

Pro Glu Val Leu Pro Val Leu Ser Glu Ser Pro Arg Ser
                325                 330
```

<210> SEQ ID NO 2
<211> LENGTH: 354
<212> TYPE: PRT
<213> ORGANISM: Artificial Sequence
<220> FEATURE:
<223> OTHER INFORMATION: Synthesized IL-18R DARIC signaling component

<400> SEQUENCE: 2

```
Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
                20                  25                  30

Gly Leu Glu Glu Ala Ser Arg Leu Tyr Phe Gly Glu Arg Asn Val Lys
            35                  40                  45

Gly Met Phe Glu Val Leu Glu Pro Leu His Ala Met Met Glu Arg Gly
        50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
            100                 105                 110

Arg Ile Ser Lys Ala Ser Gly Met Ile Ile Ala Val Leu Ile Leu Val
        115                 120                 125

Ala Val Val Cys Leu Val Thr Val Cys Val Ile Tyr Arg Val Asp Leu
    130                 135                 140

Val Leu Phe Tyr Arg His Leu Thr Arg Arg Asp Glu Thr Leu Thr Asp
```

```
                145                 150                 155                 160
        Gly Lys Thr Tyr Asp Ala Phe Val Ser Tyr Leu Lys Glu Cys Arg Pro
                        165                 170                 175
        Glu Asn Gly Glu Glu His Thr Phe Ala Val Glu Ile Leu Pro Arg Val
                        180                 185                 190
        Leu Glu Lys His Phe Gly Tyr Lys Leu Cys Ile Phe Glu Arg Asp Val
                        195                 200                 205
        Val Pro Gly Gly Ala Val Val Asp Glu Ile His Ser Leu Ile Glu Lys
                        210                 215                 220
        Ser Arg Arg Leu Ile Ile Val Leu Ser Lys Ser Tyr Met Ser Asn Glu
        225                 230                 235                 240
        Val Arg Tyr Glu Leu Glu Ser Gly Leu His Glu Ala Leu Val Glu Arg
                        245                 250                 255
        Lys Ile Lys Ile Ile Leu Ile Glu Phe Thr Pro Val Thr Asp Phe Thr
                        260                 265                 270
        Phe Leu Pro Gln Ser Leu Lys Leu Leu Lys Ser His Arg Val Leu Lys
                        275                 280                 285
        Trp Lys Ala Asp Lys Ser Leu Ser Tyr Asn Ser Arg Phe Trp Lys Asn
                        290                 295                 300
        Leu Leu Tyr Leu Met Pro Ala Lys Thr Val Lys Pro Gly Arg Asp Glu
        305                 310                 315                 320
        Pro Glu Val Leu Pro Val Leu Ser Glu Ser Pro Arg Ser Gly Ser Gly
                        325                 330                 335
        Ala Thr Asn Phe Ser Leu Leu Lys Gln Ala Gly Asp Val Glu Glu Asn
                        340                 345                 350
        Pro Gly

<210> SEQ ID NO 3
<211> LENGTH: 373
<212> TYPE: PRT
<213> ORGANISM: Artificial Sequence
<220> FEATURE:
<223> OTHER INFORMATION: Synthesized IL-18R DARIC binding component

<400> SEQUENCE: 3

Met Glu Thr Asp Thr Leu Leu Leu Trp Val Leu Leu Leu Trp Val Pro
1               5                   10                  15
Gly Ser Thr Gly Gly Val Gln Val Glu Thr Ile Ser Pro Gly Asp Gly
                20                  25                  30
Arg Thr Phe Pro Lys Arg Gly Gln Thr Cys Val Val His Tyr Thr Gly
                35                  40                  45
Met Leu Glu Asp Gly Lys Lys Phe Asp Ser Ser Arg Asp Arg Asn Lys
        50                  55                  60
Pro Phe Lys Phe Met Leu Gly Lys Gln Glu Val Ile Arg Gly Trp Glu
65                  70                  75                  80
Glu Gly Val Ala Gln Met Ser Val Gly Gln Arg Ala Lys Leu Thr Ile
                85                  90                  95
Ser Pro Asp Tyr Ala Tyr Gly Ala Thr Gly His Pro Gly Ile Ile Pro
                100                 105                 110
Pro His Ala Thr Leu Val Phe Asp Val Glu Leu Leu Lys Leu Glu Gly
                115                 120                 125
Gly Arg Gly Val Val Leu Leu Tyr Ile Leu Leu Gly Thr Ile Gly Thr
                130                 135                 140
Leu Val Ala Val Leu Ala Ala Ser Ala Leu Leu Tyr Arg His Trp Ile
145                 150                 155                 160
```

```
Glu Ile Val Leu Leu Tyr Arg Thr Tyr Gln Ser Lys Asp Gln Thr Leu
                165                 170                 175

Gly Asp Lys Lys Asp Phe Asp Ala Phe Val Ser Tyr Ala Lys Trp Ser
            180                 185                 190

Ser Phe Pro Ser Glu Ala Thr Ser Ser Leu Ser Glu Glu His Leu Ala
        195                 200                 205

Leu Ser Leu Phe Pro Asp Val Leu Glu Asn Lys Tyr Gly Tyr Ser Leu
    210                 215                 220

Cys Leu Leu Glu Arg Asp Val Ala Pro Gly Gly Val Tyr Ala Glu Asp
225                 230                 235                 240

Ile Val Ser Ile Ile Lys Arg Ser Arg Arg Gly Ile Phe Ile Leu Ser
                245                 250                 255

Pro Asn Tyr Val Asn Gly Pro Ser Ile Phe Glu Leu Gln Ala Ala Val
            260                 265                 270

Asn Leu Ala Leu Asp Asp Gln Thr Leu Lys Leu Ile Leu Ile Lys Phe
        275                 280                 285

Cys Tyr Phe Gln Glu Pro Glu Ser Leu Pro His Leu Val Lys Lys Ala
    290                 295                 300

Leu Arg Val Leu Pro Thr Val Thr Trp Arg Gly Leu Lys Ser Val Pro
305                 310                 315                 320

Pro Asn Ser Arg Phe Trp Ala Lys Met Arg Tyr His Met Pro Val Lys
                325                 330                 335

Asn Ser Gln Gly Phe Thr Trp Asn Gln Leu Arg Ile Thr Ser Arg Ile
            340                 345                 350

Phe Gln Trp Lys Gly Leu Ser Arg Thr Glu Thr Thr Gly Arg Ser Ser
        355                 360                 365

Gln Pro Lys Glu Trp
    370

<210> SEQ ID NO 4
<211> LENGTH: 375
<212> TYPE: PRT
<213> ORGANISM: Artificial Sequence
<220> FEATURE:
<223> OTHER INFORMATION: Synthesized IL-18R DARIC binding component

<400> SEQUENCE: 4

Pro Ser Met Glu Thr Asp Thr Leu Leu Leu Trp Val Leu Leu Leu Trp
1               5                   10                  15

Val Pro Gly Ser Thr Gly Gly Val Gln Val Glu Thr Ile Ser Pro Gly
            20                  25                  30

Asp Gly Arg Thr Phe Pro Lys Arg Gly Gln Thr Cys Val Val His Tyr
        35                  40                  45

Thr Gly Met Leu Glu Asp Gly Lys Lys Phe Asp Ser Ser Arg Asp Arg
    50                  55                  60

Asn Lys Pro Phe Lys Phe Met Leu Gly Lys Gln Glu Val Ile Arg Gly
65                  70                  75                  80

Trp Glu Glu Gly Val Ala Gln Met Ser Val Gly Gln Arg Ala Lys Leu
                85                  90                  95

Thr Ile Ser Pro Asp Tyr Ala Tyr Gly Ala Thr Gly His Pro Gly Ile
            100                 105                 110

Ile Pro Pro His Ala Thr Leu Val Phe Asp Val Glu Leu Leu Lys Leu
        115                 120                 125

Glu Gly Gly Arg Gly Val Val Leu Leu Tyr Ile Leu Leu Gly Thr Ile
    130                 135                 140
```

```
Gly Thr Leu Val Ala Val Leu Ala Ala Ser Ala Leu Leu Tyr Arg His
145                 150                 155                 160

Trp Ile Glu Ile Val Leu Leu Tyr Arg Thr Tyr Gln Ser Lys Asp Gln
                165                 170                 175

Thr Leu Gly Asp Lys Lys Asp Phe Asp Ala Phe Val Ser Tyr Ala Lys
            180                 185                 190

Trp Ser Ser Phe Pro Ser Glu Ala Thr Ser Ser Leu Ser Glu Glu His
        195                 200                 205

Leu Ala Leu Ser Leu Phe Pro Asp Val Leu Glu Asn Lys Tyr Gly Tyr
210                 215                 220

Ser Leu Cys Leu Leu Glu Arg Asp Val Ala Pro Gly Gly Val Tyr Ala
225                 230                 235                 240

Glu Asp Ile Val Ser Ile Ile Lys Arg Ser Arg Arg Gly Ile Phe Ile
                245                 250                 255

Leu Ser Pro Asn Tyr Val Asn Gly Pro Ser Ile Phe Glu Leu Gln Ala
            260                 265                 270

Ala Val Asn Leu Ala Leu Asp Asp Gln Thr Leu Lys Leu Ile Leu Ile
        275                 280                 285

Lys Phe Cys Tyr Phe Gln Glu Pro Glu Ser Leu Pro His Leu Val Lys
290                 295                 300

Lys Ala Leu Arg Val Leu Pro Thr Val Thr Trp Arg Gly Leu Lys Ser
305                 310                 315                 320

Val Pro Pro Asn Ser Arg Phe Trp Ala Lys Met Arg Tyr His Met Pro
                325                 330                 335

Val Lys Asn Ser Gln Gly Phe Thr Trp Asn Gln Leu Arg Ile Thr Ser
            340                 345                 350

Arg Ile Phe Gln Trp Lys Gly Leu Ser Arg Thr Glu Thr Thr Gly Arg
        355                 360                 365

Ser Ser Gln Pro Lys Glu Trp
    370                 375

<210> SEQ ID NO 5
<211> LENGTH: 729
<212> TYPE: PRT
<213> ORGANISM: Artificial Sequence
<220> FEATURE:
<223> OTHER INFORMATION: Synthesized IL-18R DARIC polyprotein comprising
      an IL-18R DARIC binding component and signaling component
      separated by a viral P2A domain

<400> SEQUENCE: 5

Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
            20                  25                  30

Gly Leu Glu Glu Ala Ser Arg Leu Tyr Phe Gly Glu Arg Asn Val Lys
        35                  40                  45

Gly Met Phe Glu Val Leu Glu Pro Leu His Ala Met Met Glu Arg Gly
    50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
            100                 105                 110
```

-continued

```
Arg Ile Ser Lys Ala Ser Gly Met Ile Ile Ala Val Leu Ile Leu Val
            115                 120                 125
Ala Val Val Cys Leu Val Thr Val Cys Val Ile Tyr Arg Val Asp Leu
        130                 135                 140
Val Leu Phe Tyr Arg His Leu Thr Arg Arg Asp Glu Thr Leu Thr Asp
145                 150                 155                 160
Gly Lys Thr Tyr Asp Ala Phe Val Ser Tyr Leu Lys Glu Cys Arg Pro
                165                 170                 175
Glu Asn Gly Glu Glu His Thr Phe Ala Val Glu Ile Leu Pro Arg Val
            180                 185                 190
Leu Glu Lys His Phe Gly Tyr Lys Leu Cys Ile Phe Glu Arg Asp Val
        195                 200                 205
Val Pro Gly Gly Ala Val Val Asp Glu Ile His Ser Leu Ile Glu Lys
    210                 215                 220
Ser Arg Arg Leu Ile Ile Val Leu Ser Lys Ser Tyr Met Ser Asn Glu
225                 230                 235                 240
Val Arg Tyr Glu Leu Glu Ser Gly Leu His Glu Ala Leu Val Glu Arg
                245                 250                 255
Lys Ile Lys Ile Ile Leu Ile Glu Phe Thr Pro Val Thr Asp Phe Thr
            260                 265                 270
Phe Leu Pro Gln Ser Leu Lys Leu Leu Lys Ser His Arg Val Leu Lys
        275                 280                 285
Trp Lys Ala Asp Lys Ser Leu Ser Tyr Asn Ser Arg Phe Trp Lys Asn
    290                 295                 300
Leu Leu Tyr Leu Met Pro Ala Lys Thr Val Lys Pro Gly Arg Asp Glu
305                 310                 315                 320
Pro Glu Val Leu Pro Val Leu Ser Glu Ser Pro Arg Ser Gly Ser Gly
                325                 330                 335
Ala Thr Asn Phe Ser Leu Leu Lys Gln Ala Gly Asp Val Glu Glu Asn
            340                 345                 350
Pro Gly Pro Ser Met Glu Thr Asp Thr Leu Leu Leu Trp Val Leu Leu
        355                 360                 365
Leu Trp Val Pro Gly Ser Thr Gly Gly Val Gln Val Glu Thr Ile Ser
    370                 375                 380
Pro Gly Asp Gly Arg Thr Phe Pro Lys Arg Gly Gln Thr Cys Val Val
385                 390                 395                 400
His Tyr Thr Gly Met Leu Glu Asp Gly Lys Lys Phe Asp Ser Ser Arg
                405                 410                 415
Asp Arg Asn Lys Pro Phe Lys Phe Met Leu Gly Lys Gln Glu Val Ile
            420                 425                 430
Arg Gly Trp Glu Glu Gly Val Ala Gln Met Ser Val Gly Gln Arg Ala
        435                 440                 445
Lys Leu Thr Ile Ser Pro Asp Tyr Ala Tyr Gly Ala Thr Gly His Pro
    450                 455                 460
Gly Ile Ile Pro Pro His Ala Thr Leu Val Phe Asp Val Glu Leu Leu
465                 470                 475                 480
Lys Leu Glu Gly Gly Arg Gly Val Val Leu Leu Tyr Ile Leu Leu Gly
                485                 490                 495
Thr Ile Gly Thr Leu Val Ala Val Leu Ala Ala Ser Ala Leu Leu Tyr
            500                 505                 510
Arg His Trp Ile Glu Ile Val Leu Leu Tyr Arg Thr Tyr Gln Ser Lys
        515                 520                 525
Asp Gln Thr Leu Gly Asp Lys Lys Asp Phe Asp Ala Phe Val Ser Tyr
```

530                 535                 540
Ala Lys Trp Ser Ser Phe Pro Ser Glu Ala Thr Ser Ser Leu Ser Glu
545                 550                 555                 560

Glu His Leu Ala Leu Ser Leu Phe Pro Asp Val Leu Glu Asn Lys Tyr
                565                 570                 575

Gly Tyr Ser Leu Cys Leu Leu Glu Arg Asp Val Ala Pro Gly Gly Val
                580                 585                 590

Tyr Ala Glu Asp Ile Val Ser Ile Ile Lys Arg Ser Arg Arg Gly Ile
                595                 600                 605

Phe Ile Leu Ser Pro Asn Tyr Val Asn Gly Pro Ser Ile Phe Glu Leu
                610                 615                 620

Gln Ala Ala Val Asn Leu Ala Leu Asp Asp Gln Thr Leu Lys Leu Ile
625                 630                 635                 640

Leu Ile Lys Phe Cys Tyr Phe Gln Glu Pro Glu Ser Leu Pro His Leu
                645                 650                 655

Val Lys Lys Ala Leu Arg Val Leu Pro Thr Val Thr Trp Arg Gly Leu
                660                 665                 670

Lys Ser Val Pro Pro Asn Ser Arg Phe Trp Ala Lys Met Arg Tyr His
                675                 680                 685

Met Pro Val Lys Asn Ser Gln Gly Phe Thr Trp Asn Gln Leu Arg Ile
                690                 695                 700

Thr Ser Arg Ile Phe Gln Trp Lys Gly Leu Ser Arg Thr Glu Thr Thr
705                 710                 715                 720

Gly Arg Ser Ser Gln Pro Lys Glu Trp
                725

<210> SEQ ID NO 6
<211> LENGTH: 989
<212> TYPE: PRT
<213> ORGANISM: Artificial Sequence
<220> FEATURE:
<223> OTHER INFORMATION: Synthesized IL-18R DARIC -GFP polyprotein
      comprising an IL-18R DARIC binding component, signaling component,
      and GFP, each separated by a viral P2A domain

<400> SEQUENCE: 6

Met Ala Leu Pro Val Thr Ala Leu Leu Leu Pro Leu Ala Leu Leu Leu
1               5                   10                  15

His Ala Ala Arg Pro Gly Ser Ile Leu Trp His Glu Met Trp His Glu
                20                  25                  30

Gly Leu Glu Glu Ala Ser Arg Leu Tyr Phe Gly Glu Arg Asn Val Lys
                35                  40                  45

Gly Met Phe Glu Val Leu Glu Pro Leu His Ala Met Met Glu Arg Gly
    50                  55                  60

Pro Gln Thr Leu Lys Glu Thr Ser Phe Asn Gln Ala Tyr Gly Arg Asp
65                  70                  75                  80

Leu Met Glu Ala Gln Glu Trp Cys Arg Lys Tyr Met Lys Ser Gly Asn
                85                  90                  95

Val Lys Asp Leu Leu Gln Ala Trp Asp Leu Tyr Tyr His Val Phe Arg
                100                 105                 110

Arg Ile Ser Lys Ala Ser Gly Met Ile Ile Ala Val Leu Ile Leu Val
                115                 120                 125

Ala Val Val Cys Leu Val Thr Val Cys Val Ile Tyr Arg Val Asp Leu
                130                 135                 140

Val Leu Phe Tyr Arg His Leu Thr Arg Arg Asp Glu Thr Leu Thr Asp
145                 150                 155                 160

```
Gly Lys Thr Tyr Asp Ala Phe Val Ser Tyr Leu Lys Glu Cys Arg Pro
                165                 170                 175

Glu Asn Gly Glu Glu His Thr Phe Ala Val Glu Ile Leu Pro Arg Val
            180                 185                 190

Leu Glu Lys His Phe Gly Tyr Lys Leu Cys Ile Phe Glu Arg Asp Val
        195                 200                 205

Val Pro Gly Gly Ala Val Val Asp Glu Ile His Ser Leu Ile Glu Lys
    210                 215                 220

Ser Arg Arg Leu Ile Ile Val Leu Ser Lys Ser Tyr Met Ser Asn Glu
225                 230                 235                 240

Val Arg Tyr Glu Leu Glu Ser Gly Leu His Glu Ala Leu Val Glu Arg
                245                 250                 255

Lys Ile Lys Ile Ile Leu Ile Glu Phe Thr Pro Val Thr Asp Phe Thr
            260                 265                 270

Phe Leu Pro Gln Ser Leu Lys Leu Leu Lys Ser His Arg Val Leu Lys
        275                 280                 285

Trp Lys Ala Asp Lys Ser Leu Ser Tyr Asn Ser Arg Phe Trp Lys Asn
    290                 295                 300

Leu Leu Tyr Leu Met Pro Ala Lys Thr Val Lys Pro Gly Arg Asp Glu
305                 310                 315                 320

Pro Glu Val Leu Pro Val Leu Ser Glu Ser Pro Arg Ser Gly Ser Gly
                325                 330                 335

Ala Thr Asn Phe Ser Leu Leu Lys Gln Ala Gly Asp Val Glu Glu Asn
            340                 345                 350

Pro Gly Pro Ser Met Glu Thr Asp Thr Leu Leu Leu Trp Val Leu Leu
        355                 360                 365

Leu Trp Val Pro Gly Ser Thr Gly Gly Val Gln Val Glu Thr Ile Ser
    370                 375                 380

Pro Gly Asp Gly Arg Thr Phe Pro Lys Arg Gly Gln Thr Cys Val Val
385                 390                 395                 400

His Tyr Thr Gly Met Leu Glu Asp Gly Lys Lys Phe Asp Ser Ser Arg
                405                 410                 415

Asp Arg Asn Lys Pro Phe Lys Phe Met Leu Gly Lys Gln Glu Val Ile
            420                 425                 430

Arg Gly Trp Glu Glu Gly Val Ala Gln Met Ser Val Gly Gln Arg Ala
        435                 440                 445

Lys Leu Thr Ile Ser Pro Asp Tyr Ala Tyr Gly Ala Thr Gly His Pro
    450                 455                 460

Gly Ile Ile Pro Pro His Ala Thr Leu Val Phe Asp Val Glu Leu Leu
465                 470                 475                 480

Lys Leu Glu Gly Gly Arg Gly Val Val Leu Leu Tyr Ile Leu Leu Gly
                485                 490                 495

Thr Ile Gly Thr Leu Val Ala Val Leu Ala Ala Ser Ala Leu Leu Tyr
            500                 505                 510

Arg His Trp Ile Glu Ile Val Leu Leu Tyr Arg Thr Tyr Gln Ser Lys
        515                 520                 525

Asp Gln Thr Leu Gly Asp Lys Lys Asp Phe Asp Ala Phe Val Ser Tyr
    530                 535                 540

Ala Lys Trp Ser Ser Phe Pro Ser Glu Ala Thr Ser Ser Leu Ser Glu
545                 550                 555                 560

Glu His Leu Ala Leu Ser Leu Phe Pro Asp Val Leu Glu Asn Lys Tyr
                565                 570                 575
```

```
Gly Tyr Ser Leu Cys Leu Leu Glu Arg Asp Val Ala Pro Gly Val
            580                 585                 590

Tyr Ala Glu Asp Ile Val Ser Ile Ile Lys Arg Ser Arg Gly Ile
        595                 600                 605

Phe Ile Leu Ser Pro Asn Tyr Val Asn Gly Pro Ser Ile Phe Glu Leu
        610                 615                 620

Gln Ala Ala Val Asn Leu Ala Leu Asp Asp Gln Thr Leu Lys Leu Ile
625                 630                 635                 640

Leu Ile Lys Phe Cys Tyr Phe Gln Glu Pro Glu Ser Leu Pro His Leu
                645                 650                 655

Val Lys Lys Ala Leu Arg Val Leu Pro Thr Val Thr Trp Arg Gly Leu
            660                 665                 670

Lys Ser Val Pro Pro Asn Ser Arg Phe Trp Ala Lys Met Arg Tyr His
        675                 680                 685

Met Pro Val Lys Asn Ser Gln Gly Phe Thr Trp Asn Gln Leu Arg Ile
        690                 695                 700

Thr Ser Arg Ile Phe Gln Trp Lys Gly Leu Ser Arg Thr Glu Thr Thr
705                 710                 715                 720

Gly Arg Ser Ser Gln Pro Lys Glu Trp Ala Thr Asn Phe Ser Leu Leu
                725                 730                 735

Lys Gln Ala Gly Asp Val Glu Glu Asn Pro Gly Pro Ser Gly Met Val
            740                 745                 750

Ser Lys Gly Glu Glu Leu Phe Thr Gly Val Val Pro Ile Leu Val Glu
        755                 760                 765

Leu Asp Gly Asp Val Asn Gly His Lys Phe Ser Val Ser Gly Glu Gly
        770                 775                 780

Glu Gly Asp Ala Thr Tyr Gly Lys Leu Thr Leu Lys Phe Ile Cys Thr
785                 790                 795                 800

Thr Gly Lys Leu Pro Val Pro Trp Pro Thr Leu Val Thr Thr Leu Thr
                805                 810                 815

Tyr Gly Val Gln Cys Phe Ser Arg Tyr Pro Asp His Met Lys Gln His
            820                 825                 830

Asp Phe Phe Lys Ser Ala Met Pro Glu Gly Tyr Val Gln Glu Arg Thr
        835                 840                 845

Ile Phe Phe Lys Asp Asp Gly Asn Tyr Lys Thr Arg Ala Glu Val Lys
        850                 855                 860

Phe Glu Gly Asp Thr Leu Val Asn Arg Ile Glu Leu Lys Gly Ile Asp
865                 870                 875                 880

Phe Lys Glu Asp Gly Asn Ile Leu Gly His Lys Leu Glu Tyr Asn Tyr
                885                 890                 895

Asn Ser His Asn Val Tyr Ile Met Ala Asp Lys Gln Lys Asn Gly Ile
            900                 905                 910

Lys Val Asn Phe Lys Ile Arg His Asn Ile Glu Asp Gly Ser Val Gln
        915                 920                 925

Leu Ala Asp His Tyr Gln Gln Asn Thr Pro Ile Gly Asp Gly Pro Val
        930                 935                 940

Leu Leu Pro Asp Asn His Tyr Leu Ser Thr Gln Ser Ala Leu Ser Lys
945                 950                 955                 960

Asp Pro Asn Glu Lys Arg Asp His Met Val Leu Leu Glu Phe Val Thr
                965                 970                 975

Ala Ala Gly Ile Thr Leu Gly Met Asp Glu Leu Tyr Lys
            980                 985
```

```
<210> SEQ ID NO 7
<211> LENGTH: 3
<212> TYPE: PRT
<213> ORGANISM: Artificial Sequence
<220> FEATURE:
<223> OTHER INFORMATION: Exemplary linker sequence

<400> SEQUENCE: 7

Gly Gly Gly
1

<210> SEQ ID NO 8
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 8

Asp Gly Gly Gly Ser
1               5

<210> SEQ ID NO 9
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 9

Thr Gly Glu Lys Pro
1               5

<210> SEQ ID NO 10
<211> LENGTH: 4
<212> TYPE: PRT
<213> ORGANISM: Artificial Sequence
<220> FEATURE:
<223> OTHER INFORMATION: Exemplary linker sequence

<400> SEQUENCE: 10

Gly Gly Arg Arg
1

<210> SEQ ID NO 11
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 11

Gly Gly Gly Gly Ser
1               5

<210> SEQ ID NO 12
<211> LENGTH: 14
<212> TYPE: PRT
<213> ORGANISM: Artificial Sequence
<220> FEATURE:
<223> OTHER INFORMATION: Exemplary linker sequence

<400> SEQUENCE: 12

Glu Gly Lys Ser Ser Gly Ser Gly Ser Glu Ser Lys Val Asp
1               5                   10

<210> SEQ ID NO 13
```

```
<211> LENGTH: 18
<212> TYPE: PRT
<213> ORGANISM: Artificial Sequence
<220> FEATURE:
<223> OTHER INFORMATION: Exemplary linker sequence

<400> SEQUENCE: 13

Lys Glu Ser Gly Ser Val Ser Ser Glu Gln Leu Ala Gln Phe Arg Ser
1               5                   10                  15

Leu Asp

<210> SEQ ID NO 14
<211> LENGTH: 8
<212> TYPE: PRT
<213> ORGANISM: Artificial Sequence
<220> FEATURE:
<223> OTHER INFORMATION: Exemplary linker sequence

<400> SEQUENCE: 14

Gly Gly Arg Arg Gly Gly Gly Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Exemplary linker sequence

<400> SEQUENCE: 15

Leu Arg Gln Arg Asp Gly Glu Arg Pro
1               5

<210> SEQ ID NO 16
<211> LENGTH: 12
<212> TYPE: PRT
<213> ORGANISM: Artificial Sequence
<220> FEATURE:
<223> OTHER INFORMATION: Exemplary linker sequence

<400> SEQUENCE: 16

Leu Arg Gln Lys Asp Gly Gly Gly Ser Glu Arg Pro
1               5                   10

<210> SEQ ID NO 17
<211> LENGTH: 16
<212> TYPE: PRT
<213> ORGANISM: Artificial Sequence
<220> FEATURE:
<223> OTHER INFORMATION: Exemplary linker sequence

<400> SEQUENCE: 17

Leu Arg Gln Lys Asp Gly Gly Gly Ser Gly Gly Gly Ser Glu Arg Pro
1               5                   10                  15

<210> SEQ ID NO 18
<211> LENGTH: 7
<212> TYPE: PRT
<213> ORGANISM: Artificial Sequence
<220> FEATURE:
<223> OTHER INFORMATION: Cleavage sequence by TEV protease
<220> FEATURE:
<221> NAME/KEY: misc_feature
<222> LOCATION: (2)..(3)
<223> OTHER INFORMATION: Xaa is any amino acid
<220> FEATURE:
<221> NAME/KEY: misc_feature
<222> LOCATION: (5)..(5)
```

```
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa = Gly or Ser

<400> SEQUENCE: 18

Glu Xaa Xaa Tyr Xaa Gln Xaa
1               5

<210> SEQ ID NO 19
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 19

Glu Asn Leu Tyr Phe Gln Gly
1               5

<210> SEQ ID NO 20
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 20

Glu Asn Leu Tyr Phe Gln Ser
1               5

<210> SEQ ID NO 21
<211> LENGTH: 22
<212> TYPE: PRT
<213> ORGANISM: Artificial Sequence
<220> FEATURE:
<223> OTHER INFORMATION: Self-cleaving polypeptide comprising 2A site

<400> SEQUENCE: 21

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 22
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 22

Ala Thr Asn Phe Ser Leu Leu Lys Gln Ala Gly Asp Val Glu Glu Asn
1               5                   10                  15

Pro Gly Pro

<210> SEQ ID NO 23
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 23

Leu Leu Lys Gln Ala Gly Asp Val Glu Glu Asn Pro Gly Pro
```

```
1               5                   10
```

<210> SEQ ID NO 24
<211> LENGTH: 21
<212> TYPE: PRT
<213> ORGANISM: Artificial Sequence
<220> FEATURE:
<223> OTHER INFORMATION: Self-cleaving polypeptide comprising 2A site

<400> SEQUENCE: 24

```
Gly Ser Gly Glu Gly Arg Gly Ser Leu Leu Thr Cys Gly Asp Val Glu
1               5                   10                  15

Glu Asn Pro Gly Pro
            20
```

<210> SEQ ID NO 25
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 25

```
Glu Gly Arg Gly Ser Leu Leu Thr Cys Gly Asp Val Glu Glu Asn Pro
1               5                   10                  15

Gly Pro
```

<210> SEQ ID NO 26
<211> LENGTH: 13
<212> TYPE: PRT
<213> ORGANISM: Artificial Sequence
<220> FEATURE:
<223> OTHER INFORMATION: Self-cleaving polypeptide comprising 2A site

<400> SEQUENCE: 26

```
Leu Leu Thr Cys Gly Asp Val Glu Glu Asn Pro Gly Pro
1               5                   10
```

<210> SEQ ID NO 27
<211> LENGTH: 23
<212> TYPE: PRT
<213> ORGANISM: Artificial Sequence
<220> FEATURE:
<223> OTHER INFORMATION: Self-cleaving polypeptide comprising 2A site

<400> SEQUENCE: 27

```
Gly Ser Gly Gln Cys Thr Asn Tyr Ala Leu Leu Lys Leu Ala Gly Asp
1               5                   10                  15

Val Glu Ser Asn Pro Gly Pro
            20
```

<210> SEQ ID NO 28
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 28

```
Gln Cys Thr Asn Tyr Ala Leu Leu Lys Leu Ala Gly Asp Val Glu Ser
1               5                   10                  15

Asn Pro Gly Pro
            20
```

```
<210> SEQ ID NO 29
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 29

Leu Leu Lys Leu Ala Gly Asp Val Glu Ser Asn Pro Gly Pro
1               5                   10

<210> SEQ ID NO 30
<211> LENGTH: 25
<212> TYPE: PRT
<213> ORGANISM: Artificial Sequence
<220> FEATURE:
<223> OTHER INFORMATION: Self-cleaving polypeptide comprising 2A site

<400> SEQUENCE: 30

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 31
<211> LENGTH: 22
<212> TYPE: PRT
<213> ORGANISM: Artificial Sequence
<220> FEATURE:
<223> OTHER INFORMATION: Self-cleaving polypeptide comprising 2A site

<400> SEQUENCE: 31

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 32
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 32

Leu Leu Lys Leu Ala Gly Asp Val Glu Ser Asn Pro Gly Pro
1               5                   10

<210> SEQ ID NO 33
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 33

Leu Leu Asn Phe Asp Leu Leu Lys Leu Ala Gly Asp Val Glu Ser Asn
1               5                   10                  15

Pro Gly Pro

<210> SEQ ID NO 34
<211> LENGTH: 19
<212> TYPE: PRT
<213> ORGANISM: Artificial Sequence
<220> FEATURE:
<223> OTHER INFORMATION: Self-cleaving polypeptide comprising 2A site
```

```
<400> SEQUENCE: 34

Thr Leu Asn Phe Asp Leu Leu Lys Leu Ala Gly Asp Val Glu Ser Asn
1               5                   10                  15

Pro Gly Pro

<210> SEQ ID NO 35
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 35

Leu Leu Lys Leu Ala Gly Asp Val Glu Ser Asn Pro Gly Pro
1               5                   10

<210> SEQ ID NO 36
<211> LENGTH: 17
<212> TYPE: PRT
<213> ORGANISM: Artificial Sequence
<220> FEATURE:
<223> OTHER INFORMATION: Self-cleaving polypeptide comprising 2A site

<400> SEQUENCE: 36

Asn Phe Asp Leu Leu Lys Leu Ala Gly Asp Val Glu Ser Asn Pro Gly
1               5                   10                  15

Pro

<210> SEQ ID NO 37
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 37

Gln Leu Leu Asn Phe Asp Leu Leu Lys Leu Ala Gly Asp Val Glu Ser
1               5                   10                  15

Asn Pro Gly Pro
            20

<210> SEQ ID NO 38
<211> LENGTH: 24
<212> TYPE: PRT
<213> ORGANISM: Artificial Sequence
<220> FEATURE:
<223> OTHER INFORMATION: Self-cleaving polypeptide comprising 2A site

<400> SEQUENCE: 38

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 39
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 39

Val Thr Glu Leu Leu Tyr Arg Met Lys Arg Ala Glu Thr Tyr Cys Pro
```

```
1               5                   10                  15
Arg Pro Leu Leu Ala Ile His Pro Thr Glu Ala Arg His Lys Gln Lys
            20                  25                  30

Ile Val Ala Pro Val Lys Gln Thr
            35                  40

<210> SEQ ID NO 40
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 40

Leu Asn Phe Asp Leu Leu Lys Leu Ala Gly Asp Val Glu Ser Asn Pro
1               5                   10                  15

Gly Pro

<210> SEQ ID NO 41
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 41

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
            20                  25                  30

Asp Val Glu Ser Asn Pro Gly Pro
            35                  40

<210> SEQ ID NO 42
<211> LENGTH: 33
<212> TYPE: PRT
<213> ORGANISM: Artificial Sequence
<220> FEATURE:
<223> OTHER INFORMATION: Self-cleaving polypeptide comprising 2A site

<400> SEQUENCE: 42

Glu Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
            20                  25                  30

Pro

<210> SEQ ID NO 43
<211> LENGTH: 10
<212> TYPE: DNA
<213> ORGANISM: Artificial Sequence
<220> FEATURE:
<223> OTHER INFORMATION: Consensus Kozak sequence

<400> SEQUENCE: 43 gccrccatgg                                                          10
```

DIMERIZING AGENT REGULATED IMMUNORECEPTOR COMPLEXES COMPRISING INTERLEUKIN RECEPTOR SIGNALING DOMAINS

CROSS REFERENCE TO RELATED APPLICATIONS

This application is a National Stage application under 35 U.S.C. § 371 of International Application No. PCT/US2018/065786, filed Dec. 14, 2018, which claims the benefit under 35 U.S.C. § 119(e) of U.S. Provisional Application No. 62/598,923, filed Dec. 14, 2017, which is incorporated by reference herein in its entirety.

STATEMENT REGARDING SEQUENCE LISTING

The Sequence Listing associated with this application is provided in text format in lieu of a paper copy and is hereby incorporated by reference into the specification. The name of the text file containing the Sequence Listing is BLBD_092_01WO_ST25.txt. The text file is 38,514 bytes, was created on Dec. 14, 2018, and is being submitted electronically via EFS-Web, concurrent with the filing of the specification.

BACKGROUND

Technical Field

The present disclosure relates to improved adoptive cell therapies. More particularly, the disclosure relates to improved chemically regulated signaling molecules, cells, and methods of using the same for modulating spatial and temporal control of cellular signal initiation and downstream responses during adoptive immunotherapy.

Description of the Related Art

The global burden of cancer doubled between 1975 and 2000. Cancer is the second leading cause of morbidity and mortality worldwide, with approximately 14.1 million new cases and 8.2 million cancer related deaths in 2012. The most common cancers are breast cancer, lung and bronchus cancer, prostate cancer, colon and rectum cancer, bladder cancer, melanoma of the skin, non-Hodgkin lymphoma, thyroid cancer, kidney and renal pelvis cancer, endometrial cancer, leukemia, and pancreatic cancer. The number of new cancer cases is projected to rise to 22 million within the next two decades.

Adoptive cellular therapy is emerging as a powerful paradigm for delivering complex biological signals to treat cancer. In contrast to small molecule and biologic drug compositions, adoptive cell therapies have the potential to execute unique therapeutic tasks owing to their myriad sensory and response programs and increasingly defined mechanisms of genetic control. To achieve such therapeutic value, cells need to be outfitted with machinery for sensing and integrating chemical and/or biological information associated with local physiological environments.

BRIEF SUMMARY

The present disclosure generally relates, in part, to IL DARIC compositions, polynucleotides, polypeptides, and methods of making and using the same.

In various embodiments, the present disclosure contemplates, in part, a fusion polypeptide comprising: a first polypeptide comprising a first multimerization domain, a first transmembrane domain, and a first immune receptor intracellular signaling domain; a polypeptide cleavage signal; and a second polypeptide comprising a second multimerization domain, a second transmembrane domain; and a second immune receptor intracellular signaling domain.

In certain embodiments, the first multimerization domain and the second multimerization domain are the same.

In some embodiments, the first multimerization domain and the second multimerization domain are different.

In some embodiments, the first multimerization domain and the second multimerization domain associate with a bridging factor selected from the group consisting of: rapamycin or a rapalog thereof, coumermycin or a derivative thereof, gibberellin or a derivative thereof, abscisic acid (ABA) or a derivative thereof, methotrexate or a derivative thereof, cyclosporin A or a derivative thereof, FK506/cyclosporin A (FKCsA) or a derivative thereof, and trimethoprim (Tmp)-synthetic ligand for FK506 binding protein (FKBP) (SLF) or a derivative thereof.

In particular embodiments, the first multimerization domain and the second multimerization domain are a pair selected from the group consisting of: FKBP and FKBP12-rapamycin binding (FRB) or variants thereof; FKBP and calcineurin or variants thereof; FKBP and cyclophilin or variants thereof; FKBP and bacterial dihydrofolate reductase (DHFR) or variants thereof; calcineurin and cyclophilin or variants thereof; PYR1-like 1 (PYL1) and abscisic acid insensitive 1 (ABI1) or variants thereof; and GIB1 and GAI or variants thereof.

In various embodiments, the first multimerization domain comprises a FKBP polypeptide or variant thereof, and the second multimerization domain comprises a FRB polypeptide or variant thereof.

In certain embodiments, the first multimerization domain comprises a FRB polypeptide or variant thereof, and the second multimerization domain comprises a FKBP polypeptide or variant thereof.

In particular embodiments, the first and second multimerization domains are selected from FRB T2098L and FKBP12; and the bridging factor is AP21967.

In particular embodiments, the bridging factor is selected from the group consisting of: AP21967, sirolimus, everolimus, novolimus, pimecrolimus, ridaforolimus, tacrolimus, temsirolimus, umirolimus, and zotarolimus.

In some embodiments, the first transmembrane domain and the second transmembrane domain are independently selected from the group consisting of: a CD4 transmembrane domain, a CD8α transmembrane domain, an amnionless (AMN) transmembrane domain, a CD28 transmembrane domain, a CD154 transmembrane domain, and a CD71 transmembrane domain.

In certain embodiments, the first transmembrane domain and the second transmembrane domain are independently selected from the group consisting of: a CD4 transmembrane domain and a CD8α transmembrane domain.

In some embodiments, the first transmembrane domain and the second transmembrane domain are the same.

In various embodiments, the first transmembrane domain and the second transmembrane domain are different.

In certain embodiments, the first immune receptor intracellular signaling domain and the second immune receptor intracellular signaling domain are isolated from a cytokine receptor, an interleukin receptor, a pattern recognition receptor, or a toll-like receptor.

In particular embodiments, the first immune receptor intracellular signaling domain comprises an IL-12Rβ2 intracellular signaling domain and the second immune receptor intracellular signaling domain comprises an IL-12Rβ1 intracellular signaling domain.

In particular embodiments, the first immune receptor intracellular signaling domain comprises an IL-12Rβ1 intracellular signaling domain and the second immune receptor intracellular signaling domain comprises an IL-12Rβ2 intracellular signaling domain.

In some embodiments, the first immune receptor intracellular signaling domain comprises an IL-7Rα intracellular signaling domain and the second immune receptor intracellular signaling domain comprises an IL-2Rγ intracellular signaling domain.

In certain embodiments, the first immune receptor intracellular signaling domain comprises an IL-2Rγ intracellular signaling domain and the second immune receptor intracellular signaling domain comprises an IL-7Rα intracellular signaling domain.

In various embodiments, the first immune receptor intracellular signaling domain comprises an IL-2Rβ intracellular signaling domain and the second immune receptor intracellular signaling domain comprises an IL-2Rγ intracellular signaling domain.

In particular embodiments, the first immune receptor intracellular signaling domain comprises an IL-2Rγ intracellular signaling domain and the second immune receptor intracellular signaling domain comprises an IL-2Rβ intracellular signaling domain.

In some embodiments, the first immune receptor intracellular signaling domain comprises an IL-21R intracellular signaling domain and the second immune receptor intracellular signaling domain comprises an IL-2Rγ intracellular signaling domain.

In certain embodiments, the first immune receptor intracellular signaling domain comprises an IL-2Rγ intracellular signaling domain and the second immune receptor intracellular signaling domain comprises an IL-21R intracellular signaling domain.

In particular embodiments, the first immune receptor intracellular signaling domain comprises an IL-18R1 intracellular signaling domain and the second immune receptor intracellular signaling domain comprises an IL-18RAP intracellular signaling domain.

In various embodiments, the first immune receptor intracellular signaling domain comprises an IL-18RAP intracellular signaling domain and the second immune receptor intracellular signaling domain comprises an IL-18R1 intracellular signaling domain.

In some embodiments, the first immune receptor intracellular signaling domain comprises an IL-1R1 intracellular signaling domain and the second immune receptor intracellular signaling domain comprises an IL-1RAP intracellular signaling domain.

In various embodiments, the first immune receptor intracellular signaling domain comprises an IL-1RAP intracellular signaling domain and the second immune receptor intracellular signaling domain comprises an IL-1R1 intracellular signaling domain.

In certain embodiments, the first immune receptor intracellular signaling domain comprises an IL-1RL2 intracellular signaling domain and the second immune receptor intracellular signaling domain comprises an IL-1RAP intracellular signaling domain.

In various embodiments, the first immune receptor intracellular signaling domain comprises an IL-1RAP intracellular signaling domain and the second immune receptor intracellular signaling domain comprises an IL-1RL2 intracellular signaling domain.

In particular embodiments, the first immune receptor intracellular signaling domain comprises an IFNAR1 intracellular signaling domain and the second immune receptor intracellular signaling domain comprises an IFNAR2 intracellular signaling domain.

In certain embodiments, the first immune receptor intracellular signaling domain comprises an IFNAR2 intracellular signaling domain and the second immune receptor intracellular signaling domain comprises an IFNAR1 intracellular signaling domain.

In particular embodiments, the first immune receptor intracellular signaling domain comprises an TLR1 intracellular signaling domain and the second immune receptor intracellular signaling domain comprises an TLR1 intracellular signaling domain.

In some embodiments, the first immune receptor intracellular signaling domain comprises an TLR2 intracellular signaling domain and the second immune receptor intracellular signaling domain comprises an TLR2 intracellular signaling domain.

In particular embodiments, the first immune receptor intracellular signaling domain comprises an TLR3 intracellular signaling domain and the second immune receptor intracellular signaling domain comprises an TLR3 intracellular signaling domain.

In various embodiments, the first immune receptor intracellular signaling domain comprises an TLR4 intracellular signaling domain and the second immune receptor intracellular signaling domain comprises an TLR4 intracellular signaling domain.

In certain embodiments, the first immune receptor intracellular signaling domain comprises an TLR5 intracellular signaling domain and the second immune receptor intracellular signaling domain comprises an TLR5 intracellular signaling domain.

In various embodiments, the first immune receptor intracellular signaling domain comprises an TLR6 intracellular signaling domain and the second immune receptor intracellular signaling domain comprises an TLR6 intracellular signaling domain.

In particular embodiments, the first immune receptor intracellular signaling domain comprises an TLR7 intracellular signaling domain and the second immune receptor intracellular signaling domain comprises an TLR7 intracellular signaling domain.

In some embodiments, the first immune receptor intracellular signaling domain comprises an TLR8 intracellular signaling domain and the second immune receptor intracellular signaling domain comprises an TLR8 intracellular signaling domain.

In particular embodiments, the first immune receptor intracellular signaling domain comprises an TLR9 intracellular signaling domain and the second immune receptor intracellular signaling domain comprises an TLR9 intracellular signaling domain.

In some embodiments, the first immune receptor intracellular signaling domain comprises an TLR10 intracellular signaling domain and the second immune receptor intracellular signaling domain comprises an TLR10 intracellular signaling domain.

In various embodiments, the polypeptide cleavage signal is a viral self-cleaving polypeptide.

In particular embodiments, the polypeptide cleavage signal is a viral self-cleaving 2A polypeptide.

In certain embodiments, the polypeptide cleavage signal is a viral self-cleaving polypeptide selected from the group consisting of: a foot-and-mouth disease virus (FMDV) (F2A) peptide, an equine rhinitis A virus (ERAV) (E2A) peptide, a *Thosea asigna* virus (TaV) (T2A) peptide, a porcine teschovirus-1 (PTV-1) (P2A) peptide, a Theilovirus 2A peptide, and an encephalomyocarditis virus 2A peptide.

In certain embodiments, the first multimerization domain localizes extracellularly when the first polypeptide is expressed and the second multimerization domain localizes extracellularly when the second polypeptide is expressed.

In particular embodiments, a composition comprising a fusion polypeptide contemplated herein is provided.

In various embodiments, the present disclosure contemplates, in part, a composition comprising a first polypeptide comprising a first multimerization domain, a first transmembrane domain, and a first immune receptor intracellular signaling domain; and a second polypeptide comprising a second multimerization domain, a second transmembrane domain, and a second immune receptor intracellular signaling domain.

In some embodiments, the first multimerization domain and the second multimerization domain are the same.

In various embodiments, the first multimerization domain and the second multimerization domain are different.

In particular embodiments, the first multimerization domain and the second multimerization domain associate with a bridging factor selected from the group consisting of: rapamycin or a rapalog thereof, coumermycin or a derivative thereof, gibberellin or a derivative thereof, abscisic acid (ABA) or a derivative thereof, methotrexate or a derivative thereof, cyclosporin A or a derivative thereof, FK506/cyclosporin A (FKCsA) or a derivative thereof, and trimethoprim (Tmp)-synthetic ligand for FK506 binding protein (FKBP) (SLF) or a derivative thereof.

In various embodiments, the first multimerization domain and the second multimerization domain are a pair selected from the group consisting of: FKBP and FKBP12-rapamycin binding (FRB) or variants thereof; FKBP and calcineurin or variants thereof; FKBP and cyclophilin or variants thereof; FKBP and bacterial dihydrofolate reductase (DHFR) or variants thereof; calcineurin and cyclophilin or variants thereof; PYR1-like 1 (PYL1) and abscisic acid insensitive 1 (ABI1) or variants thereof; and GIB1 and GAI or variants thereof.

In particular embodiments, the first multimerization domain comprises a FKBP polypeptide or variant thereof, and the second multimerization domain comprises a FRB polypeptide or variant thereof.

In some embodiments, the first multimerization domain comprises a FRB polypeptide or variant thereof, and the second multimerization domain comprises a FKBP polypeptide or variant thereof.

In certain embodiments, the first and second multimerization domains are selected from FRB T2098L and FKBP12; and the bridging factor is AP21967.

In various embodiments, the bridging factor is selected from the group consisting of: AP21967, sirolimus, everolimus, novolimus, pimecrolimus, ridaforolimus, tacrolimus, temsirolimus, umirolimus, and zotarolimus.

In various embodiments, the first transmembrane domain and the second transmembrane domain are independently selected from the group consisting of: a CD4 transmembrane domain, a CD8α transmembrane domain, an amnionless (AMN) transmembrane domain, a CD28 transmembrane domain, a CD154 transmembrane domain, and a CD71 transmembrane domain.

In some embodiments, the first transmembrane domain and the second transmembrane domain are independently selected from the group consisting of: a CD4 transmembrane domain and a CD8α transmembrane domain.

In certain embodiments, the first transmembrane domain and the second transmembrane domain are the same.

In various embodiments, the first transmembrane domain and the second transmembrane domain are different.

In particular embodiments, first immune receptor intracellular signaling domain and the second immune receptor intracellular signaling domain are isolated from a cytokine receptor, an interleukin receptor, a pattern recognition receptor, or a toll-like receptor.

In various embodiments, the first immune receptor intracellular signaling domain comprises an IL-12Rβ2 intracellular signaling domain and the second immune receptor intracellular signaling domain comprises an IL-12Rβ1 intracellular signaling domain.

In particular embodiments, the first immune receptor intracellular signaling domain comprises an IL-12Rβ1 intracellular signaling domain and the second immune receptor intracellular signaling domain comprises an IL-12Rβ2 intracellular signaling domain.

In particular embodiments, the first immune receptor intracellular signaling domain comprises an IL-7Rα intracellular signaling domain and the second immune receptor intracellular signaling domain comprises an IL-2Rγ intracellular signaling domain.

In some embodiments, the first immune receptor intracellular signaling domain comprises an IL-2Rγ intracellular signaling domain and the second immune receptor intracellular signaling domain comprises an IL-7Rα intracellular signaling domain.

In some embodiments, the first immune receptor intracellular signaling domain comprises an IL-2Rβ intracellular signaling domain and the second immune receptor intracellular signaling domain comprises an IL-2Rγ intracellular signaling domain.

In certain embodiments, the first immune receptor intracellular signaling domain comprises an IL-2Rγ intracellular signaling domain and the second immune receptor intracellular signaling domain comprises an IL-2Rβ intracellular signaling domain.

In various embodiments, the first immune receptor intracellular signaling domain comprises an IL-21R intracellular signaling domain and the second immune receptor intracellular signaling domain comprises an IL-2Rγ intracellular signaling domain.

In particular embodiments, the first immune receptor intracellular signaling domain comprises an IL-2Rγ intracellular signaling domain and the second immune receptor intracellular signaling domain comprises an IL-21R intracellular signaling domain.

In various embodiments, the first immune receptor intracellular signaling domain comprises an IL-18R1 intracellular signaling domain and the second immune receptor intracellular signaling domain comprises an IL-18RAP intracellular signaling domain.

In certain embodiments, the first immune receptor intracellular signaling domain comprises an IL-18RAP intracellular signaling domain and the second immune receptor intracellular signaling domain comprises an IL-18R1 intracellular signaling domain.

In certain embodiments, the first immune receptor intracellular signaling domain comprises an IL-1R1 intracellular signaling domain and the second immune receptor intracellular signaling domain comprises an IL-1RAP intracellular signaling domain.

In particular embodiments, the first immune receptor intracellular signaling domain comprises an IL-1RAP intracellular signaling domain and the second immune receptor intracellular signaling domain comprises an IL-1R1 intracellular signaling domain.

In some embodiments, the first immune receptor intracellular signaling domain comprises an IL-1RL2 intracellular signaling domain and the second immune receptor intracellular signaling domain comprises an IL-1RAP intracellular signaling domain.

In certain embodiments, the first immune receptor intracellular signaling domain comprises an IL-1RAP intracellular signaling domain and the second immune receptor intracellular signaling domain comprises an IL-1RL2 intracellular signaling domain.

In various embodiments, the first immune receptor intracellular signaling domain comprises an IFNAR1 intracellular signaling domain and the second immune receptor intracellular signaling domain comprises an IFNAR2 intracellular signaling domain.

In particular embodiments, the first immune receptor intracellular signaling domain comprises an IFNAR2 intracellular signaling domain and the second immune receptor intracellular signaling domain comprises an IFNAR1 intracellular signaling domain.

In particular embodiments, the first immune receptor intracellular signaling domain comprises an TLR1 intracellular signaling domain and the second immune receptor intracellular signaling domain comprises an TLR1 intracellular signaling domain.

In particular embodiments, the first immune receptor intracellular signaling domain comprises an TLR2 intracellular signaling domain and the second immune receptor intracellular signaling domain comprises an TLR2 intracellular signaling domain.

In some embodiments, the first immune receptor intracellular signaling domain comprises an TLR3 intracellular signaling domain and the second immune receptor intracellular signaling domain comprises an TLR3 intracellular signaling domain.

In various embodiments, the first immune receptor intracellular signaling domain comprises an TLR4 intracellular signaling domain and the second immune receptor intracellular signaling domain comprises an TLR4 intracellular signaling domain.

In certain embodiments, the first immune receptor intracellular signaling domain comprises an TLR5 intracellular signaling domain and the second immune receptor intracellular signaling domain comprises an TLR5 intracellular signaling domain.

In particular embodiments, the first immune receptor intracellular signaling domain comprises an TLR6 intracellular signaling domain and the second immune receptor intracellular signaling domain comprises an TLR6 intracellular signaling domain.

In various embodiments, the first immune receptor intracellular signaling domain comprises an TLR7 intracellular signaling domain and the second immune receptor intracellular signaling domain comprises an TLR7 intracellular signaling domain.

In some embodiments, the first immune receptor intracellular signaling domain comprises an TLR8 intracellular signaling domain and the second immune receptor intracellular signaling domain comprises an TLR8 intracellular signaling domain.

In particular embodiments, the first immune receptor intracellular signaling domain comprises an TLR9 intracellular signaling domain and the second immune receptor intracellular signaling domain comprises an TLR9 intracellular signaling domain.

In various embodiments, the first immune receptor intracellular signaling domain comprises an TLR10 intracellular signaling domain and the second immune receptor intracellular signaling domain comprises an TLR10 intracellular signaling domain.

In particular embodiments, the composition further comprises a cell.

In certain embodiments, a polypeptide complex comprising a first and second polypeptide contemplated herein is provided.

In particular embodiments, a polynucleotide encoding a fusion polypeptide or a first and second polypeptide contemplated herein is provided.

In various embodiments, a cDNA encoding a fusion polypeptide or a first and second polypeptide contemplated herein is provided.

In some embodiments, an RNA encoding a fusion polypeptide or a first and second polypeptide contemplated herein is provided.

In various embodiments, vector comprising a polynucleotide contemplated herein is provided.

In certain embodiments, a cell comprising a fusion polypeptide, a first and second polypeptide, a polynucleotide, or a vector contemplated herein is provided.

In particular embodiments, the cell is a hematopoietic cell.

In various embodiments, the cell is a T cell.

In some embodiments, the cell is a CD3+, CD4$^+$, and/or CD8+ cell.

In various embodiments, the cell is an immune effector cell.

In particular embodiments, the cell is a cytotoxic T lymphocytes (CTLs), a tumor infiltrating lymphocytes (TILs), or a helper T cells.

In some embodiments, the cell is a natural killer (NK) cell or natural killer T (NKT) cell.

In particular embodiments, the source of the cell is peripheral blood mononuclear cells, bone marrow, lymph nodes tissue, cord blood, thymus issue, tissue from a site of infection, ascites, pleural effusion, spleen tissue, or tumors.

In various embodiments, the cell further comprises an engineered antigen receptor.

In certain embodiments, the engineered antigen receptor is selected from the group consisting of: an engineered T cell receptor (TCR), a chimeric antigen receptor (CAR), a DARIC receptor or components thereof, and a chimeric cytokine receptor.

In various embodiments, a composition comprising a fusion polypeptide, a first and second polypeptide, a polynucleotide, a vector, or a cell contemplated herein is provided.

In various embodiments, a pharmaceutical composition comprising a pharmaceutically acceptable carrier and a composition comprising a fusion polypeptide, a first and second polypeptide, a polynucleotide, a vector, or a cell contemplated herein is provided.

In various embodiments, a method of treating a subject in need thereof comprising administering the subject an effective amount of a composition contemplated herein is provided.

In various embodiments, a method of treating, preventing, or ameliorating at least one symptom of a cancer, infectious disease, autoimmune disease, inflammatory disease, and immunodeficiency, or condition associated therewith, comprising administering to the subject an effective amount of a composition contemplated herein is provided.

In various embodiments, a method of treating a solid cancer comprising administering to the subject an effective amount of a composition contemplated herein is provided.

In particular embodiments, the solid cancer comprises liver cancer, pancreatic cancer, lung cancer, breast cancer, ovarian cancer, prostate cancer, testicular cancer, bladder cancer, brain cancer, sarcoma, head and neck cancer, bone cancer, thyroid cancer, kidney cancer, or skin cancer.

In certain embodiments, the solid cancer is a pancreatic cancer, a lung cancer, or a breast cancer.

In various embodiments, the present disclosure contemplates, in part, a method of treating a hematological malignancy comprising administering to the subject an effective amount of a composition contemplated herein.

In particular embodiments, the hematological malignancy is a leukemia, lymphoma, or multiple myeloma.

BRIEF DESCRIPTION OF THE SEQUENCE IDENTIFIERS

Figure 1A:
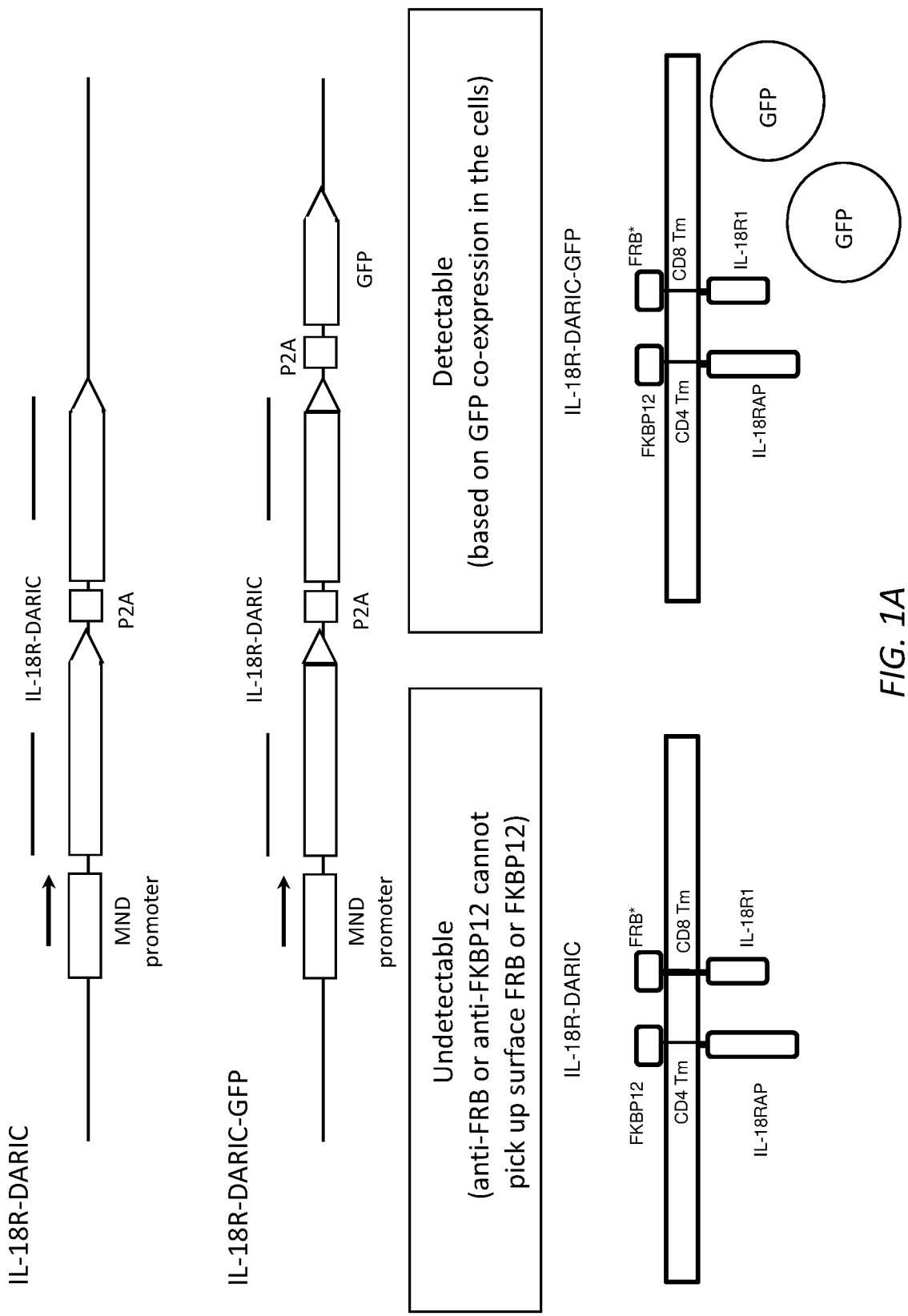
FIG. 1A shows a cartoon of IL-18R DARIC and IL-18R DARIC-GFP_(green fluorescent protein) constructs and polypeptides.

SEQ ID NO: 1 sets forth the amino acid sequence for an IL-18R DARIC signaling component.

SEQ ID NO: 2 sets forth the amino acid sequence for an IL-18R DARIC signaling component.

SEQ ID NO: 3 sets forth the amino acid sequence for an IL-18R DARIC binding component.

SEQ ID NO: 4 sets forth the amino acid sequence for an IL-18R DARIC binding component.

SEQ ID NO: 5 sets forth the amino acid sequence for an IL-18R DARIC polyprotein comprising an IL-18R DARIC binding component and signaling component separated by a viral P2A domain.

SEQ ID NO: 6 sets forth the amino acid sequence for an IL-18R DARIC-GFP polyprotein comprising an IL-18R DARIC binding component, signaling component, and GFP, each separated by a viral P2A domain.

SEQ ID NOs: 7-17 set forth the amino acid sequences of various linkers.

SEQ ID NOs: 18-42 set forth the amino acid sequences of protease cleavage sites and self-cleaving polypeptide cleavage sites.

DETAILED DESCRIPTION

A. Overview

The present disclosure generally relates to chemically regulatable polypeptides that transduce immunostimulatory signals to cells expressing the polypeptides. Without wishing to be bound by any particular theory, the polypeptides contemplated herein are fusion polypeptides comprising a chemically inducible multimerization domain linked to one or more immunostimulatory endodomains that stimulate immune effector cell activity and function. Coexpression of immunostimulatory fusion polypeptides in immune effector cells in the presence of a factor that induces multimerization and activation of the fusion polypeptides renders the cells resistant to the immunosuppressive impacts of the TME (tumor microenvironment) by restoring or increasing proinflammatory cytokine secretion. In particular preferred embodiments, a fusion polypeptide is referred to as a DARIC immune receptor.

In various embodiments, the present disclosure contemplates, in part, polypeptides that convert a chemical signal to an immunostimulatory signal mediated through or by multimerization of intracellular domains of immune receptors.

In various embodiments, the present disclosure contemplates, in part, polypeptides that convert a chemical signal to an immunostimulatory signal mediated through or by multimerization of intracellular domains of cytokine receptors.

In various embodiments, the present disclosure contemplates, in part, polypeptides that convert a chemical signal to an immunostimulatory signal mediated through or by multimerization of intracellular domains of interleukin receptors.

In various embodiments, the present disclosure contemplates, in part, polypeptides that convert a chemical signal to an immunostimulatory signal mediated through or by multimerization of intracellular domains of pattern recognition receptors.

In various embodiments, the present disclosure contemplates, in part, polypeptides that convert a chemical signal to an immunostimulatory signal mediated through or by multimerization of intracellular domains of toll-like receptors.

In particular embodiments, the present disclosure contemplates, in part, a polypeptide comprising an inducible multimerization domain, a transmembrane domain and one or more intracellular domains of one or more immune receptors; and a polypeptide comprising another inducible multimerization domain, a transmembrane domain and one or more intracellular domains of one or more immune receptors. In one embodiment, the polypeptides are linked to each other by a polypeptide cleavage signal, e.g., a 2A polypeptide cleavage signal.

In particular embodiments, the present disclosure contemplates, in part, an immune effector cell, e.g., CAR T cell or engineered TCR T cell, that expresses a polypeptide comprising an inducible multimerization domain, a transmembrane domain and one or more intracellular domains of one or more immune receptors; and a polypeptide comprising another inducible multimerization domain, a transmembrane domain and one or more intracellular domains of one or more immune receptors.

In particular embodiments, the transmembrane domains are isolated from a receptor expressed on an immune effector cell; and intracellular signaling domains are isolated from an IL-12 receptor, an IL-7 receptor, an IL-15 receptor, an IL-21 receptor, an IL-2 receptor, an IL-1 receptor, an IL-18 receptor, an IL-36 receptor, a type I IFN receptor, a TLR1 receptor, a TLR2 receptor, a TLR3 receptor, a TLR4 receptor, a TLR5 receptor, a TLR6 receptor, a TLR7 receptor, a TLR8 receptor, a TLR9 receptor, or a TLR10 receptor.

In particular embodiments, the intracellular signaling domains are isolated from IL-12Rβ2, IL-7Rα, IL-2Rγ, IL-2Rβ, IL-21R, IL-18R1, IL-18RAP, IL-1R1, IL-1RAP, IFNAR1, IFNAR2, IL-1RL2, TLR1, TLR2, TLR3, TLR4, TLR5, TLR6, TLR7, TLR8, TLR9, or TLR10.

Techniques for recombinant (i.e., engineered) DNA, peptide and oligonucleotide synthesis, immunoassays, tissue culture, transformation (e.g., electroporation, lipofection), enzymatic reactions, purification and related techniques and procedures may be generally performed as described in various general and more specific references in microbiology, molecular biology, biochemistry, molecular genetics, cell biology, virology and immunology as cited and discussed throughout the present specification. See, e.g., Sambrook et al., *Molecular Cloning: A Laboratory Manual*, 3d ed., Cold Spring Harbor Laboratory Press, Cold Spring Harbor, N.Y.; *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, NY); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid The Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); *Next-Generation Genome Sequencing* (Janitz, 2008 Wiley-VCH); *PCR Protocols (Methods in Molecular Biology)* (Park, Ed., 3rd Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir and C C Blackwell, eds., 1986); Roitt, *Essential Immunology*, 6th Edition, (Blackwell Scientific Publications, Oxford, 1988); *Current Protocols in Immunology* (Q. E. Coligan, A. M. Kruisbeek, D. H. Margulies, E. M. Shevach and W. Strober, eds., 1991); *Annual Review of Immunology*; as well as monographs in journals such as *Advances in Immunology*.

B. Definitions

Prior to setting forth this disclosure in more detail, it may be helpful to an understanding thereof to provide definitions of certain terms to be used herein.

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined below.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

An "antigen (Ag)" refers to a compound, composition, or substance that can stimulate the production of antibodies or a T cell response in an animal, including compositions (such as one that includes a cancer-specific protein) that are injected or absorbed into an animal. Exemplary antigens include but are not limited to lipids, carbohydrates, polysaccharides, glycoproteins, peptides, or nucleic acids. An antigen reacts with the products of specific humoral or cellular immunity, including those induced by heterologous antigens, such as the disclosed antigens.

A "target antigen" or "target antigen of interest" is an antigen that a binding domain contemplated herein, is designed to bind. In particular embodiments, the target antigen is selected from the group consisting of: alpha folate receptor, 5T4, αvβ6 integrin, BCMA, B7-H3, B7-H6, CAIX, CD16, CD19, CD20, CD22, CD30, CD33, CD3γ, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, STn, TAG72, TEMs, VEGFR2, and WT-1. In one embodiment, the antigen is an MHC-peptide complex, such as a class I MHC-peptide complex or a class II MHC-peptide complex.

An "antibody" refers to a binding agent that is a polypeptide comprising at least a light chain or heavy chain immunoglobulin variable region which specifically recognizes and binds an epitope of an antigen, such as a lipid, carbohydrate, polysaccharide, glycoprotein, peptide, or nucleic acid containing an antigenic determinant, such as those recognized by an immune cell.

An "epitope" or "antigenic determinant" refers to the region of an antigen to which a binding agent binds.

Antibodies include antigen binding fragments thereof, such as a Camel Ig, a Llama Ig, an Alpaca Ig, Ig NAR, a Fab' fragment, a F(ab')$_2$ fragment, a bispecific Fab dimer (Fab2), a trispecific Fab trimer (Fab3), an Fv, an single chain Fv protein ("scFv"), a bis-scFv, (scFv)$_2$, a minibody, a diabody, a triabody, a tetrabody, a disulfide stabilized Fv protein ("dsFv"), and a single-domain antibody (sdAb, a camelid VHH, Nanobody) and portions of full length antibodies responsible for antigen binding. The term also includes genetically engineered forms such as chimeric antibodies (for example, humanized murine antibodies), heteroconjugate antibodies (such as, bispecific antibodies) and antigen binding fragments thereof. See also, Pierce Catalog and Handbook, 1994-1995 (Pierce Chemical Co., Rockford, IL); Kuby, J., Immunology, 3rd Ed., W. H. Freeman & Co., New York, 1997.

A "linker" refers to a plurality of amino acid residues between the various polypeptide domains added for appropriate spacing and conformation of the molecule. In particular embodiments, the linker is a variable region linking sequence. A "variable region linking sequence," is an amino acid sequence that connects the $V_H$ and $V_L$ domains and provides a spacer function compatible with interaction of the two sub-binding domains so that the resulting polypeptide retains a specific binding affinity to the same target molecule as an antibody that comprises the same light and heavy chain variable regions. In particular embodiments, a linker separates one or more heavy or light chain variable domains, hinge domains, multimerization domains, transmembrane domains, co-stimulatory domains, and/or primary signaling domains.

Illustrated examples of linkers suitable for use in particular embodiments contemplated herein include, but are not limited to the following amino acid sequences: GGG; DGGGS (SEQ ID NO: 7); TGEKP (SEQ ID NO: 8) (see, e.g., Liu et al., PNAS 5525-5530 (1997)); GGRR (SEQ ID NO: 9) (Pomerantz et al. 1995, supra); (GGGGS)$_n$ wherein n=1, 2, 3, 4 or 5 (SEQ ID NO: 10) (Kim et al., PNAS 93, 1156-1160 (1996); EGKSSGSGSESKVD (SEQ ID NO: 11) (Chaudhary et al., 1990, Proc. Natl. Acad. Sci. U.S.A. 87:1066-1070); KESGSVSSEQLAQFRSLD (SEQ ID NO: 12) (Bird et al., 1988, Science 242:423-426), GGRRGGGS (SEQ ID NO: 13); LRQRDGERP (SEQ ID NO: 14); LRQKDGGGSERP (SEQ ID NO: 15); LRQKD(GGGS)$_2$ERP (SEQ ID NO: 16). Alternatively, flexible linkers can be rationally designed using a computer program capable of modeling both DNA-binding sites and the peptides themselves (Desjarlais & Berg, *PNAS* 90:2256-2260 (1993), *PNAS* 91:11099-11103 (1994) or by phage display methods. In one embodiment, the linker comprises the following amino acid sequence: GSTSGSGKPGSGEGSTKG (SEQ ID NO: 17) (Cooper et al., *Blood*, 101(4): 1637-1644 (2003)).

A "spacer domain," refers to a polypeptide that separates two domains. In one embodiment, a spacer domain moves an antigen binding domain away from the effector cell surface to enable proper cell/cell contact, antigen binding and activation (Patel et al., *Gene Therapy*, 1999; 6: 412-419). In particular embodiments, a spacer domain separates one or more heavy or light chain variable domains, multimerization domains, transmembrane domains, co-stimulatory domains, and/or primary signaling domains. The spacer domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region.

A "hinge domain," refers to a polypeptide that plays a role in positioning the antigen binding domain away from the effector cell surface to enable proper cell/cell contact, antigen binding and activation. In particular embodiments, polypeptides may comprise one or more hinge domains between the binding domain and the multimerization domain, between the binding domain and the transmembrane domain (TM), or between the multimerization domain and the transmembrane domain. The hinge domain may be derived either from a natural, synthetic, semi-synthetic, or recombinant source. The hinge domain can include the amino acid sequence of a naturally occurring immunoglobulin hinge region or an altered immunoglobulin hinge region.

A "multimerization domain," as used herein, refers to a polypeptide that preferentially interacts or associates with another different polypeptide directly or via a bridging molecule, e.g., a chemically inducible dimerizer, wherein the interaction of different multimerization domains substantially contributes to or efficiently promotes multimerization (i.e., the formation of a dimer, trimer, or multipartite complex, which may be a homodimer, heterodimer, homotrimer, heterotrimer, homomultimer, heteromultimer). A multimerization domain may be derived either from a natural, synthetic, semi-synthetic, or recombinant source.

Illustrative examples of multimerization domains suitable for use in particular embodiments contemplated herein include an FK506 binding protein (FKBP) polypeptide or variants thereof, an FKBP12-rapamycin binding (FRB)

polypeptide or variants thereof, a calcineurin polypeptide or variants thereof, a cyclophilin polypeptide or variants thereof, a bacterial dihydrofolate reductase (DHFR) polypeptide or variants thereof, a PYR1-like 1 (PYL1) polypeptide or variants thereof, an abscisic acid insensitive 1 (ABI1) polypeptide or variants thereof, a GIB1 polypeptide or variants thereof, or a GAI polypeptide or variants thereof.

As used herein, the term "FKBP-rapamycin binding polypeptide" refers to an FRB polypeptide. In particular embodiments, the FRB polypeptide is an FKBP12-rapamycin binding polypeptide. FRB polypeptides suitable for use in particular embodiments contemplated herein generally contain at least about 85 to about 100 amino acid residues. In certain embodiments, the FRB polypeptide comprises a 93 amino acid sequence Ile-2021 through Lys-2113 and a mutation of T2098L, with reference to GenBank Accession No. L34075.1. An FRB polypeptide contemplated herein binds to an FKBP polypeptide through a bridging factor, thereby forming a tripartite complex.

As used herein, the term "FK506 binding protein" refers to an FKBP polypeptide. In particular embodiments, the FKBP polypeptide is an FKBP12 polypeptide. In certain embodiments, an FKBP domain may also be referred to as a "rapamycin binding domain". Information concerning the nucleotide sequences, cloning, and other aspects of various FKBP species is known in the art (see, e.g., Staendart et al., *Nature* 346:671, 1990 (human FKBP12); Kay, *Biochem. J.* 314:361, 1996). An FKBP polypeptide contemplated herein binds to an FRB polypeptide through a bridging factor, thereby forming a tripartite complex.

A "bridging factor" refers to a molecule that associates with and that is disposed between two or more multimerization domains. In particular embodiments, multimerization domains substantially contribute to or efficiently promote formation of a polypeptide complex only in the presence of a bridging factor. In particular embodiments, multimerization domains do not contribute to or do not efficiently promote formation of a polypeptide complex in the absence of a bridging factor. Illustrative examples of bridging factors suitable for use in particular embodiments contemplated herein include, but are not limited to AP21967, rapamycin (sirolimus) or a rapalog thereof, coumermycin or a derivative thereof, gibberellin or a derivative thereof, abscisic acid (ABA) or a derivative thereof, methotrexate or a derivative thereof, cyclosporin A or a derivative thereof, FKCsA or a derivative thereof, trimethoprim (Tmp)-synthetic ligand for FKBP (SLF) or a derivative thereof, or any combination thereof.

Rapamycin analogs (rapalogs) include but are not limited to those disclosed in U.S. Pat. No. 6,649,595, which rapalog structures are incorporated herein by reference in their entirety. In certain embodiments, a bridging factor is a rapalog with substantially reduced immunosuppressive effect as compared to rapamycin. In a preferred embodiment, the rapalog is AP21967 (also known as C-16-(S)-7-methylindolerapamycin, $IC_{50}$=10 nM, a chemically modified non-immunosuppressive rapamycin analogue). Other illustrative rapalogs suitable for use in particular embodiments contemplated herein include, but are not limited to, everolimus, novolimus, pimecrolimus, ridaforolimus, tacrolimus, temsirolimus, umirolimus, and zotarolimus.

A "substantially reduced immunosuppressive effect" refers to at least less than 0.1 to 0.005 times the immunosuppressive effect observed or expected for the same dose measured either clinically or in an appropriate in vitro (e.g., inhibition of T cell proliferation) or in vivo surrogate of human immunosuppressive activity.

A "transmembrane domain" or "TM domain" is a domain that anchors a polypeptide to the plasma membrane of a cell. The TM domain may be derived either from a natural, synthetic, semi-synthetic, or recombinant source.

An "intracellular signaling domain" or "endodomain" refers to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal.

The term "effector function" or "effector cell function" refers to a specialized function of an immune effector cell. Effector function includes, but is not limited to, activation, cytokine production, proliferation and cytotoxic activity, including the release of cytotoxic factors, or other cellular responses elicited with antigen binding to the receptor expressed on the immune effector cell.

It is known that signals generated through the TCR alone are insufficient for full activation of the T cell and that a secondary or co-stimulatory signal is also required. Thus, T cell activation can be said to be mediated by two distinct classes of intracellular signaling domains: primary signaling domains that initiate antigen-dependent primary activation through the TCR (e.g., a TCR/CD3 complex) and co-stimulatory signaling domains that act in an antigen-independent manner to provide a secondary or co-stimulatory signal.

A "primary signaling domain" refers to a signaling domain that regulates the primary activation of the TCR complex either in a stimulatory way, or in an inhibitory way. Primary signaling domains that act in a stimulatory manner may contain signaling motifs which are known as immunoreceptor tyrosine-based activation motifs or ITAMs. Illustrative examples of ITAM containing primary signaling domains that are suitable for use in particular embodiments include, but are not limited to those derived from FcRγ, FcRβ, CD3γ, CD3δ, CD3ε, CD3ζ, CD22, CD79a, CD79b, and CD66d.

As used herein, the term, "co-stimulatory signaling domain," or "co-stimulatory domain" refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen. Illustrative examples of such co-stimulatory molecules from which co-stimulatory domains may be isolated include, but are not limited to: TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70.

An "immune disorder" refers to a disease that evokes a response from the immune system. In particular embodiments, the term "immune disorder" refers to a cancer, an autoimmune disease, or an immunodeficiency. In one embodiment, immune disorders encompass infectious disease.

As used herein, the term "cancer" relates generally to a class of diseases or conditions in which abnormal cells divide without control and can invade nearby tissues.

As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor.

As used herein, the term "benign" or "non-malignant" refers to tumors that may grow larger but do not spread to other parts of the body. Benign tumors are self-limited and typically do not invade or metastasize.

A "cancer cell" refers to an individual cell of a cancerous growth or tissue. Cancer cells include both solid cancers and liquid cancers. A "tumor" or "tumor cell" refers generally to a swelling or lesion formed by an abnormal growth of cells, which may be benign, pre-malignant, or malignant. Most cancers form tumors, but liquid cancers, e.g., leukemia, do not necessarily form tumors. For those cancers that form tumors, the terms cancer (cell) and tumor (cell) are used interchangeably. The amount of a tumor in an individual is the "tumor burden" which can be measured as the number, volume, or weight of the tumor.

The term "relapse" refers to the diagnosis of return, or signs and symptoms of return, of a cancer after a period of improvement or remission.

"Remission," is also referred to as "clinical remission," and includes both partial and complete remission. In partial remission, some, but not all, signs and symptoms of cancer have disappeared. In complete remission, all signs and symptoms of cancer have disappeared, although cancer still may be in the body.

"Refractory" refers to a cancer that is resistant to, or non-responsive to, therapy with a particular therapeutic agent. A cancer can be refractory from the onset of treatment (i.e., non-responsive to initial exposure to the therapeutic agent), or as a result of developing resistance to the therapeutic agent, either over the course of a first treatment period or during a subsequent treatment period.

"Antigen negative" refers to a cell that does not express antigen or expresses a negligible amount of antigen that is undetectable. In one embodiment, antigen negative cells do not bind receptors directed to the antigen. In one embodiment, antigen negative cells do not substantially bind receptors directed to the antigen.

An "autoimmune disease" refers to a disease in which the body produces an immunogenic (i.e., immune system) response to some constituent of its own tissue. In other words, the immune system loses its ability to recognize some tissue or system within the body as "self" and targets and attacks it as if it were foreign. Autoimmune diseases can be classified into those in which predominantly one organ is affected (e.g., hemolytic anemia and anti-immune thyroiditis), and those in which the autoimmune disease process is diffused through many tissues (e.g., systemic lupus erythematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

An "immunodeficiency" means the state of a patient whose immune system has been compromised by disease or by administration of chemicals. This condition makes the system deficient in the number and type of blood cells needed to defend against a foreign substance. Immunodeficiency conditions or diseases are known in the art and include, for example, AIDS (acquired immunodeficiency syndrome), SCID (severe combined immunodeficiency disease), selective IgA deficiency, common variable immunodeficiency, X-linked agammaglobulinemia, chronic granulomatous disease, hyper-IgM syndrome, and diabetes.

An "infectious disease" refers to a disease that can be transmitted from person to person or from organism to organism and is caused by a microbial or viral agent (e.g., common cold). Infectious diseases are known in the art and include, for example, hepatitis, sexually transmitted diseases (e.g., *Chlamydia*, gonorrhea), tuberculosis, HIV/AIDS, diphtheria, hepatitis B, hepatitis C, cholera, and influenza.

As used herein, the terms "individual" and "subject" are often used interchangeably and refer to any animal that exhibits a symptom of cancer or other immune disorder that can be treated with the compositions and methods contemplated elsewhere herein. Suitable subjects (e.g., patients) include laboratory animals (such as mouse, rat, rabbit, or guinea pig), farm animals, and domestic animals or pets (such as a cat or dog). Non-human primates and, preferably, human patients, are included. Typical subjects include human patients that have, have been diagnosed with, or are at risk or having, cancer or another immune disorder.

As used herein, the term "patient" refers to a subject that has been diagnosed with cancer or another immune disorder that can be treated with the compositions and methods disclosed elsewhere herein.

As used herein "treatment" or "treating," includes any beneficial or desirable effect on the symptoms or pathology of a disease or pathological condition and may include even minimal reductions in one or more measurable markers of the disease or condition being treated. Treatment can involve optionally either the reduction of the disease or condition, or the delaying of the progression of the disease or condition, e.g., delaying tumor outgrowth. "Treatment" does not necessarily indicate complete eradication or cure of the disease or condition, or associated symptoms thereof.

As used herein, "prevent," and similar words such as "prevented," "preventing" etc., indicate an approach for preventing, inhibiting, or reducing the likelihood of the occurrence or recurrence of, a disease or condition. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

As used herein, the phrase "ameliorating at least one symptom of" refers to decreasing one or more symptoms of the disease or condition for which the subject is being treated. In particular embodiments, the disease or condition being treated is a cancer, wherein the one or more symptoms ameliorated include, but are not limited to, weakness, fatigue, shortness of breath, easy bruising and bleeding, frequent infections, enlarged lymph nodes, distended or painful abdomen (due to enlarged abdominal organs), bone or joint pain, fractures, unplanned weight loss, poor appetite, night sweats, persistent mild fever, and decreased urination (due to impaired kidney function).

By "enhance" or "promote," or "increase" or "expand" refers generally to the ability of a composition contemplated herein to produce, elicit, or cause a greater physiological response (i.e., downstream effects) compared to the response caused by either vehicle or a control molecule/composition. A measurable physiological response may include an increase in T cell expansion, activation, persistence, cytokine secretion, and/or an increase in cancer cell killing ability, among others apparent from the understanding in the art and the description herein. An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle or a control composition.

By "decrease" or "lower," or "lessen," or "reduce," or "abate" refers generally to the ability of composition contemplated herein to produce, elicit, or cause a lesser physiological response (i.e., downstream effects) compared to the response caused by either vehicle or a control molecule/composition. A "decrease" or "reduced" amount is typically a "statistically significant" amount, and may include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, a control composition, or the response in a particular cell lineage.

By "maintain," or "preserve," or "maintenance," or "no change," or "no substantial change," or "no substantial decrease" refers generally to the ability of a composition contemplated herein to produce, elicit, or cause a substantially similar or comparable physiological response (i.e., downstream effects) in a cell, as compared to the response caused by either vehicle, a control molecule/composition, or the response in a particular cell lineage. A comparable response is one that is not significantly different or measurable different from the reference response.

Additional definitions are set forth throughout this disclosure.

C. Daric Immune Receptors

In particular embodiments, one or more DARIC immune receptors that transduce an immunostimulatory signal upon exposure to a bridging factor is contemplated. As used herein, the term "DARIC immune receptor" refers to one or more non-naturally occurring polypeptides that transduces an immunostimulatory signal in an immune effector cell upon exposure to a multimerizing agent or bridging factor, e.g., stimulating immune effector cell activity and function, increasing production and/or secretion of proinflammatory cytokines.

In particular embodiments, the DARIC immune receptor is a polypeptide comprising a first multimerization domain, a transmembrane domain, an intracellular signaling domain of an immune receptor, e.g., a human immune receptor, including, but not limited to a cytokine receptor, an interleukin receptor, a pattern recognition receptor, and a toll-like receptor; a polypeptide cleavage signal; and a second multimerization domain, a transmembrane domain, and an intracellular signaling domain of an immune receptor, e.g., a human immune receptor, including, but not limited to a cytokine receptor, an interleukin receptor, a pattern recognition receptor, and a toll-like receptor.

In other particular embodiments, the DARIC immune receptor is a complex of polypeptides comprising a first polypeptide comprising a first multimerization domain, a transmembrane domain, and an intracellular signaling domain of an immune receptor including, but not limited to a cytokine receptor, an interleukin receptor, a pattern recognition receptor, and a toll-like receptor; and a second polypeptide comprising a second multimerization domain, a transmembrane domain, and an intracellular signaling domain of an immune receptor including, but not limited to a cytokine receptor, an interleukin receptor, a pattern recognition receptor, and a toll-like receptor.

As used herein, the term "immune receptor" refers to a receptor that is expressed on the surface of an immune cell that modulates an immune response upon binding its cognate ligand. Immune receptors suitable for use in particular embodiments include, but are not limited to: cytokine receptors, interleukin receptors, pattern recognition receptors, and toll-like receptors, wherein signaling through the immune receptor stimulates an immune response.

Illustrative examples of multimerization domains suitable for use in particular DARIC immune receptors contemplated herein include, but are not limited to, an FK506 binding protein (FKBP) polypeptide or variants thereof, an FKBP12-rapamycin binding (FRB) polypeptide or variants thereof, a calcineurin polypeptide or variants thereof, a cyclophilin polypeptide or variants thereof, a bacterial dihydrofolate reductase (DHFR) polypeptide or variants thereof, a PYR1-like 1 (PYL1) polypeptide or variants thereof, an abscisic acid insensitive 1 (ABI1) polypeptide or variants thereof, a GIB1 polypeptide or variants thereof, or a GAI polypeptide or variants thereof.

Illustrative examples of immune receptor transmembrane domains suitable for use in particular DARIC immune receptors contemplated herein include, but are not limited to, the transmembrane region(s) of the alpha, beta, gamma, or delta chain of a T-cell receptor, CD3ε, CD3ζ, CD4, CD5, CD8α, CD9, CD 16, CD22, CD27, CD28, CD33, CD3γ, CD45, CD64, CD71, CD80, CD86, CD 134, CD137, CD152, CD 154, AMN, PD1, IL-12Rβ2, IL-7Rα, IL-2Rγ, IL-2Rβ, IL-21R, IL-18R1, IL-18RAP, IL-1R1, IL-1RAP, IFNAR1, IFNAR2, IL-1RL2, TLR1, TLR2, TLR3, TLR4, TLR5, TLR6, TLR7, TLR8, TLR9, or TLR10.

Illustrative examples of immune receptor intracellular signaling domains suitable for use in particular DARIC immune receptors contemplated herein include, but are not limited to, intracellular signaling domains isolated from an IL-12 receptor, an IL-7 receptor, an IL-15 receptor, an IL-21 receptor, an IL-2 receptor, an IL-1 receptor, an IL-18 receptor, an IL-36 receptor, a type I IFN receptor, a TLR1 receptor, a TLR2 receptor, a TLR3 receptor, a TLR4 receptor, a TLR5 receptor, a TLR6 receptor, a TLR7 receptor, a TLR8 receptor, a TLR9 receptor, or a TLR10 receptor.

Illustrative examples of immune receptor intracellular signaling domains suitable for use in particular DARIC immune receptors contemplated herein include, but are not limited to, IL-12Rβ2, IL-7Rα, IL-2Rγ, IL-2Rβ, IL-21R, IL-18R1, IL-18RAP, IL-1R1, IL-1RAP, IFNAR1, IFNAR2, IL-1RL2, TLR1, TLR2, TLR3, TLR4, TLR5, TLR6, TLR7, TLR8, TLR9, or TLR10.

Illustrative examples of cytokine receptor intracellular signaling domains suitable for use in particular DARIC immune receptors contemplated herein include, but are not limited to, IL-12Rβ2, IL-7Rα, IL-2Rγ, IL-2Rβ, IL-21R, IL-18R1, IL-18RAP, IL-1R1, IL-1RAP, IFNAR1, IFNAR2, and IL-1RL2.

Illustrative examples of interleukin receptor intracellular signaling domains suitable for use in particular DARIC immune receptors contemplated herein include, but are not limited to, IL-12Rβ2, IL-7Rα, IL-2Rγ, IL-2Rβ, IL-21R, IL-18R1, IL-18RAP, IL-1R1, IL-1RAP, and IL-1RL2.

Illustrative examples of toll-like receptor intracellular signaling domains suitable for use in particular DARIC immune receptors contemplated herein include, but are not limited to, TLR1, TLR2, TLR3, TLR4, TLR5, TLR6, TLR7, TLR8, TLR9, and TLR10.

1. IL-18 Daric Immune Receptor

Interleukin-18 (IL-18) is a cytokine that promotes T cell function and activity by, in part, increasing IFNγ expression, increasing T cell proliferation, and protecting against activation induced cell death (AICD). IL-18 binds interleukin 18 receptor 1, (IL-18R1, also known as CD218a) and interleukin 18 receptor accessory protein (IL-18RAP, CD218b).

IL-18 signaling through IL-18R1 and IL-18RAP results in activation through the MyD88 adaptor protein and IRAK4 phosphorylation. Phosphorylation of IRAK4 and subsequent phosphorylation of IRAK1/2 ultimately leads to activation of NF-kappa B and AP-1 transcription factors to increase IFNγ expression and increase sensitivity to IL-12. The transcriptional program induced by IL-18 also increases T cell proliferation and protects against AICD.

In various embodiments, one or more immune effector cells, including immune effector cells expressing an engineered antigen receptor, are modified by introducing one or more polynucleotides or vectors encoding an IL-18 DARIC immune receptor. In various embodiments, one or more immune effector cells are modified by introducing one or more polynucleotides or vectors encoding an IL-18 DARIC immune receptor and an engineered antigen receptor.

In particular embodiments, the IL-18 DARIC immune receptor transduces an IL-18-mediated immunostimulatory signal upon exposure to a bridging factor. In particular embodiments an IL-18 DARIC immune receptor contemplated herein comprises: a first multimerization domain, a transmembrane domain, and an IL-18RAP intracellular signaling domain; a polypeptide cleavage signal; and a second multimerization domain, a transmembrane domain, and an IL-18R1 intracellular signaling domain. In particular embodiments an IL-18 DARIC immune receptor contemplated herein comprises: a first multimerization domain, a transmembrane domain, and an IL-18R1 intracellular signaling domain; a polypeptide cleavage signal; and a second multimerization domain, a transmembrane domain, and an IL-18RAP intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a *Thosea asigna* virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

In particular embodiments, the IL-18 DARIC immune receptor is a complex of polypeptides comprising a first polypeptide comprising a first multimerization domain, a first transmembrane domain, and an IL-18RAP intracellular signaling domain; and a polypeptide comprising a second multimerization domain, a second transmembrane domain, and an IL-18R1 intracellular signaling domain. In particular embodiments, an IL-18 immune receptor is a complex of polypeptides comprising a first polypeptide comprising a first multimerization domain, a first transmembrane domain, and an IL-18R1 intracellular signaling domain; and a polypeptide comprising a second multimerization domain, a second transmembrane domain, and an IL-18RAP intracellular signaling domain.

In particular embodiments, the first and second transmembrane domains are selected from the group consisting of: CD4, CD5, CD8α, CD9, CD 16, CD22, CD27, CD28, CD33, CD3γ, CD45, CD64, CD71, CD80, CD86, CD 134, CD137, CD152, CD 154, AMN, and PD1.

In one embodiment, the first and second multimerization domains are the same.

In certain embodiments, an IL-18 DARIC immune receptor comprises a first or second multimerization domain selected from a pair selected from FKBP and FRB, FKBP and calcineurin, FKBP and cyclophilin, FKBP and bacterial DHFR, calcineurin and cyclophilin, PYL1 and ABI1, or GIB1 and GAI, or variants thereof.

In certain embodiments, a first polypeptide comprises a multimerization domain comprising an FKBP polypeptide or variant thereof, a CD4 or CD8α transmembrane domain, and an IL-18R1 intracellular signaling domain; and a second polypeptide comprises a multimerization domain comprising an FRB polypeptide or variant thereof, a CD4 or CD8α transmembrane domain, and an IL-18RAP intracellular signaling domain.

In certain embodiments, a first polypeptide comprises a multimerization domain comprising an FRB polypeptide or variant thereof, a CD4 or CD8α transmembrane domain, and an IL-18R1 intracellular signaling domain; and a second polypeptide comprises a multimerization domain comprising an FKBP polypeptide or variant thereof, a CD4 or CD8α transmembrane domain, and an IL-18RAP intracellular signaling domain.

In some embodiments, the bridging factor is AP21967, sirolimus, everolimus, novolimus, pimecrolimus, ridaforolimus, tacrolimus, temsirolimus, umirolimus, or zotarolimus.

In particular embodiments, the FRB polypeptide is FRB T2098L; the FKBP polypeptide is FKBP12; and the bridging factor is AP21967.

In particular embodiments, the FRB polypeptide is FRB; the FKBP polypeptide is FKBP12; and the bridging factor is rapamycin, temsirolimus or everolimus.

2. IL-12 DARIC Immune Receptor

Interleukin-12 (IL-12) is a cytokine that promotes T cell function and activity by, in part, increasing IFNγ expression, increasing T cell proliferation, and potentiating IL-12 signaling. IL-12 binds interleukin 12 receptor, beta 1 (IL-12Rβ1, also known as CD212) and interleukin 12 receptor, beta 2 (IL-12Rβ2).

IL-12 signaling through IL-12Rβ1 and IL-12Rβ2 results in STAT3, STAT4, and STAT5 phosphorylation. Phosphorylated STAT3/STAT4 translocates to the nucleus and binds the IFNγ promoter to increase IFNγ expression. Phosphorylated STAT4 also recruits Jun oncogene (c-Jun) to IFNγ promoter to increase IFNγ expression and potentiates IL-12 signaling by increasing transcription of IL-12Rβ2. STAT5 phosphorylation increases T cell proliferation.

IL-12 signaling also increases expression of interleukin 2 receptor, alpha (IL-2R) by recruiting STAT4 and c-Jun to the promoter of IL-2R, thereby enhancing T cell proliferation.

In various embodiments, one or more immune effector cells, including immune effector cells expressing an engineered antigen receptor, are modified by introducing one or more polynucleotides or vectors encoding an IL-12 DARIC immune receptor. In various embodiments, one or more immune effector cells are modified by introducing one or more polynucleotides or vectors encoding an IL-12 DARIC immune receptor and an engineered antigen receptor.

In particular embodiments, the IL-12 DARIC immune receptor transduces an IL-12-mediated immunostimulatory signal upon exposure to a bridging factor. In particular embodiments an IL-12 DARIC immune receptor contemplated herein comprises: a first multimerization domain, a transmembrane domain, and an IL-12Rβ1 intracellular signaling domain; a polypeptide cleavage signal; and a second multimerization domain, a transmembrane domain, and an IL-12Rβ2 intracellular signaling domain. In particular embodiments an IL-12 DARIC immune receptor contemplated herein comprises: a first multimerization domain, a transmembrane domain, and an IL-12Rβ2 intracellular signaling domain; a polypeptide cleavage signal; and a second multimerization domain, a transmembrane domain, and an IL-12Rβ1 intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a *Thosea asigna* virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

In particular embodiments, the IL-12 DARIC immune receptor is a complex of polypeptides comprising a first polypeptide comprising a first multimerization domain, a first transmembrane domain, and an IL-12Rβ1 intracellular signaling domain; and a polypeptide comprising a second multimerization domain, a second transmembrane domain, and an IL-12Rβ2 intracellular signaling domain. In particular embodiments, an IL-12 immune receptor is a complex of polypeptides comprising a first polypeptide comprising a first multimerization domain, a first transmembrane domain, and an IL-12Rβ2 intracellular signaling domain; and a polypeptide comprising a second multimerization domain, a second transmembrane domain, and an IL-12Rβ1 intracellular signaling domain.

In particular embodiments, the first and second transmembrane domains are selected from the group consisting of: CD4, CD5, CD8α, CD9, CD 16, CD22, CD27, CD28, CD33, CD3γ, CD45, CD64, CD71, CD80, CD86, CD 134, CD137, CD152, CD 154, AMN, and PD1.

In one embodiment, the first and second multimerization domains are the same.

In certain embodiments, an IL-12 DARIC immune receptor comprises a first or second multimerization domain selected from a pair selected from FKBP and FRB, FKBP and calcineurin, FKBP and cyclophilin, FKBP and bacterial DHFR, calcineurin and cyclophilin, PYL1 and ABI1, or GIB1 and GAI, or variants thereof.

In certain embodiments, a first polypeptide comprises a multimerization domain comprising an FKBP polypeptide or variant thereof, a CD4 or CD8α transmembrane domain, and an IL-12Rβ1 intracellular signaling domain; and a second polypeptide comprises a multimerization domain comprising an FRB polypeptide or variant thereof, a CD4 or CD8α transmembrane domain, and an IL-12Rβ2 intracellular signaling domain.

In certain embodiments, a first polypeptide comprises a multimerization domain comprising an FRB polypeptide or variant thereof, a CD4 or CD8α transmembrane domain, and an IL-12Rβ1 intracellular signaling domain; and a second polypeptide comprises a multimerization domain comprising an FKBP polypeptide or variant thereof, a CD4 or CD8α transmembrane domain, and an IL-12Rβ2 intracellular signaling domain.

In some embodiments, the bridging factor is AP21967, sirolimus, everolimus, novolimus, pimecrolimus, ridaforolimus, tacrolimus, temsirolimus, umirolimus, or zotarolimus.

In particular embodiments, the FRB polypeptide is FRB T2098L; the FKBP polypeptide is FKBP12; and the bridging factor is AP21967.

In particular embodiments, the FRB polypeptide is FRB; the FKBP polypeptide is FKBP12; and the bridging factor is rapamycin, temsirolimus or everolimus.

3. IL-7 Daric Immune Receptor

Interleukin-7 (IL-7) is a cytokine that promotes T cell function and activity by, in part, improving T cell precursor survival and proliferation. IL-7 binds interleukin 7 receptor alpha (IL-7Rα, also known as CD127) and interleukin 2 receptor, common gamma chain (IL-2Rγ, also known as CD132 and γc). IL-7 signaling activates the JAK/STAT, PI-3K, and Src kinase pathways and results in transcription of anti-apoptotic genes and genes that promote proliferation of T cell precursors.

In various embodiments, one or more immune effector cells, including immune effector cells expressing an engineered antigen receptor, are modified by introducing one or more polynucleotides or vectors encoding an IL-7 DARIC immune receptor. In various embodiments, one or more immune effector cells are modified by introducing one or more polynucleotides or vectors encoding an IL-7 DARIC immune receptor and an engineered antigen receptor.

In particular embodiments, the IL-7 DARIC immune receptor transduces an IL-7-mediated immunostimulatory signal upon exposure to a bridging factor. In particular embodiments an IL-7 DARIC immune receptor contemplated herein comprises: a first multimerization domain, a transmembrane domain, and an IL-7Rα intracellular signaling domain; a polypeptide cleavage signal; and a second multimerization domain, a transmembrane domain, and an IL-2Rγ intracellular signaling domain. In particular embodiments an IL-7 DARIC immune receptor contemplated herein comprises: a first multimerization domain, a transmembrane domain, and an IL-2Rγ intracellular signaling domain; a polypeptide cleavage signal; and a second multimerization domain, a transmembrane domain, and an IL-7Rα intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A)

peptide, a *Thosea asigna* virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

In particular embodiments, the IL-7 DARIC immune receptor is a complex of polypeptides comprising a first polypeptide comprising a first multimerization domain, a first transmembrane domain, and an IL-7Rα intracellular signaling domain; and a polypeptide comprising a second multimerization domain, a second transmembrane domain, and an IL-2Rγ intracellular signaling domain. In particular embodiments, an IL-7 immune receptor is a complex of polypeptides comprising a first polypeptide comprising a first multimerization domain, a first transmembrane domain, and an IL-2Rγ intracellular signaling domain; and a polypeptide comprising a second multimerization domain, a second transmembrane domain, and an IL-7Rα intracellular signaling domain.

In particular embodiments, the first and second transmembrane domains are selected from the group consisting of: CD4, CD5, CD8α, CD9, CD 16, CD22, CD27, CD28, CD33, CD3γ, CD45, CD64, CD71, CD80, CD86, CD 134, CD137, CD152, CD 154, AMN, and PD1.

In one embodiment, the first and second multimerization domains are the same.

In certain embodiments, an IL-7 DARIC immune receptor comprises a first or second multimerization domain selected from a pair selected from FKBP and FRB, FKBP and calcineurin, FKBP and cyclophilin, FKBP and bacterial DHFR, calcineurin and cyclophilin, PYL1 and ABI1, or GIB1 and GAI, or variants thereof.

In certain embodiments, a first polypeptide comprises a multimerization domain comprising an FKBP polypeptide or variant thereof, a CD4 or CD8α transmembrane domain, and an IL-7Rα intracellular signaling domain; and a second polypeptide comprises a multimerization domain comprising an FRB polypeptide or variant thereof, a CD4 or CD8α transmembrane domain, and an IL-2Rγ intracellular signaling domain.

In certain embodiments, a first polypeptide comprises a multimerization domain comprising an FRB polypeptide or variant thereof, a CD4 or CD8α transmembrane domain, and an IL-7Rα intracellular signaling domain; and a second polypeptide comprises a multimerization domain comprising an FKBP polypeptide or variant thereof, a CD4 or CD8α transmembrane domain, and an IL-2Rγ intracellular signaling domain.

In some embodiments, the bridging factor is AP21967, sirolimus, everolimus, novolimus, pimecrolimus, ridaforolimus, tacrolimus, temsirolimus, umirolimus, or zotarolimus.

In particular embodiments, the FRB polypeptide is FRB T2098L; the FKBP polypeptide is FKBP12; and the bridging factor is AP21967.

In particular embodiments, the FRB polypeptide is FRB; the FKBP polypeptide is FKBP12; and the bridging factor is rapamycin, temsirolimus or everolimus.

4. IL-15 Daric Immune Receptor

Interleukin-15 (IL-15) is a cytokine that promotes T cell function and activity by, in part, improving T cell precursor survival and proliferation. IL-15 binds with high affinity to IL-15Rα (also known as CD215), which then associates with a complex comprising IL-2Rβ (also known as IL-15Rβ and CD122) and IL-2Rγ (also known as CD132 and γc), expressed either on the same cell (cis-presentation) or on a different cell (trans-presentation). IL-15 signaling activates the JAK/STAT, PI-3K, and Src kinase pathways and results in transcription of anti-apoptotic genes and genes that promote proliferation of T cell precursors.

In various embodiments, one or more immune effector cells, including immune effector cells expressing an engineered antigen receptor, are modified by introducing one or more polynucleotides or vectors encoding an IL-15 DARIC immune receptor, and optionally, a polynucleotide or vector encoding an IL-15Rα polypeptide. In various embodiments, one or more immune effector cells are modified by introducing one or more polynucleotides or vectors encoding an IL-15 DARIC immune receptor and an engineered antigen receptor, and optionally, a polynucleotide or vector encoding an IL-15Rα polypeptide.

In particular embodiments, the IL-15 DARIC immune receptor transduces an IL-15-mediated immunostimulatory signal upon exposure to a bridging factor. In particular embodiments an IL-15 DARIC immune receptor contemplated herein comprises: a first multimerization domain, a transmembrane domain, and an IL-2Rβ intracellular signaling domain; a polypeptide cleavage signal; and a second multimerization domain, a transmembrane domain, and an IL-2Rγ intracellular signaling domain. In particular embodiments an IL-15 DARIC immune receptor contemplated herein comprises: a first multimerization domain, a transmembrane domain, and an IL-2Rγ intracellular signaling domain; a polypeptide cleavage signal; and a second multimerization domain, a transmembrane domain, and an IL-2Rβ intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a *Thosea asigna* virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

In particular embodiments, the IL-15 DARIC immune receptor is a complex of polypeptides comprising a first polypeptide comprising a first multimerization domain, a first transmembrane domain, and an IL-2Rβ intracellular signaling domain; and a polypeptide comprising a second multimerization domain, a second transmembrane domain, and an IL-2R$_\gamma$ intracellular signaling domain. In particular embodiments, an IL-15 immune receptor is a complex of polypeptides comprising a first polypeptide comprising a first multimerization domain, a first transmembrane domain, and an IL-2Rγ intracellular signaling domain; and a polypeptide comprising a second multimerization domain, a second transmembrane domain, and an IL-2Rβ intracellular signaling domain.

In particular embodiments, the first and second transmembrane domains are selected from the group consisting of: CD4, CD5, CD8α, CD9, CD 16, CD22, CD27, CD28, CD33, CD3γ, CD45, CD64, CD71, CD80, CD86, CD 134, CD137, CD152, CD 154, AMN, and PD1.

In one embodiment, the first and second multimerization domains are the same.

In certain embodiments, an IL-15 DARIC immune receptor comprises a first or second multimerization domain selected from a pair selected from FKBP and FRB, FKBP and calcineurin, FKBP and cyclophilin, FKBP and bacterial DHFR, calcineurin and cyclophilin, PYL1 and ABI1, or GIB1 and GAI, or variants thereof.

In certain embodiments, a first polypeptide comprises a multimerization domain comprising an FKBP polypeptide or variant thereof, a CD4 or CD8α transmembrane domain, and an IL-2Rβ intracellular signaling domain; and a second polypeptide comprises a multimerization domain comprising an FRB polypeptide or variant thereof, a CD4 or CD8α transmembrane domain, and an IL-2Rγ intracellular signaling domain.

In certain embodiments, a first polypeptide comprises a multimerization domain comprising an FRB polypeptide or variant thereof, a CD4 or CD8α transmembrane domain, and an IL-2Rβ intracellular signaling domain; and a second polypeptide comprises a multimerization domain comprising an FKBP polypeptide or variant thereof, a CD4 or CD8α transmembrane domain, and an IL-2Rγ intracellular signaling domain.

In some embodiments, the bridging factor is AP21967, sirolimus, everolimus, novolimus, pimecrolimus, ridaforolimus, tacrolimus, temsirolimus, umirolimus, or zotarolimus.

In particular embodiments, the FRB polypeptide is FRB T2098L; the FKBP polypeptide is FKBP12; and the bridging factor is AP21967.

In particular embodiments, the FRB polypeptide is FRB; the FKBP polypeptide is FKBP12; and the bridging factor is rapamycin, temsirolimus or everolimus.

5. IL-21 Daric Immune Receptor

Interleukin-21 (IL-21) is a cytokine that promotes T cell function and activity by, in part, improving T cell precursor survival and proliferation. IL-21 binds to interleukin 21 receptor (IL-21R, also known as CD360) and IL-2Rγ (also known as CD132 and γc). IL-21 signaling activates the JAK/STAT, PI-3K, and Src kinase pathways and results in transcription of anti-apoptotic genes and genes that promote proliferation of T cell precursors.

In various embodiments, one or more immune effector cells, including immune effector cells expressing an engineered antigen receptor, are modified by introducing one or more polynucleotides or vectors encoding an IL-21 DARIC immune receptor. In various embodiments, one or more immune effector cells are modified by introducing one or more polynucleotides or vectors encoding an IL-21 DARIC immune receptor and an engineered antigen receptor.

In particular embodiments, the IL-21 DARIC immune receptor transduces an IL-21-mediated immunostimulatory signal upon exposure to a bridging factor. In particular embodiments an IL-21 DARIC immune receptor contemplated herein comprises: a first multimerization domain, a transmembrane domain, and an IL-21R intracellular signaling domain; a polypeptide cleavage signal; and a second multimerization domain, a transmembrane domain, and an IL-2Rγ intracellular signaling domain. In particular embodiments an IL-21 DARIC immune receptor contemplated herein comprises: a first multimerization domain, a transmembrane domain, and an IL-2Rγ intracellular signaling domain; a polypeptide cleavage signal; and a second multimerization domain, a transmembrane domain, and an IL-21R intracellular signaling domain.

In particular embodiments, the polypeptide cleavage signal is a viral self-cleaving polypeptide; more preferably a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a *Thosea asigna* virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

In particular embodiments, the IL-21 DARIC immune receptor is a complex of polypeptides comprising a first polypeptide comprising a first multimerization domain, a first transmembrane domain, and an IL-21R intracellular signaling domain; and a polypeptide comprising a second multimerization domain, a second transmembrane domain, and an IL-2Rγ intracellular signaling domain. In particular embodiments, an IL-21 immune receptor is a complex of polypeptides comprising a first polypeptide comprising a first multimerization domain, a first transmembrane domain, and an IL-2Rγ intracellular signaling domain; and a polypeptide comprising a second multimerization domain, a second transmembrane domain, and an IL-21R intracellular signaling domain.

In particular embodiments, the first and second transmembrane domains are selected from the group consisting of: CD4, CD5, CD8α, CD9, CD 16, CD22, CD27, CD28, CD33, CD3γ, CD45, CD64, CD71, CD80, CD86, CD 134, CD137, CD152, CD 154, AMN, and PD1.

In one embodiment, the first and second multimerization domains are the same.

In certain embodiments, an IL-21 DARIC immune receptor comprises a first or second multimerization domain selected from a pair selected from FKBP and FRB, FKBP and calcineurin, FKBP and cyclophilin, FKBP and bacterial DHFR, calcineurin and cyclophilin, PYL1 and ABI1, or GIB1 and GAI, or variants thereof.

In certain embodiments, a first polypeptide comprises a multimerization domain comprising an FKBP polypeptide or variant thereof, a CD4 or CD8α transmembrane domain, and an IL-21R intracellular signaling domain; and a second polypeptide comprises a multimerization domain comprising an FRB polypeptide or variant thereof, a CD4 or CD8α transmembrane domain, and an IL-2Rγ intracellular signaling domain.

In certain embodiments, a first polypeptide comprises a multimerization domain comprising an FRB polypeptide or variant thereof, a CD4 or CD8α transmembrane domain, and an IL-21R intracellular signaling domain; and a second polypeptide comprises a multimerization domain comprising an FKBP polypeptide or variant thereof, a CD4 or CD8α transmembrane domain, and an IL-12Rγ intracellular signaling domain.

In some embodiments, the bridging factor is AP21967, sirolimus, everolimus, novolimus, pimecrolimus, ridaforolimus, tacrolimus, temsirolimus, umirolimus, or zotarolimus.

In particular embodiments, the FRB polypeptide is FRB T2098L; the FKBP polypeptide is FKBP12; and the bridging factor is AP21967.

In particular embodiments, the FRB polypeptide is FRB; the FKBP polypeptide is FKBP12; and the bridging factor is rapamycin, temsirolimus or everolimus.

6. IL-1 Daric Immune Receptor

Interleukin-1 (IL-1) is a cytokine that promotes T cell function and activity by, in part, increasing IFNγ expression, increasing T cell proliferation, and potentiating protecting against activation induced cell death (AICD). IL-1 binds interleukin 1 receptor 1, (IL-1R1, also known as CD121a) and interleukin 1 receptor accessory protein (IL-1RAP).

IL-1 signaling through IL-1R1 and IL-1RAP results in activation through the MyD88 adaptor protein and IRAK4 phosphorylation. Phosphorylation of IRAK4 and subsequent phosphorylation of IRAK1/2 ultimately leads to activation of NF-kappa B and AP-1 transcription factors to increase IFNγ expression and increase sensitivity to IL-12. The transcriptional program induced by IL-1 also increases T cell proliferation and protects against AICD.

In various embodiments, one or more immune effector cells, including immune effector cells expressing an engineered antigen receptor, are modified by introducing one or more polynucleotides or vectors encoding an IL-1 DARIC immune receptor. In various embodiments, one or more immune effector cells are modified by introducing one or more polynucleotides or vectors encoding an IL-1 DARIC immune receptor and an engineered antigen receptor.

In particular embodiments, the IL-1 DARIC immune receptor transduces an IL-1-mediated immunostimulatory signal upon exposure to a bridging factor. In particular embodiments an IL-1 DARIC immune receptor contemplated herein comprises: a first multimerization domain, a transmembrane domain, and an IL-1RAP intracellular signaling domain; a polypeptide cleavage signal; and a second multimerization domain, a transmembrane domain, and an IL-1R1 intracellular signaling domain. In particular embodiments an IL-1 DARIC immune receptor contemplated herein comprises: a first multimerization domain, a transmembrane domain, and an IL-1R1 intracellular signaling domain; a polypeptide cleavage signal; and a second multimerization domain, a transmembrane domain, and an IL-1RAP intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a *Thosea asigna* virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

In particular embodiments, the IL-1 DARIC immune receptor is a complex of polypeptides comprising a first polypeptide comprising a first multimerization domain, a first transmembrane domain, and an IL-1RAP intracellular signaling domain; and a polypeptide comprising a second multimerization domain, a second transmembrane domain, and an IL-1R1 intracellular signaling domain. In particular embodiments, an IL-1 immune receptor is a complex of polypeptides comprising a first polypeptide comprising a first multimerization domain, a first transmembrane domain, and an IL-1R1 intracellular signaling domain; and a polypeptide comprising a second multimerization domain, a second transmembrane domain, and an IL-1RAP intracellular signaling domain.

In particular embodiments, the first and second transmembrane domains are selected from the group consisting of: CD4, CD5, CD8α, CD9, CD 16, CD22, CD27, CD28, CD33, CD3γ, CD45, CD64, CD71, CD80, CD86, CD 134, CD137, CD152, CD 154, AMN, and PD1.

In one embodiment, the first and second multimerization domains are the same.

In certain embodiments, an IL-1 DARIC immune receptor comprises a first or second multimerization domain selected from a pair selected from FKBP and FRB, FKBP and calcineurin, FKBP and cyclophilin, FKBP and bacterial DHFR, calcineurin and cyclophilin, PYL1 and ABI1, or GIB1 and GAI, or variants thereof.

In certain embodiments, a first polypeptide comprises a multimerization domain comprising an FKBP polypeptide or variant thereof, a CD4 or CD8α transmembrane domain, and an IL-1RAP intracellular signaling domain; and a second polypeptide comprises a multimerization domain comprising an FRB polypeptide or variant thereof, a CD4 or CD8α transmembrane domain, and an IL-1R1 intracellular signaling domain.

In certain embodiments, a first polypeptide comprises a multimerization domain comprising an FRB polypeptide or variant thereof, a CD4 or CD8α transmembrane domain, and an IL-1RAP intracellular signaling domain; and a second polypeptide comprises a multimerization domain comprising an FKBP polypeptide or variant thereof, a CD4 or CD8α transmembrane domain, and an IL-1R1 intracellular signaling domain.

In some embodiments, the bridging factor is AP21967, sirolimus, everolimus, novolimus, pimecrolimus, ridaforolimus, tacrolimus, temsirolimus, umirolimus, or zotarolimus.

In particular embodiments, the FRB polypeptide is FRB T2098L; the FKBP polypeptide is FKBP12; and the bridging factor is AP21967.

In particular embodiments, the FRB polypeptide is FRB; the FKBP polypeptide is FKBP12; and the bridging factor is rapamycin, temsirolimus or everolimus.

7. TLR DARIC Immune Receptor

Toll like receptors (TLR1 through TLR10) are pattern recognition receptors that detect invading pathogens and activate the innate and adaptive immune responses. Activation of TLRs by various ligands leads to induction of a pro-inflammatory transcriptional program and expression of multiple inflammatory cytokines.

TLR signaling occurs via homodimerization of TLR signaling domains leading to activation through the MyD88 adaptor protein and IRAK4 phosphorylation. Phosphorylation of IRAK4 and subsequent phosphorylation of IRAK1/2 ultimately leads to activation of NF-kappa B and AP-1 transcription factors to increase inflammatory cytokine production and induce proliferation. TLR activation can also lead to the activation of IRF3 and IRF7 transcription factors.

In various embodiments, one or more immune effector cells, including immune effector cells expressing an engineered antigen receptor, are modified by introducing one or more polynucleotides or vectors encoding a TLR DARIC immune receptor. In various embodiments, one or more immune effector cells are modified by introducing one or more polynucleotides or vectors encoding a TLR DARIC immune receptor and an engineered antigen receptor.

In particular embodiments, the TLR DARIC immune receptor transduces a TLR mediated immunostimulatory signal upon exposure to a bridging factor. In particular embodiments TLR DARIC immune receptor contemplated herein comprises: a first multimerization domain, a transmembrane domain, and a TLR intracellular signaling domain; a polypeptide cleavage signal; and a second multimerization domain, a transmembrane domain, and an identical TLR intracellular signaling domain. In particular embodiments a TLR DARIC immune receptor contemplated herein comprises: a first multimerization domain, a transmembrane domain, and a TLR intracellular signaling domain; a polypeptide cleavage signal; and a second multimerization domain, a transmembrane domain, and an identical TLR intracellular signaling domain.

In particular embodiments, the polypeptide cleavage signal is a viral self-cleaving polypeptide; more preferably, a viral self-cleaving 2A polypeptide; and more preferably a viral self-cleaving polypeptide selected from the group consisting of: a foot-and-mouth disease virus (FMDV) (F2A) peptide, an equine rhinitis A virus (ERAV) (E2A) peptide, a *Thosea asigna* virus (TaV) (T2A) peptide, a porcine teschovirus-1 (PTV-1) (P2A) peptide, a Theilovirus 2A peptide, and an encephalomyocarditis virus 2A peptide. In one embodiment, the polypeptide cleavage signal is a P2A or T2A viral self-cleaving polypeptide.

In particular embodiments, the TLR DARIC immune receptor is a complex of polypeptides comprising a first polypeptide comprising a first multimerization domain, a first transmembrane domain, and a TLR intracellular signaling domain; and a polypeptide comprising a second multimerization domain, a second transmembrane domain, and an identical TLR intracellular signaling domain. In particular embodiments, a TLR immune receptor is a complex of polypeptides comprising a first polypeptide comprising a first multimerization domain, a first transmembrane domain, and a TLR intracellular signaling domain; and a polypeptide comprising a second multimerization domain, a second transmembrane domain, and an identical TLR intracellular signaling domain.

In preferred embodiments, the TLR intracellular signaling domain is isolated from TLR1, TLR2, TLR3, TLR4, TLR5, TLR6, TLR7, TLR8, TLR9, or TLR10.

In particular embodiments, the first and second transmembrane domains are selected from the group consisting of: CD4, CD5, CD8α, CD9, CD 16, CD22, CD27, CD28, CD33, CD3γ, CD45, CD64, CD71, CD80, CD86, CD 134, CD137, CD152, CD 154, AMN, and PD1.

In one embodiment, the first and second multimerization domains are the same.

In certain embodiments, a TLR DARIC immune receptor comprises a first or second multimerization domain selected from a pair selected from FKBP and FRB, FKBP and calcineurin, FKBP and cyclophilin, FKBP and bacterial DHFR, calcineurin and cyclophilin, PYL1 and ABI1, or GIB1 and GAI, or variants thereof.

In certain embodiments, a first polypeptide comprises a multimerization domain comprising an FKBP polypeptide or variant thereof, a CD4 or CD8α transmembrane domain, and a TLR intracellular signaling domain; and a second polypeptide comprises a multimerization domain comprising an FRB polypeptide or variant thereof, a CD4 or CD8α transmembrane domain, and an identical TLR intracellular signaling domain.

In certain embodiments, a first polypeptide comprises a multimerization domain comprising an FRB polypeptide or variant thereof, a CD4 or CD8α transmembrane domain, and a TLR intracellular signaling domain; and a second polypeptide comprises a multimerization domain comprising an FKBP polypeptide or variant thereof, a CD4 or CD8α transmembrane domain, and an identical TLR intracellular signaling domain.

In some embodiments, the bridging factor is AP21967, sirolimus, everolimus, novolimus, pimecrolimus, ridaforolimus, tacrolimus, temsirolimus, umirolimus, or zotarolimus.

In particular embodiments, the FRB polypeptide is FRB T2098L; the FKBP polypeptide is FKBP12; and the bridging factor is AP21967.

In particular embodiments, the FRB polypeptide is FRB; the FKBP polypeptide is FKBP12; and the bridging factor is rapamycin, temsirolimus or everolimus.

D. Engineered Antigen Receptors

In particular embodiments, a polypeptide comprises an engineered antigen receptor, a polypeptide cleavage signal and a DARIC immune receptor. In other particular embodiments, a polynucleotide or vector encoding a DARIC immune receptor is introduced into an immune effector cell that comprises an engineered antigen receptor. Without wishing to be bound by any particular theory, it is contemplated in particular embodiments, that any mechanism known in the art may be used to introduce and co-express an engineered antigen receptor and a DARIC immune receptor in the same immune effector cell or population of cells to increase the resistance of the immune effector cells to the TME and potentiate and increase the efficiency, potency, and durability of the immune effector cell response.

In particular embodiments, immune effector cells contemplated herein comprise an engineered antigen receptor and a DARIC immune receptor. In particular embodiments, the engineered antigen receptor is an engineered T cell receptor (TCR), a chimeric antigen receptor (CAR), or a zetakine.

1. Engineered TCRs

In particular embodiments, immune effector cells contemplated herein comprise an engineered TCR and a DARIC immune receptor. In one embodiment, T cells are engineered by introducing a polynucleotide or vector encoding an engineered TCR and a DARIC immune receptor separated by one or more polypeptide cleavage signals. In one embodiment, T cells are engineered by introducing a polynucleotide or vector encoding an engineered TCR and a polynucleotide or vector encoding a DARIC immune receptor. In one embodiment, T cells are engineered to express an engineered TCR are further engineered by introducing a polynucleotide or vector encoding a DARIC immune receptor.

Naturally occurring T cell receptors comprise two subunits, an alpha chain and a beta chain subunit, each of which is a unique protein produced by recombination event in each T cell's genome. Libraries of TCRs may be screened for their selectivity to particular target antigens. In this manner, natural TCRs, which have a high-avidity and reactivity toward target antigens may be selected, cloned, and subsequently introduced into a population of T cells used for adoptive immunotherapy.

In one embodiment, T cells are modified by introducing a TCR subunit has the ability to form TCRs that confer specificity to T cells for tumor cells expressing a target antigen. In particular embodiments, the subunits have one or more amino acid substitutions, deletions, insertions, or modifications compared to the naturally occurring subunit, so long as the subunits retain the ability to form TCRs and confer upon transfected T cells the ability to home to target cells and participate in immunologically-relevant cytokine signaling. The engineered TCRs preferably also bind target cells displaying the relevant tumor-associated peptide with high avidity, and optionally mediate efficient killing of target cells presenting the relevant peptide in vivo.

The nucleic acids encoding engineered TCRs are preferably isolated from their natural context in a (naturally-occurring) chromosome of a T cell and can be incorporated into suitable vectors as described elsewhere herein. Both the nucleic acids and the vectors comprising them can be transferred into a cell, preferably a T cell in particular embodiments. The modified T cells are then able to express one or more chains of a TCR encoded by the transduced nucleic acid or nucleic acids. In preferred embodiments, the engineered TCR is an exogenous TCR because it is introduced into T cells that do not normally express the particular TCR. The essential aspect of the engineered TCRs is that it has high avidity for a tumor antigen presented by a major histocompatibility complex (MHC) or similar immunological component. In contrast to engineered TCRs, CARs are engineered to bind target antigens in an MHC independent manner.

The TCR can be expressed with additional polypeptides attached to the amino-terminal or carboxyl-terminal portion of the alpha chain or beta chain of a TCR so long as the attached additional polypeptide does not interfere with the ability of the alpha chain or beta chain to form a functional T cell receptor and the MHC dependent antigen recognition.

Antigens that are recognized by the engineered TCRs contemplated in particular embodiments include, but are not limited to cancer antigens, including antigens on both hematological cancers and solid tumors. Illustrative antigens include, but are not limited to alpha folate receptor, alpha folate receptor, 5T4, αvβ6 integrin, BCMA, B7-H3, B7-H6, CAIX, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, VEGFR2, and WT-1.

2. Chimeric Antigen Receptors

In various embodiments, immune effector cells express CARs that redirect cytotoxicity toward tumor cells. CARs are molecules that combine antibody-based specificity for a target antigen (e.g., tumor antigen) with a T cell receptor-activating intracellular domain to generate a chimeric protein that exhibits a specific anti-tumor cellular immune activity. As used herein, the term, "chimeric," describes being composed of parts of different proteins or DNAs from different origins.

In particular embodiments, immune effector cells contemplated herein comprise CAR and a DARIC immune receptor. In one embodiment, T cells are engineered by introducing a polynucleotide or vector encoding a CAR and a DARIC immune receptor separated by one or more polypeptide cleavage signals. In one embodiment, T cells are engineered by introducing a polynucleotide or vector encoding a CAR and a polynucleotide or vector encoding a DARIC immune receptor. In one embodiment, T cells are engineered to express a CAR are further engineered by introducing a polynucleotide or vector encoding a DARIC immune receptor.

In various embodiments, a CAR comprises an extracellular domain that binds to a specific target antigen (also referred to as a binding domain or antigen-specific binding domain), a transmembrane domain and an intracellular signaling domain. The main characteristic of CARs are their ability to redirect immune effector cell specificity, thereby triggering proliferation, cytokine production, phagocytosis or production of molecules that can mediate cell death of the target antigen expressing cell in a major histocompatibility (MHC) independent manner, exploiting the cell specific targeting abilities of monoclonal antibodies, soluble ligands or cell specific coreceptors.

In particular embodiments, CARs comprise an extracellular binding domain that specifically binds to a target polypeptide. A binding domain includes any naturally occurring, synthetic, semi-synthetic, or recombinantly produced binding partner for a biological molecule of interest.

In particular embodiments, the extracellular binding domain comprises an antibody or antigen binding fragment thereof.

In one preferred embodiment, the binding domain is an scFv.

In another preferred embodiment, the binding domain is a camelid antibody.

In particular embodiments, the CAR comprises an extracellular domain that binds an antigen selected from the group consisting of: alpha folate receptor, 5T4, αvβ6 integrin, BCMA, B7-H3, B7-H6, CAIX, CD16, CD19, CD20, CD22, CD30, CD33, CD44, CD44v6, CD44v7/8, CD70, CD79a, CD79b, CD123, CD138, CD171, CEA, CSPG4, EGFR, EGFR family including ErbB2 (HER2), EGFRvIII, EGP2, EGP40, EPCAM, EphA2, EpCAM, FAP, fetal AchR, FRα, GD2, GD3, Glypican-3 (GPC3), HLA-A1+MAGE1, HLA-A2+MAGE1, HLA-A3+MAGE1, HLA-A1+NY-ESO-1, HLA-A2+NY-ESO-1, HLA-A3+NY-ESO-1, IL-11Rα, IL-13Rα2, Lambda, Lewis-Y, Kappa, Mesothelin, Muc1, Muc16, NCAM, NKG2D Ligands, NY-ESO-1, PRAME, PSCA, PSMA, ROR1, SSX, Survivin, TAG72, TEMs, VEGFR2, and WT-1.

In particular embodiments, the CARs comprise an extracellular binding domain, e.g., antibody or antigen binding fragment thereof that binds an antigen, wherein the antigen is an MHC-peptide complex, such as a class I MHC-peptide complex or a class II MHC-peptide complex.

In one embodiment, the spacer domain comprises the CH2 and CH3 of IgG1, IgG4, or IgD.

Illustrative hinge domains suitable for use in the CARs described herein include the hinge region derived from the extracellular regions of type 1 membrane proteins such as CD8α, and CD4, which may be wild-type hinge regions from these molecules or may be altered. In another embodiment, the hinge domain comprises a CD8α hinge region.

In one embodiment, the hinge is a PD-1 hinge or CD152 hinge.

The transmembrane domain (TM) of the CAR fuses the extracellular binding portion and intracellular signaling domain and anchors the CAR to the plasma membrane of the immune effector cell. The TM domain may be derived either from a natural, synthetic, semi-synthetic, or recombinant source.

Illustrative TM domains may be derived from (i.e., comprise at least the transmembrane region(s) of the alpha, beta, gamma, or delta chain of the T-cell receptor, CD3δ, CD3ε, CD3γ, CD3ζ, CD4, CD5, CD8α, CD9, CD 16, CD22, CD27, CD28, CD33, CD3γ, CD45, CD64, CD80, CD86, CD 134, CD137, CD152, CD154, AMN, and PD-1.

In one embodiment, a CAR comprises a TM domain derived from CD8a. In another embodiment, a CAR contemplated herein comprises a TM domain derived from CD8α and a short oligo- or polypeptide linker, preferably between 1, 2, 3, 4, 5, 6, 7, 8, 9, or 10 amino acids in length that links the TM domain and the intracellular signaling domain of the CAR. A glycine-serine linker provides a particularly suitable linker.

In preferred embodiments, a CAR comprises an intracellular signaling domain that comprises one or more "co-stimulatory signaling domains" and a "primary signaling domain."

Primary signaling domains that act in a stimulatory manner may contain signaling motifs which are known as immunoreceptor tyrosine-based activation motifs or ITAMs.

Illustrative examples of ITAM containing primary signaling domains suitable for use in CARs contemplated in particular embodiments include those derived from FcRγ, FcRβ, CD3γ, CD3δ, CD3ε, CD3ζ, CD22, CD79a, CD79b, and CD66d. In particular preferred embodiments, a CAR comprises a CD3ζ primary signaling domain and one or more co-stimulatory signaling domains. The intracellular primary signaling and co-stimulatory signaling domains may be linked in any order in tandem to the carboxyl terminus of the transmembrane domain.

In particular embodiments, a CAR comprises one or more co-stimulatory signaling domains to enhance the efficacy and expansion of T cells expressing CAR receptors.

Illustrative examples of such co-stimulatory molecules suitable for use in CARs contemplated in particular embodiments include TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70. In one embodiment, a CAR comprises one or more co-stimulatory signaling domains selected from the group consisting of CD28, CD137, and CD134, and a CD3ζ primary signaling domain.

In various embodiments, the CAR comprises: an extracellular domain that binds an antigen selected from the group consisting of: BCMA, CD19, CSPG4, PSCA, ROR1, and TAG72; a transmembrane domain isolated from a polypeptide selected from the group consisting of: CD4, CD8α, CD154, and PD-1; one or more intracellular co-stimulatory signaling domains isolated from a polypeptide selected from the group consisting of: CD28, CD134, and CD137; and a signaling domain isolated from a polypeptide selected from the group consisting of: FcRγ, FcRβ, CD3γ, CD3δ, CD3ε, CD3ζ, CD22, CD79a, CD79b, and CD66d.

3. Zetakines

In various embodiments, immune effector cells comprise chimeric cytokine receptor that redirect cytotoxicity toward tumor cells. Zetakines are chimeric transmembrane immunoreceptors that comprise an extracellular domain comprising a soluble receptor ligand linked to a support region capable of tethering the extracellular domain to a cell surface, a transmembrane region and an intracellular signaling domain. Zetakines, when expressed on the surface of T lymphocytes, direct T cell activity to those cells expressing a receptor for which the soluble receptor ligand is specific. Zetakine chimeric immunoreceptors redirect the antigen specificity of T cells, with application to treatment of a variety of cancers, particularly via the autocrine/paracrine cytokine systems utilized by human malignancy.

In particular embodiments, immune effector cells contemplated herein comprise one or more chains of a zetakine receptor and a DARIC immune receptor. In one embodiment, T cells are engineered by introducing a polynucleotide or vector encoding one or more chains of a zetakine receptor and a DARIC immune receptor separated by one or more polypeptide cleavage signals. In one embodiment, T cells are engineered by introducing a polynucleotide or vector encoding one or more chains of a zetakine receptor and a polynucleotide or vector encoding a DARIC immune receptor. In one embodiment, T cells are engineered to express one or more chains of a zetakine receptor are further engineered by introducing a polynucleotide or vector encoding a DARIC immune receptor.

In particular embodiments, the zetakine comprises an immunosuppressive cytokine or cytokine receptor binding variant thereof, a linker, a transmembrane domain, and an intracellular signaling domain.

In particular embodiments, the cytokine or cytokine receptor binding variant thereof is selected from the group consisting of: interleukin-4 (IL-4), interleukin-6 (IL-6), interleukin-8 (IL-8), interleukin-10 (IL-10), and interleukin-13 (IL-13).

In certain embodiments, the linker comprises a CH2CH3 domain, hinge domain, or the like. In one embodiment, a linker comprises the CH2 and CH3 domains of IgG1, IgG4, or IgD. In one embodiment, a linker comprises a CD8α or CD4 hinge domain.

In particular embodiments, the transmembrane domain is selected from the group consisting of: the alpha or beta chain of the T-cell receptor, CD3δ, CD3ε, CD3γ, CD3ζ, CD4, CD5, CD8α, CD9, CD 16, CD22, CD27, CD28, CD33, CD3γ, CD45, CD64, CD80, CD86, CD 134, CD137, CD152, CD154, AMN, and PD-1.

In particular embodiments, the intracellular signaling domain is selected from the group consisting of: an ITAM containing primary signaling domain and/or a co-stimulatory domain.

In particular embodiments, the intracellular signaling domain is selected from the group consisting of: FcRγ, FcRβ, CD3γ, CD3δ, CD3ε, CD3ζ, CD22, CD79a, CD79b, and CD66d.

In particular embodiments, the intracellular signaling domain is selected from the group consisting of: TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70.

In one embodiment, a chimeric cytokine receptor comprises one or more co-stimulatory signaling domains selected from the group consisting of CD28, CD137, and CD134, and a CD3ζ primary signaling domain.

E. Polypeptides

Various polypeptides are contemplated herein, including, but not limited to, DARIC immune receptors, engineered TCRs, CARs, zetakines, fusion proteins comprising the foregoing polypeptides and fragments thereof. In preferred embodiments, a polypeptide comprises an amino acid sequence set forth in any one of SEQ ID NOs: 1-6. "Polypeptide," "peptide" and "protein" are used interchangeably, unless specified to the contrary, and according to conventional meaning, i.e., as a sequence of amino acids. In one embodiment, a "polypeptide" includes fusion polypeptides and other variants. Polypeptides can be prepared using any of a variety of well-known recombinant and/or synthetic techniques. Polypeptides are not limited to a specific length, e.g., they may comprise a full-length protein sequence, a fragment of a full-length protein, or a fusion protein, and may include post-translational modifications of the polypeptide, for example, glycosylations, acetylations, phosphorylations and the like, as well as other modifications known in the art, both naturally occurring and non-naturally occurring. In particular preferred embodiments, fusion polypeptides, polypeptides, fragments and other variants thereof are prepared, obtained, or isolated from one or more human polypeptides.

An "isolated peptide" or an "isolated polypeptide" and the like, as used herein, refer to in vitro isolation and/or purification of a peptide or polypeptide molecule from a cellular environment, and from association with other components of the cell, i.e., it is not significantly associated with in vivo substances. In particular embodiments, an isolated polypeptide is a synthetic polypeptide, a semi-synthetic polypeptide, or a polypeptide obtained or derived from a recombinant source.

Polypeptides include "polypeptide variants." Polypeptide variants may differ from a naturally occurring polypeptide in one or more substitutions, deletions, additions and/or insertions. Such variants may be naturally occurring or may be synthetically generated, for example, by modifying one or more of the above polypeptide sequences. For example, in particular embodiments, it may be desirable to improve the binding affinity and/or other biological properties of a polypeptide by introducing one or more substitutions, deletions, additions and/or insertions the polypeptide. In particular embodiments, polypeptides include polypeptides having at least about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% amino acid identity to any of the reference sequences contemplated herein, typically where the variant maintains at least one biological activity of the reference sequence. In particular embodiments, the biological activity is binding affinity. In particular embodiments, the biological activity is enzymatic activity.

In certain embodiments, a polypeptide complex comprises (i) a first polypeptide, e.g., first fusion polypeptide, having a first multimerization domain and (ii) second polypeptide, e.g., second fusion polypeptide, having a second multimerization domain that is not the same as the first multimerization domain, wherein the first and second multimerization domains substantially contribute to or efficiently promote formation of the polypeptide complex in the presence of a bridging factor. The interaction(s) between the first and second multimerization domains substantially contributes to or efficiently promotes the multimerization of the first and second fusion polypeptides if there is a statistically significant reduction in the association between the first and second fusion polypeptides in the absence of the first multimerization domain, the second multimerization domain, or the bridging factor. In certain embodiments, when the first and second fusion polypeptides are co-expressed, at least about 60%, for instance, at least about 60% to about 70%, at least about 70% to about 80%, at least about 80% to about 90%, 91%, 92%, 93%, 94%, 95%, 96%, 97%, 98%, 99%, or 100%, and at least about 90% to about 92%, 93%, 94%, 95%, 96%, 97%, 98%, or 99% of the first and second single chain polypeptides form multimers with each other in the presence of a bridging factor.

Polypeptides variants include biologically active "polypeptide fragments." Illustrative examples of biologically active polypeptide fragments include binding domains, signaling domains, and the like. As used herein, the term "biologically active fragment" or "minimal biologically active fragment" refers to a polypeptide fragment that retains at least 100%, at least 90%, at least 80%, at least 70%, at least 60%, at least 50%, at least 40%, at least 30%, at least 20%, at least 10%, or at least 5% of the naturally occurring polypeptide activity. In certain embodiments, a polypeptide fragment can comprise an amino acid chain at least 5 to about 1700 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, 450, 500, 550, 600, 650, 700, 750, 800, 850, 900, 950, 1000, 1100, 1200, 1300, 1400, 1500, 1600, 1700 or more amino acids long.

In particular embodiments, the polypeptides set forth herein may comprise one or more amino acids denoted as "X." "X" if present in an amino acid SEQ ID NO, refers to any one or more amino acids. In particular embodiments, SEQ ID NOs denoting a fusion protein comprise a sequence of continuous X residues that cumulatively represent any scFv.

As noted above, polypeptides may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad. Sci. USA*. 82: 488-492), Kunkel et al., (1987, *Methods in Enzymol*, 154: 367-382), U.S. Pat. No. 4,873,192, Watson, J. D. et al., (*Molecular Biology of the Gene*, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) *Atlas of Protein Sequence and Structure* (*Natl. Biomed. Res. Found.*, Washington, D.C.).

In certain embodiments, a polypeptide variant comprises one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides contemplated in particular embodiments and still obtain a functional molecule that encodes a variant or derivative polypeptide with desirable characteristics. When it is desired to alter the amino acid sequence of a polypeptide to create an equivalent, or even an improved, variant polypeptide, one skilled in the art, for example, can change one or more of the codons of the encoding DNA sequence, e.g., according to Table 1.

TABLE 1

Amino Acid Codons

| Amino Acids | One letter code | Three letter code | Codons | | | | | |
|---|---|---|---|---|---|---|---|---|
| Alanine | A | Ala | GCA | GCC | GCG | | GCU | |
| Cysteine | C | Cys | UGC | | | UGU | | |
| Aspartic acid | D | Asp | GAC | | | GAU | | |
| Glutamic acid | E | Glu | GAA | | | GAG | | |
| Phenylalanine | F | Phe | UUC | | | UUU | | |
| Glycine | G | Gly | GGA | GGC | GGG | | GGU | |
| Histidine | H | His | CAC | | | CAU | | |
| Isoleucine | I | Iso | AUA | AUC | | AUU | | |
| Lysine | K | Lys | AAA | | | AAG | | |
| Leucine | L | Leu | UUA | UUG | CUA | CUC | CUG | CUU |

TABLE 1-continued

Amino Acid Codons

| Amino Acids | One letter code | Three letter code | Codons | | | | | |
|---|---|---|---|---|---|---|---|---|
| Methionine | M | Met | AUG | | | | | |
| Asparagine | N | Asn | AAC | | | AAU | | |
| Proline | P | Pro | CCA | CCC | CCG | | CCU | |
| Glutamine | Q | Gln | CAA | | | CAG | | |
| Arginine | R | Arg | AGA | AGG | CGA | CGC | CGG | CGU |
| Serine | S | Ser | AGC | AGU | UCA | UCC | UCG | UCU |
| Threonine | T | Thr | ACA | ACC | ACG | | ACU | |
| Valine | V | Val | GUA | GUC | GUG | | GUU | |
| Tryptophan | W | Trp | | | UGG | | | |
| Tyrosine | Y | Tyr | UAC | | | UAU | | |

Guidance in determining which amino acid residues can be substituted, inserted, or deleted without abolishing biological activity can be found using computer programs well known in the art, such as DNASTAR, DNA Strider, Geneious, Mac Vector, or Vector NTI software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene*, 4th Edition, 1987, The Benjamin/Cummings Pub. Co., p. 224).

In one embodiment, where expression of two or more polypeptides is desired, the polynucleotide sequences encoding them can be separated by an IRES sequence as disclosed elsewhere herein.

Polypeptides contemplated in particular embodiments include fusion polypeptides. In particular embodiments, fusion polypeptides and polynucleotides encoding fusion polypeptides are provided. Fusion polypeptides and fusion proteins refer to a polypeptide having at least two, three, four, five, six, seven, eight, nine, or ten polypeptide segments. In preferred embodiments, a fusion polypeptide is a DARIC immune receptor. In other preferred embodiments, the fusion polypeptide comprises one or more DARIC immune receptors. In particular preferred embodiments, fusion polypeptides comprise one or more segments, fragments, or domains of one or more human polypeptides.

In another embodiment, two or more polypeptides can be expressed as a fusion protein that comprises one or more self-cleaving polypeptide sequences as disclosed elsewhere herein.

Fusion polypeptides can comprise one or more polypeptide domains or segments including, but are not limited to signal peptides, cell permeable peptide domains (CPP), binding domains, signaling domains, etc., epitope tags (e.g., maltose binding protein ("MBP"), glutathione S transferase (GST), HIS6, MYC, FLAG, V5, VSV-G, and HA), polypeptide linkers, and polypeptide cleavage signals. Fusion polypeptides are typically linked C-terminus to N-terminus, although they can also be linked C-terminus to C-terminus, N-terminus to N-terminus, or N-terminus to C-terminus. In particular embodiments, the polypeptides of the fusion protein can be in any order. Fusion polypeptides or fusion proteins can also include conservatively modified variants, polymorphic variants, alleles, mutants, subsequences, and interspecies homologs, so long as the desired activity of the fusion polypeptide is preserved. Fusion polypeptides may be produced by chemical synthetic methods or by chemical linkage between the two moieties or may generally be prepared using other standard techniques. Ligated DNA sequences comprising the fusion polypeptide are operably linked to suitable transcriptional or translational control elements as disclosed elsewhere herein.

Fusion polypeptides may optionally comprise a linker that can be used to link the one or more polypeptides or domains within a polypeptide. A peptide linker sequence may be employed to separate any two or more polypeptide components by a distance sufficient to ensure that each polypeptide folds into its appropriate secondary and tertiary structures so as to allow the polypeptide domains to exert their desired functions. Such a peptide linker sequence is incorporated into the fusion polypeptide using standard techniques in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos. 4,935,233 and 4,751,180. Linker sequences are not required when a particular fusion polypeptide segment contains non-essential N-terminal amino acid regions that can be used to separate the functional domains and prevent steric interference. Preferred linkers are typically flexible amino acid subsequences which are synthesized as part of a recombinant fusion protein. Linker polypeptides can be between 1 and 200 amino acids in length, between 1 and 100 amino acids in length, or between 1 and 50 amino acids in length, including all integer values in between.

Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. *Traffic*, 5(8); 616-26).

Suitable protease cleavages sites and self-cleaving peptides are known to the skilled person (see, e.g., in Ryan et al., 1997. *J. Gener. Virol.* 78, 699-722; Scymczak et al. (2004) Nature Biotech. 5, 589-594). Exemplary protease cleavage sites include, but are not limited to the cleavage sites of potyvirus NIa proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites are preferred in one embodiment, e.g., EXXYXQ(G/S) (SEQ ID NO: 18), for example, ENLYFQG (SEQ ID NO: 19) and ENLYFQS (SEQ ID NO: 20), wherein X represents any amino acid (cleavage by TEV occurs between Q and G or Q and S).

In particular embodiments, the polypeptide cleavage signal is a viral self-cleaving peptide or ribosomal skipping sequence.

Illustrative examples of ribosomal skipping sequences include but are not limited to: a 2A or 2A-like site, sequence or domain (Donnelly et al., 2001. J. Gen. Virol. 82:1027-1041). In a particular embodiment, the viral 2A peptide is an aphthovirus 2A peptide, a potyvirus 2A peptide, or a cardiovirus 2A peptide.

In one embodiment, the viral 2A peptide is selected from the group consisting of: a foot-and-mouth disease virus (FMDV) (F2A) peptide, an equine rhinitis A virus (ERAV) (E2A) peptide, a *Thosea asigna* virus (TaV) (T2A) peptide, a porcine teschovirus-1 (PTV-1) (P2A) peptide, a Theilovirus 2A peptide, and an encephalomyocarditis virus 2A peptide.

Illustrative examples of 2A sites are provided in Table 2.

TABLE 2

| | |
|---|---|
| SEQ ID NO: 21 | GSGATNFSLLKQAGDVEENPGP |
| SEQ ID NO: 22 | ATNFSLLKQAGDVEENPGP |
| SEQ ID NO: 23 | LLKQAGDVEENPGP |
| SEQ ID NO: 24 | GSGEGRGSLLTCGDVEENPGP |
| SEQ ID NO: 25 | EGRGSLLTCGDVEENPGP |
| SEQ ID NO: 26 | LLTCGDVEENPGP |
| SEQ ID NO: 27 | GSGQCTNYALLKLAGDVESNPGP |
| SEQ ID NO: 28 | QCTNYALLKLAGDVESNPGP |
| SEQ ID NO: 29 | LLKLAGDVESNPGP |
| SEQ ID NO: 30 | GSGVKQTLNFDLLKLAGDVESNPGP |
| SEQ ID NO: 31 | VKQTLNFDLLKLAGDVESNPGP |
| SEQ ID NO: 32 | LLKLAGDVESNPGP |
| SEQ ID NO: 33 | LLNFDLLKLAGDVESNPGP |
| SEQ ID NO: 34 | TLNFDLLKLAGDVESNPGP |
| SEQ ID NO: 35 | LLKLAGDVESNPGP |
| SEQ ID NO: 36 | NFDLLKLAGDVESNPGP |
| SEQ ID NO: 37 | QLLNFDLLKLAGDVESNPGP |
| SEQ ID NO: 38 | APVKQTLNFDLLKLAGDVESNPGP |
| SEQ ID NO: 39 | VTELLYRMKRAETYCPRPLLAIHPTEARHKQKIVAPVKQT |
| SEQ ID NO: 40 | LNFDLLKLAGDVESNPGP |
| SEQ ID NO: 41 | LLAIHPTEARHKQKIVAPVKQTLNFDLLKLAGDVESNPGP |
| SEQ ID NO: 42 | EARHKQKIVAPVKQTLNFDLLKLAGDVESNPGP |

In preferred embodiments, a polypeptide or fusion polypeptide comprises a DARIC immune receptor polypeptide.

F. Polynucleotides

In particular embodiments, polynucleotides encoding DARIC immune receptors, engineered TCRs, CARs, zetakines, fusion proteins comprising the foregoing polypeptides and fragments thereof are provided. As used herein, the terms "polynucleotide" or "nucleic acid" refer to deoxyribonucleic acid (DNA), ribonucleic acid (RNA) and DNA/RNA hybrids. Polynucleotides may be single-stranded or double-stranded and either recombinant, synthetic, or isolated. Polynucleotides include, but are not limited to: pre-messenger RNA (pre-mRNA), messenger RNA (mRNA), RNA, short interfering RNA (siRNA), short hairpin RNA (shRNA), microRNA (miRNA), ribozymes, genomic RNA (gRNA), plus strand RNA (RNA(+)), minus strand RNA (RNA(−)), tracrRNA, crRNA, single guide RNA (sgRNA), synthetic RNA, synthetic mRNA, genomic DNA (gDNA), PCR amplified DNA, complementary DNA (cDNA), synthetic DNA, or recombinant DNA. Polynucleotides refer to a polymeric form of nucleotides of at least 5, at least 10, at least 15, at least 20, at least 25, at least 30, at least 40, at least 50, at least 100, at least 200, at least 300, at least 400, at least 500, at least 1000, at least 5000, at least 10000, or at least 15000 or more nucleotides in length, either ribonucleotides or deoxyribonucleotides or a modified form of either type of nucleotide, as well as all intermediate lengths. It will be readily understood that "intermediate lengths," in this context, means any length between the quoted values, such as 6, 7, 8, 9, etc., 101, 102, 103, etc.; 151, 152, 153, etc.; 201, 202, 203, etc. In particular embodiments, polynucleotides or variants have at least or about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a reference sequence.

In particular embodiments, polynucleotides may be codon-optimized. As used herein, the term "codon-optimized" refers to substituting codons in a polynucleotide encoding a polypeptide in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, (x) systematic variation of codon sets for each amino acid, and/or (xi) isolated removal of spurious translation initiation sites.

As used herein the term "nucleotide" refers to a heterocyclic nitrogenous base in N-glycosidic linkage with a phosphorylated sugar. Nucleotides are understood to include natural bases, and a wide variety of art-recognized modified bases. Such bases are generally located at the 1' position of a nucleotide sugar moiety. Nucleotides generally comprise a base, sugar and a phosphate group. In ribonucleic acid (RNA), the sugar is a ribose, and in deoxyribonucleic acid (DNA) the sugar is a deoxyribose, i.e., a sugar lacking a hydroxyl group that is present in ribose. Exemplary natural nitrogenous bases include the purines, adenosine (A) and guanidine (G), and the pyrimidines, cytidine (C) and thymidine (T) (or in the context of RNA, uracil (U)). The C-1 atom of deoxyribose is bonded to N-1 of a pyrimidine or N-9 of a purine. Nucleotides are usually mono, di- or triphosphates. The nucleotides can be unmodified or modified at the sugar, phosphate and/or base moiety, (also referred to interchangeably as nucleotide analogs, nucleotide derivatives, modified nucleotides, non-natural nucleotides, and non-standard nucleotides; see for example, WO 92/07065 and WO 93/15187). Examples of modified nucleic acid bases are summarized by Limbach et al., (1994, *Nucleic Acids Res.* 22, 2183-2196).

A nucleotide may also be regarded as a phosphate ester of a nucleoside, with esterification occurring on the hydroxyl group attached to C-5 of the sugar. As used herein, the term "nucleoside" refers to a heterocyclic nitrogenous base in N-glycosidic linkage with a sugar. Nucleosides are recognized in the art to include natural bases, and also to include well known modified bases. Such bases are generally located at the 1' position of a nucleoside sugar moiety. Nucleosides generally comprise a base and sugar group. The nucleosides can be unmodified or modified at the sugar, and/or base moiety, (also referred to interchangeably as nucleoside analogs, nucleoside derivatives, modified nucleosides, non-natural nucleosides, or non-standard nucleosides). As also noted above, examples of modified nucleic acid bases are summarized by Limbach et al., (1994, *Nucleic Acids Res.* 22, 2183-2196).

Illustrative examples of polynucleotides include but are not limited to polynucleotides encoding SEQ ID NOs: 1-6.

In various illustrative embodiments, polynucleotides contemplated herein include, but are not limited to polynucleotides encoding DARIC immune receptors, engineered antigen receptors, fusion polypeptides, and expression vectors, viral vectors, and transfer plasmids comprising polynucleotides contemplated herein.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion, substitution, or modification of at least one nucleotide. Accordingly, the terms "polynucleotide variant" and "variant" include polynucleotides in which one or more nucleotides have been added or deleted, or modified, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide.

In one embodiment, a polynucleotide comprises a nucleotide sequence that hybridizes to a target nucleic acid sequence under stringent conditions. To hybridize under "stringent conditions" describes hybridization protocols in which nucleotide sequences at least 60% identical to each other remain hybridized. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% sequence identity to any of the reference sequences described herein, typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, WI, USA) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389. A detailed discussion of sequence analysis can be found in Unit 19.3 of Ausubel et al., *Current Protocols in Molecular Biology*, John Wiley & Sons Inc, 1994-1998, Chapter 15.

As used herein, "isolated polynucleotide" refers to a polynucleotide that has been purified from the sequences which flank it in a naturally-occurring state, e.g., a DNA fragment that has been removed from the sequences that are normally adjacent to the fragment. An "isolated polynucleotide" also refers to a complementary DNA (cDNA), a recombinant DNA, or other polynucleotide that does not exist in nature and that has been made by the hand of man. In particular embodiments, an isolated polynucleotide is a synthetic polynucleotide, a semi-synthetic polynucleotide, or a polynucleotide obtained or derived from a recombinant source.

In various embodiments, a polynucleotide comprises an mRNA encoding a polypeptide contemplated herein. In certain embodiments, the mRNA comprises a cap, one or more nucleotides, and a poly(A) tail.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation. For DNA and mRNA, the 5' to 3' strand is designated the "sense," "plus," or "coding" strand because its sequence is identical to the sequence of the premessenger (premRNA) [except for uracil (U) in RNA, instead of thymine (T) in DNA]. For DNA and mRNA, the complementary 3' to 5' strand which is the strand transcribed by the RNA polymerase is designated as "template," "antisense," "minus," or "non-coding" strand. As used herein, the term "reverse orientation" refers to a 5' to 3' sequence written in the 3' to 5' orientation or a 3' to 5' sequence written in the 5' to 3' orientation.

The terms "complementary" and "complementarity" refer to polynucleotides (i.e., a sequence of nucleotides) related by the base-pairing rules. For example, the complementary strand of the DNA sequence 5' A G T C A T G 3' is 3' T C A G T A C 5'. The latter sequence is often written as the reverse complement with the 5' end on the left and the 3' end on the right, 5' C A T G A C T 3'. A sequence that is equal to its reverse complement is said to be a palindromic sequence. Complementarity can be "partial," in which only some of the nucleic acids' bases are matched according to the base pairing rules. Or, there can be "complete" or "total" complementarity between the nucleic acids.

Moreover, it will be appreciated by those of ordinary skill in the art that, as a result of the degeneracy of the genetic code, there are many nucleotide sequences that encode a polypeptide, or fragment of variant thereof, as described herein. Some of these polynucleotides bear minimal homology to the nucleotide sequence of any native gene. Nonetheless, polynucleotides that vary due to differences in codon usage are specifically contemplated in particular embodiments, for example polynucleotides that are optimized for human and/or primate codon selection. In particular embodiments, the polynucleotides are codon optimized for expression and/or stability. Further, alleles of the genes comprising the polynucleotide sequences provided herein may also be used. Alleles are endogenous genes that are altered as a result of one or more mutations, such as deletions, additions and/or substitutions of nucleotides.

The term "nucleic acid cassette" or "expression cassette" as used herein refers to genetic sequences within the vector which can express an RNA, and subsequently a polypeptide. In one embodiment, the nucleic acid cassette contains a gene(s)-of-interest, e.g., a polynucleotide(s)-of-interest. In another embodiment, the nucleic acid cassette contains one or more expression control sequences, e.g., a promoter, enhancer, poly(A) sequence, and a gene(s)-of-interest, e.g., a polynucleotide(s)-of-interest. Vectors may comprise 1, 2, 3, 4, 5, 6, 7, 8, 9 or 10 or more nucleic acid cassettes. The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end. In a preferred embodiment, the nucleic acid cassette contains the sequence of a therapeutic gene used to treat, prevent, or ameliorate a genetic disorder. The cassette can be removed and inserted into a plasmid or viral vector as a single unit.

Polynucleotides include polynucleotide(s)-of-interest. As used herein, the term "polynucleotide-of-interest" refers to a polynucleotide encoding a polypeptide or fusion polypeptide or a polynucleotide that serves as a template for the transcription of an inhibitory polynucleotide, as contemplated herein.

The polynucleotides contemplated herein, regardless of the length of the coding sequence itself, may be combined with other DNA sequences, such as promoters and/or enhancers, untranslated regions (UTRs), signal sequences, Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, as disclosed elsewhere herein or as known in the art, such that their overall length may vary considerably. It is therefore contemplated that a polynucleotide fragment of almost any length may be employed, with the total length preferably being limited by the ease of preparation and use in the intended recombinant DNA protocol.

Polynucleotides can be prepared, manipulated, expressed and/or delivered using any of a variety of well-established techniques known and available in the art. In order to express a desired polypeptide, a nucleotide sequence encoding the polypeptide, can be inserted into appropriate vector.

Illustrative examples of vectors include, but are not limited to plasmid, autonomously replicating sequences, and transposable elements, e.g., Sleeping Beauty, PiggyBac.

Additional Illustrative examples of vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses.

Illustrative examples of viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40).

Illustrative examples of expression vectors include but are not limited to pClneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells. In particular embodiments, coding sequences of polypeptides disclosed herein can be ligated into such expression vectors for the expression of the polypeptides in mammalian cells.

In particular embodiments, the vector is an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally.

"Expression control sequences," "control elements," or "regulatory sequences" present in an expression vector are those non-translated regions of the vector including but not limited to the origin of replication, selection cassettes, promoters, enhancers, translation initiation signals (Shine Dalgarno sequence or Kozak sequence) introns, a polyadenylation sequence, 5' and 3' untranslated regions, all of which interact with host cellular proteins to carry out transcription and translation. Such elements may vary in their strength and specificity. Depending on the vector system and host utilized, any number of suitable transcription and translation elements, including ubiquitous promoters and inducible promoters may be used.

In particular embodiments, a polynucleotide comprises a vector, including but not limited to expression vectors and viral vectors. A vector may comprise one or more exogenous, endogenous, or heterologous control sequences such as promoters and/or enhancers. An "endogenous control sequence" is one which is naturally linked with a given gene in the genome. An "exogenous control sequence" is one which is placed in juxtaposition to a gene by means of genetic manipulation (i.e., molecular biological techniques) such that transcription of that gene is directed by the linked enhancer/promoter. A "heterologous control sequence" is an exogenous sequence that is from a different species than the cell being genetically manipulated. A "synthetic" control sequence may comprise elements of one more endogenous and/or exogenous sequences, and/or sequences determined in vitro or in silico that provide optimal promoter and/or enhancer activity for the particular therapy.

The term "promoter" as used herein refers to a recognition site of a polynucleotide (DNA or RNA) to which an RNA polymerase binds. An RNA polymerase initiates and transcribes polynucleotides operably linked to the promoter. In particular embodiments, promoters operative in mammalian cells comprise an AT-rich region located approximately 25 to 30 bases upstream from the site where transcription is initiated and/or another sequence found 70 to 80 bases upstream from the start of transcription, a CNCAAT region where N may be any nucleotide.

The term "enhancer" refers to a segment of DNA which contains sequences capable of providing enhanced transcription and in some instances can function independent of their orientation relative to another control sequence. An enhancer can function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide-of-interest, wherein the expression control sequence directs transcription of the nucleic acid corresponding to the second sequence.

As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively.

Illustrative ubiquitous expression control sequences suitable for use in particular embodiments include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., *Nature Biotechnology* 25, 1477-1482 (2007)), a Ubiquitin C promoter (UBC), a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, d1587 rev primer-binding site substituted (MND) U3 promoter (Haas et al. *Journal of Virology.* 2003; 77(17): 9439-9450).

In one embodiment, a vector comprises an MNDU3 promoter.

In one embodiment, a vector comprises an EF1a promoter comprising the first intron of the human EF1a gene.

In one embodiment, a vector comprises an EF1a promoter that lacks the first intron of the human EF1a gene.

In a particular embodiment, it may be desirable to use a cell, cell type, cell lineage or tissue specific expression control sequence to achieve cell type specific, lineage specific, or tissue specific expression of a desired polynucleotide sequence (e.g., to express a particular nucleic acid encoding a polypeptide in only a subset of cell types, cell lineages, or tissues or during specific stages of development).

In a particular embodiment, it may be desirable to express a polynucleotide a T cell specific promoter.

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue specific expression. Certain embodiments provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, *Gene,* 323:67), the cumate inducible gene switch (WO 2002/088346), tetracycline-dependent regulatory systems, etc. Inducer agents include, but are not limited to glucocorticoids, estrogens, mifepristone (RU486), metals, interferons, small molecules, cumate, tetracycline, doxycycline, and variants thereof.

Conditional expression can also be achieved by using a site specific DNA recombinase. According to certain embodiments the vector comprises at least one (typically two) site(s) for recombination mediated by a site specific recombinase. As used herein, the terms "recombinase" or "site specific recombinase" include excisive or integrative proteins, enzymes, co-factors or associated proteins that are involved in recombination reactions involving one or more recombination sites (e.g., two, three, four, five, seven, ten, twelve, fifteen, twenty, thirty, fifty, etc.), which may be wild-type proteins (see Landy, *Current Opinion in Biotechnology* 3:699-707 (1993)), or mutants, derivatives (e.g., fusion proteins containing the recombination protein sequences or fragments thereof), fragments, and variants thereof. Illustrative examples of recombinases suitable for use in particular embodiments include, but are not limited to: Cre, Int, IHF, Xis, Flp, Fis, Hin, Gin, ΦDC31, Cin, Tn3 resolvase, TndX, XerC, XerD, TnpX, Hjc, Gin, SpCCE1, and ParA.

The polynucleotides may comprise one or more recombination sites for any of a wide variety of site specific recombinases. It is to be understood that the target site for a site specific recombinase is in addition to any site(s) required for integration of a vector, e.g., a retroviral vector or lentiviral vector. As used herein, the terms "recombination sequence," "recombination site," or "site specific recombination site" refer to a particular nucleic acid sequence to which a recombinase recognizes and binds.

For example, one recombination site for Cre recombinase is loxP which is a 34 base pair sequence comprising two 13 base pair inverted repeats (serving as the recombinase binding sites) flanking an 8 base pair core sequence (see FIG. 1 of Sauer, B., *Current Opinion in Biotechnology* 5:521-527 (1994)). Other exemplary loxP sites include but are not limited to: lox511 (Hoess et al., 1996; Bethke and Sauer, 1997), lox5171 (Lee and Saito, 1998), lox2272 (Lee and Saito, 1998), m2 (Langer et al., 2002), lox71 (Albert et al., 1995), and lox66 (Albert et al., 1995).

Suitable recognition sites for the FLP recombinase include, but are not limited to: FRT (McLeod, et al., 1996), $F_1$, $F_2$, $F_3$ (Schlake and Bode, 1994), $F_4$, $F_5$ (Schlake and Bode, 1994), FRT(LE) (Senecoff et al., 1988), FRT(RE) (Senecoff et al., 1988).

Other examples of recognition sequences are the attB, attP, attL, and attR sequences, which are recognized by the recombinase enzyme λ Integrase, e.g., phi-c31. The φC31 SSR mediates recombination only between the heterotypic sites attB (34 bp in length) and attP (39 bp in length) (Groth et al., 2000). attB and attP, named for the attachment sites for the phage integrase on the bacterial and phage genomes, respectively, both contain imperfect inverted repeats that are likely bound by φC31 homodimers (Groth et al., 2000). The product sites, attL and attR, are effectively inert to further φC31-mediated recombination (Belteki et al., 2003), making the reaction irreversible. For catalyzing insertions, it has been found that attB-bearing DNA inserts into a genomic attP site more readily than an attP site into a genomic attB site (Thyagarajan et al., 2001; Belteki et al., 2003). Thus, typical strategies position by homologous recombination an attP-bearing "docking site" into a defined locus, which is then partnered with an attB-bearing incoming sequence for insertion.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson et al., 1990. *Trends Biochem Sci* 15(12):477-83) and Jackson and Kaminski. 1995. RNA 1(10):985-1000. Examples of IRES generally employed by those of skill in the art include those described in U.S. Pat. No. 6,692,736. Further examples of "IRES" known in the art include but are not limited to IRES obtainable from picornavirus (Jackson et al., 1990) and IRES obtainable from viral or cellular mRNA sources, such as for example, immunoglobulin heavy-chain binding protein (BiP), the vascular endothelial growth factor (VEGF) (Huez et al. 1998. *Mol. Cell. Biol.* 18(11):6178-6190), the fibroblast growth factor 2 (FGF-2), and insulin-like growth factor (IGFII), the translational initiation factor eIF4G and yeast transcription factors TFIID and HAP4, the encephelomyocarditis virus (EMCV) which is commercially available from Novagen (Duke et al., 1992. J. Virol 66(3): 1602-9) and the VEGF IRES (Huez et al., 1998. Mol Cell Biol 18(11):6178-90). IRES have also been reported in viral genomes of Picornaviridae, Dicistroviridae and Flaviviridae species and in HCV, Friend murine leukemia virus (FrMLV) and Moloney murine leukemia virus (MoMLV).

In one embodiment, the IRES used in polynucleotides contemplated herein is an EMCV IRES.

In particular embodiments, the polynucleotides comprise polynucleotides that have a consensus Kozak sequence and that encode a desired polypeptide. As used herein, the term "Kozak sequence" refers to a short nucleotide sequence that greatly facilitates the initial binding of mRNA to the small subunit of the ribosome and increases translation. The consensus Kozak sequence is (GCC)RCCATGG (SEQ ID NO:43), where R is a purine (A or G) (Kozak, 1986. *Cell.* 44(2):283-92, and Kozak, 1987. *Nucleic Acids Res.* 15(20): 8125-48).

Elements directing the efficient termination and polyadenylation of the heterologous nucleic acid transcripts increases heterologous gene expression. Transcription termination signals are generally found downstream of the polyadenylation signal. In particular embodiments, vectors comprise a polyadenylation sequence 3' of a polynucleotide encoding a polypeptide to be expressed. The term "polyA site" or "polyA sequence" as used herein denotes a DNA sequence which directs both the termination and polyadenylation of the nascent RNA transcript by RNA polymerase II. Polyadenylation sequences can promote mRNA stability by addition of a polyA tail to the 3' end of the coding sequence and thus, contribute to increased translational efficiency. Cleavage and polyadenylation is directed by a poly(A) sequence in the RNA. The core poly(A) sequence for mammalian pre-mRNAs has two recognition elements flanking a cleavage-polyadenylation site. Typically, an almost invariant AAUAAA hexamer lies 20-50 nucleotides upstream of a more variable element rich in U or GU residues. Cleavage of the nascent transcript occurs between these two elements and is coupled to the addition of up to 250 adenosines to the 5' cleavage product. In particular embodiments, the core poly(A) sequence is an ideal polyA sequence (e.g., AATAAA, ATTAAA, AGTAAA). In particular embodiments, the poly(A) sequence is an SV40 polyA sequence, a bovine growth hormone polyA sequence (BGHpA), a rabbit β-globin polyA sequence (rβgpA), variants thereof, or another suitable heterologous or endogenous polyA sequence known in the art. In particular embodiments, the poly(A) sequence is synthetic.

In some embodiments, a polynucleotide or cell harboring the polynucleotide utilizes a suicide gene, including an inducible suicide gene to reduce the risk of direct toxicity and/or uncontrolled proliferation. In specific embodiments, the suicide gene is not immunogenic to the host harboring the polynucleotide or cell. A certain example of a suicide gene that may be used is caspase-9 or caspase-8 or cytosine deaminase. Caspase-9 can be activated using a specific chemical inducer of dimerization (CID).

In certain embodiments, polynucleotides comprise gene segments that cause the immune effector cells, e.g., T cells, to be susceptible to negative selection in vivo. By "negative selection" is meant that the infused cell can be eliminated as a result of a change in the in vivo condition of the individual. The negative selectable phenotype may result from the insertion of a gene that confers sensitivity to an administered agent, for example, a compound. Negative selectable genes are known in the art, and include, inter alia the following: the Herpes simplex virus type I thymidine kinase (HSV-I TK) gene (Wigler et al., *Cell* 11:223, 1977) which confers ganciclovir sensitivity; the cellular hypoxanthine phosphoribosyltransferase (HPRT) gene, the cellular adenine phosphoribosyltransferase (APRT) gene, and bacterial cytosine deaminase, (Mullen et al., *Proc. Natl. Acad. Sci. USA*. 89:33 (1992)).

In some embodiments, genetically modified immune effector cells, such as T cells, comprise a polynucleotide further comprising a positive marker that enables the selection of cells of the negative selectable phenotype in vitro. The positive selectable marker may be a gene which, upon being introduced into the host cell expresses a dominant phenotype permitting positive selection of cells carrying the gene. Genes of this type are known in the art, and include, inter alia, hygromycin-B phosphotransferase gene (hph) which confers resistance to hygromycin B, the amino glycoside phosphotransferase gene (neo or aph) from Tn5 which codes for resistance to the antibiotic G418, the dihydrofolate reductase (DHFR) gene, the adenosine deaminase gene (ADA), and the multi-drug resistance (MDR) gene.

In one embodiment, the positive selectable marker and the negative selectable element are linked such that loss of the negative selectable element necessarily also is accompanied by loss of the positive selectable marker. In a particular embodiment, the positive and negative selectable markers are fused so that loss of one obligatorily leads to loss of the other. An example of a fused polynucleotide that yields as an expression product a polypeptide that confers both the desired positive and negative selection features described above is a hygromycin phosphotransferase thymidine kinase fusion gene (HyTK). Expression of this gene yields a polypeptide that confers hygromycin B resistance for positive selection in vitro, and ganciclovir sensitivity for negative selection in vivo. See also the publications of PCT US91/08442 and PCT/US94/05601, by S. D. Lupton, describing the use of bifunctional selectable fusion genes derived from fusing a dominant positive selectable markers with negative selectable markers.

Preferred positive selectable markers are derived from genes selected from the group consisting of hph, neo, and gpt, and preferred negative selectable markers are derived from genes selected from the group consisting of cytosine deaminase, HSV-I TK, VZV TK, HPRT, APRT and gpt. Exemplary bifunctional selectable fusion genes contemplated in particular embodiments include but are not limited to genes wherein the positive selectable marker is derived from hph or neo, and the negative selectable marker is derived from cytosine deaminase or a TK gene or selectable marker.

In particular embodiments, polynucleotides encoding one or more polypeptides, or fusion polypeptides may be introduced into immune effector cells, e.g., T cells, by both non-viral and viral methods. In particular embodiments, delivery of one or more polynucleotides may be provided by the same method or by different methods, and/or by the same vector or by different vectors.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell or may include sequences sufficient to allow integration into host cell DNA. In particular embodiments, non-viral vectors are used to deliver one or more polynucleotides contemplated herein to a T cell.

Illustrative examples of non-viral vectors include, but are not limited to plasmids (e.g., DNA plasmids or RNA plasmids), transposons, cosmids, and bacterial artificial chromosomes.

Illustrative methods of non-viral delivery of polynucleotides contemplated in particular embodiments include, but are not limited to: electroporation, sonoporation, lipofection, microinjection, biolistics, virosomes, liposomes, immunoliposomes, nanoparticles, polycation or lipid:nucleic acid conjugates, naked DNA, artificial virions, DEAE-dextran-mediated transfer, gene gun, and heat-shock.

Illustrative examples of polynucleotide delivery systems suitable for use in particular embodiments contemplated in particular embodiments include, but are not limited to those provided by Amaxa Biosystems, Maxcyte, Inc., BTX Molecular Delivery Systems, and Copernicus Therapeutics Inc. Lipofection reagents are sold commercially (e.g., Transfectam™ and Lipofectin™). Cationic and neutral lipids that are suitable for efficient receptor-recognition lipofection of polynucleotides have been described in the literature. See e.g., Liu et al. (2003) *Gene Therapy*. 10:180-187; and Balazs et al. (2011) *Journal of Drug Delivery*. 2011:1-12. Antibody-targeted, bacterially derived, non-living nanocell-based delivery is also contemplated in particular embodiments.

Viral vectors comprising polynucleotides contemplated in particular embodiments can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., mobilized peripheral blood, lymphocytes, bone marrow aspirates, tissue biopsy, etc.) or universal donor hematopoietic stem cells, followed by reimplantation of the cells into a patient.

In one embodiment, viral vectors comprising polynucleotides contemplated herein are administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Illustrative examples of viral vector systems suitable for use in particular embodiments contemplated in particular embodiments include but are not limited to adeno-associated virus (AAV), retrovirus, herpes simplex virus, adenovirus, and vaccinia virus vectors.

In various embodiments, one or more polynucleotides are introduced into an immune effector cell, e.g., T cell, by transducing the cell with a recombinant adeno-associated virus (rAAV), comprising the one or more polynucleotides.

AAV is a small (~26 nm) replication-defective, primarily episomal, non-enveloped virus. AAV can infect both dividing and non-dividing cells and may incorporate its genome into that of the host cell. Recombinant AAV (rAAV) are typically composed of, at a minimum, a transgene and its regulatory sequences, and 5' and 3' AAV inverted terminal repeats (ITRs). The ITR sequences are about 145 bp in length. In particular embodiments, the rAAV comprises ITRs and capsid sequences isolated from AAV1, AAV2, AAV3, AAV4, AAV5, AAV6, AAV7, AAV8, AAV9, or AAV10.

In some embodiments, a chimeric rAAV is used the ITR sequences are isolated from one AAV serotype and the capsid sequences are isolated from a different AAV serotype. For example, a rAAV with ITR sequences derived from AAV2 and capsid sequences derived from AAV6 is referred to as AAV2/AAV6. In particular embodiments, the rAAV vector may comprise ITRs from AAV2, and capsid proteins from any one of AAV1, AAV2, AAV3, AAV4, AAV5, AAV6, AAV7, AAV8, AAV9, or AAV10. In a preferred embodiment, the rAAV comprises ITR sequences derived from AAV2 and capsid sequences derived from AAV6. In a preferred embodiment, the rAAV comprises ITR sequences derived from AAV2 and capsid sequences derived from AAV2.

In some embodiments, engineering and selection methods can be applied to AAV capsids to make them more likely to transduce cells of interest.

Construction of rAAV vectors, production, and purification thereof have been disclosed, e.g., in U.S. Pat. Nos. 9,169,494; 9,169,492; 9,012,224; 8,889,641; 8,809,058; and 8,784,799, each of which is incorporated by reference herein, in its entirety.

In various embodiments, one or more polynucleotides are introduced into an immune effector cell, e.g., T cell, by transducing the cell with a retrovirus, e.g., lentivirus, comprising the one or more polynucleotides.

As used herein, the term "retrovirus" refers to an RNA virus that reverse transcribes its genomic RNA into a linear double-stranded DNA copy and subsequently covalently integrates its genomic DNA into a host genome. Illustrative retroviruses suitable for use in particular embodiments, include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus.

As used herein, the term "lentivirus" refers to a group (or genus) of complex retroviruses. Illustrative lentiviruses include but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred.

In various embodiments, a lentiviral vector contemplated herein comprises one or more LTRs, and one or more, or all, of the following accessory elements: a cPPT/FLAP, a Psi ($\Psi$) packaging signal, an export element, poly (A) sequences, and may optionally comprise a WPRE or HPRE, an insulator element, a selectable marker, and a cell suicide gene, as discussed elsewhere herein.

In particular embodiments, lentiviral vectors contemplated herein may be integrative or non-integrating or integration defective lentivirus. As used herein, the term "integration defective lentivirus" or "IDLV" refers to a lentivirus having an integrase that lacks the capacity to integrate the viral genome into the genome of the host cells. Integration-incompetent viral vectors have been described in patent application WO 2006/010834, which is herein incorporated by reference in its entirety.

Illustrative mutations in the HIV-1 pol gene suitable to reduce integrase activity include, but are not limited to: H12N, H12C, H16C, H16V, S81R, D41A, K42A, H51A, Q53C, D55V, D64E, D64V, E69A, K71A, E85A, E87A, D116N, D1161, D116A, N120G, N1201, N120E, E152G, E152A, D35E, K156E, K156A, E157A, K159E, K159A, K160A, R166A, D167A, E170A, H171A, K173A, K186Q, K186T, K188T, E198A, R199c, R199T, R199A, D202A, K211A, Q214L, Q216L, Q221 L, W235F, W235E, K236S, K236A, K246A, G247W, D253A, R262A, R263A and K264H.

The term "long terminal repeat (LTR)" refers to domains of base pairs located at the ends of retroviral DNAs which, in their natural sequence context, are direct repeats and contain U3, R and U5 regions.

As used herein, the term "FLAP element" or "cPPT/FLAP" refers to a nucleic acid whose sequence includes the central polypurine tract and central termination sequences (cPPT and CTS) of a retrovirus, e.g., HIV-1 or HIV-2. Suitable FLAP elements are described in U.S. Pat. No. 6,682,907 and in Zennou, et al., 2000, *Cell,* 101:173.

As used herein, the term "packaging signal" or "packaging sequence" refers to psi [$\Psi$] sequences located within the retroviral genome which are required for insertion of the viral RNA into the viral capsid or particle, see e.g., Clever et al., 1995. *J. of Virology,* Vol. 69, No. 4; pp. 2101-2109.

The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. *J. Virol.* 65: 1053; and Cullen et al., 1991. *Cell* 58: 423), and the hepatitis B virus post-transcriptional regulatory element (HPRE).

In particular embodiments, expression of heterologous sequences in viral vectors is increased by incorporating posttranscriptional regulatory elements, efficient polyadenylation sites, and optionally, transcription termination signals into the vectors. A variety of posttranscriptional regulatory elements can increase expression of a heterologous nucleic acid at the protein, e.g., woodchuck hepatitis virus posttranscriptional regulatory element (WPRE; Zufferey et al., 1999, *J. Virol.,* 73:2886); the posttranscriptional regulatory element present in hepatitis B virus (HPRE) (Huang et al., *Mol. Cell. Biol.*, 5:3864); and the like (Liu et al., 1995, *Genes Dev.*, 9:1766).

Lentiviral vectors preferably contain several safety enhancements as a result of modifying the LTRs. "Self-inactivating" (SIN) vectors refers to replication-defective vectors, e.g., retroviral or lentiviral vectors, in which the right (3') LTR enhancer-promoter region, known as the U3 region, has been modified (e.g., by deletion or substitution) to prevent viral transcription beyond the first round of viral replication. Self-inactivation is preferably achieved through in the introduction of a deletion in the U3 region of the 3' LTR of the vector DNA, i.e., the DNA used to produce the vector RNA. Thus, during reverse transcription, this deletion is transferred to the 5' LTR of the proviral DNA. In particular embodiments, it is desirable to eliminate enough of the U3 sequence to greatly diminish or abolish altogether the transcriptional activity of the LTR, thereby greatly diminishing or abolishing the production of full-length vector RNA in transduced cells. In the case of HIV based lentivectors, it has been discovered that such vectors tolerate significant U3 deletions, including the removal of the LTR TATA box (e.g., deletions from −418 to −18), without significant reductions in vector titers.

An additional safety enhancement is provided by replacing the U3 region of the 5' LTR with a heterologous promoter to drive transcription of the viral genome during production of viral particles. Examples of heterologous promoters which can be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters.

The terms "pseudotype" or "pseudotyping" as used herein, refer to a virus whose viral envelope proteins have been substituted with those of another virus possessing preferable characteristics. For example, HIV can be pseudotyped with vesicular stomatitis virus G-protein (VSV-G) envelope proteins, which allows HIV to infect a wider range of cells because HIV envelope proteins (encoded by the env gene) normally target the virus to $CD4^+$ presenting cells.

In certain embodiments, lentiviral vectors are produced according to known methods. See e.g., Kutner et al., *BMC Biotechnol.* 2009; 9:10. doi: 10.1186/1472-6750-9-10; Kutner et al. *Nat. Protoc.* 2009; 4(4):495-505. doi: 10.1038/nprot.2009.22.

According to certain specific embodiments contemplated herein, most or all of the viral vector backbone sequences are derived from a lentivirus, e.g., HIV-1. However, it is to be understood that many different sources of retroviral and/or lentiviral sequences can be used or combined and numerous substitutions and alterations in certain of the lentiviral sequences may be accommodated without impairing the ability of a transfer vector to perform the functions described herein. Moreover, a variety of lentiviral vectors are known in the art, see Naldini et al., (1996a, 1996b, and 1998); Zufferey et al., (1997); Dull et al., 1998, U.S. Pat. Nos. 6,013,516; and 5,994,136, many of which may be adapted to produce a viral vector or transfer plasmid contemplated herein.

In various embodiments, one or more polynucleotides are introduced into an immune effector cell, by transducing the cell with an adenovirus comprising the one or more polynucleotides.

Adenoviral based vectors are capable of very high transduction efficiency in many cell types and do not require cell division. With such vectors, high titer and high levels of expression have been obtained. This vector can be produced in large quantities in a relatively simple system. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity.

Generation and propagation of the current adenovirus vectors, which are replication deficient, may utilize a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones & Shenk, 1978), the current adenovirus vectors, with the help of 293 cells, carry foreign DNA in either the E1, the D3 or both regions (Graham & Prevec, 1991). Adenovirus vectors have been used in eukaryotic gene expression (Levrero et al., 1991; Gomez-Foix et al., 1992) and vaccine development (Grunhaus & Horwitz, 1992; Graham & Prevec, 1992). Studies in administering recombinant adenovirus to different tissues include trachea instillation (Rosenfeld et al., 1991; Rosenfeld et al., 1992), muscle injection (Ragot et al., 1993), peripheral intravenous injections (Herz & Gerard, 1993) and stereotactic inoculation into the brain (Le Gal La Salle et al., 1993). An example of the use of an Ad vector in a clinical trial involved polynucleotide therapy for antitumor immunization with intramuscular injection (Sterman et al., *Hum. Gene Ther.* 7:1083-9 (1998)).

In various embodiments, one or more polynucleotides are introduced into an immune effector cell by transducing the cell with a herpes simplex virus, e.g., HSV-1, HSV-2, comprising the one or more polynucleotides.

The mature HSV virion consists of an enveloped icosahedral capsid with a viral genome consisting of a linear double-stranded DNA molecule that is 152 kb. In one embodiment, the HSV based viral vector is deficient in one or more essential or non-essential HSV genes. In one embodiment, the HSV based viral vector is replication deficient. Most replication deficient HSV vectors contain a deletion to remove one or more intermediate-early, early, or late HSV genes to prevent replication. For example, the HSV vector may be deficient in an immediate early gene selected from the group consisting of: ICP4, ICP22, ICP27, ICP47, and a combination thereof. Advantages of the HSV vector are its ability to enter a latent stage that can result in long-term DNA expression and its large viral DNA genome that can accommodate exogenous DNA inserts of up to 25 kb. HSV-based vectors are described in, for example, U.S. Pat. Nos. 5,837,532, 5,846,782, and 5,804,413, and International Patent Applications WO 91/02788, WO 96/04394, WO 98/15637, and WO 99/06583, each of which are incorporated by reference herein in its entirety.

G. Genetically Modified Cells

In various embodiments, cells are modified to express DARIC immune receptors, engineered TCRs, CARs, zetakines, and/or fusion proteins contemplated herein, for use in the treatment of cancer. Cells may be non-genetically modified to express the polypeptides contemplated herein, or in particular preferred embodiments, cells may be genetically modified to express the polypeptides contemplated herein. As used herein, the term "genetically engineered" or "genetically modified" refers to the addition of extra genetic material in the form of DNA or RNA into the total genetic material in a cell. The terms, "genetically modified cells," "modified cells," and "redirected cells," are used interchangeably in particular embodiments.

In particular embodiments, the DARIC immune receptor polypeptides contemplated herein are introduced and expressed in immune effector cells to improve the resistance of the cells to the immunosuppressive signals in the TME. In particular embodiments, DARIC immune receptor polypeptides are introduced and expressed in immune effector cells that have been redirected to a target cell by virtue of co-expressing an engineered antigen receptor in the cell.

An "immune effector cell," is any cell of the immune system that has one or more effector functions (e.g., cytotoxic cell killing activity, secretion of cytokines, induction of ADCC and/or CDC). The illustrative immune effector cells contemplated herein are T lymphocytes, in particular cytotoxic T cells (CTLs; CD8+ T cells), TILs, and helper T cells (HTLs; CD4$^+$ T cells. In one embodiment, immune effector cells include natural killer (NK) cells. In one embodiment, immune effector cells include natural killer T (NKT) cells. Immune effector cells can be autologous/autogeneic ("self") or non-autologous ("non-self," e.g., allogeneic, syngeneic or xenogeneic).

"Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells are autologous.

Illustrative immune effector cells suitable for introducing the DARIC immune receptor polypeptides contemplated herein include T lymphocytes. The terms "T cell" or "T lymphocyte" are art-recognized and are intended to include thymocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; CD4$^+$ T cell) CD4$^+$ T cell, a cytotoxic T cell (CTL; CD8+ T cell), CD4$^+$ CD8+ T cell, CD4$^-$CD8$^-$ T cell, or any other subset of T cells. Other illustrative populations of T cells suitable for use in particular embodiments include naïve T cells and memory T cells.

As would be understood by the skilled person, other cells may also be used as immune effector cells with DARIC immune receptor polypeptides contemplated herein. In particular, immune effector cells also include NK cells, NKT cells, neutrophils, and macrophages. Immune effector cells also include progenitors of effector cells wherein such progenitor cells can be induced to differentiate into immune effector cells in vivo or in vitro. Thus, in particular embodiments, immune effector cell includes progenitors of immune effectors cells such as hematopoietic stem cells (HSCs) contained within the CD34$^+$ population of cells derived from cord blood, bone marrow or mobilized peripheral blood which upon administration in a subject differentiate into mature immune effector cells, or which can be induced in vitro to differentiate into mature immune effector cells.

As used herein, immune effector cells genetically engineered to contain a specific chimeric receptor may be referred to as, "antigen specific redirected immune effector cells."

The term, "CD34+ cell," as used herein refers to a cell expressing the CD34 protein on its cell surface. "CD34," as used herein refers to a cell surface glycoprotein (e.g., sialomucin protein) that often acts as a cell-cell adhesion factor and is involved in T cell entrance into lymph nodes. The CD34+ cell population contains hematopoietic stem cells (HSC), which upon administration to a patient differentiate and contribute to all hematopoietic lineages, including T cells, NK cells, NKT cells, neutrophils and cells of the monocyte/macrophage lineage.

Methods for making the immune effector cells which express one or more DARIC immune receptor polypeptides contemplated herein are provided in particular embodiments. In one embodiment, the method comprises transfecting or transducing immune effector cells isolated from an individual such that the immune effector cells with one or more nucleic acids and/or vectors or combination thereof comprising one or more DARIC immune receptor polypeptides as contemplated herein. In one embodiment, the method comprises transfecting or transducing immune effector cells isolated from an individual such that the immune effector cells express one or more DARIC immune receptor polypeptides and engineered antigen receptors contemplated herein. In certain embodiments, the immune effector cells are isolated from an individual and genetically modified without further manipulation in vitro. Such cells can then be directly re-administered into the individual. In further embodiments, the immune effector cells are first activated and stimulated to proliferate in vitro prior to being genetically modified. In this regard, the immune effector cells may be cultured before and/or after being genetically modified.

In particular embodiments, prior to in vitro manipulation or genetic modification of the immune effector cells described herein, the source of cells is obtained from a subject. In particular embodiments, the modified immune effector cells comprise T cells.

T cells can be obtained from a number of sources including, but not limited to, peripheral blood mononuclear cells, bone marrow, lymph nodes tissue, cord blood, thymus issue, tissue from a site of infection, ascites, pleural effusion, spleen tissue, and tumors. In certain embodiments, T cells can be obtained from a unit of blood collected from a subject using any number of techniques known to the skilled person, such as sedimentation, e.g., FICOLL™ separation.

In other embodiments, an isolated or purified population of T cells is used. In some embodiments, after isolation of PBMC, both cytotoxic and helper T lymphocytes can be sorted into naïve, memory, and effector T cell subpopulations either before or after activation, expansion, and/or genetic modification.

In one embodiment, an isolated or purified population of T cells expresses one or more of the markers including, but not limited to a CD3$^+$, CD4$^+$, CD8$^+$, or a combination thereof.

In certain embodiments, the T cells are isolated from an individual and first activated and stimulated to proliferate in vitro prior to being modified to express one or more DARIC immune receptor polypeptides.

In order to achieve sufficient therapeutic doses of T cell compositions, T cells are often subjected to one or more rounds of stimulation, activation and/or expansion. T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041, each of which is incorporated herein by reference in its entirety. In particular embodiments, T cells are activated and expanded for about 6 hours, about 12 hours, about 18 hours or about 24 hours prior to introduction of vectors or polynucleotides encoding one or more DARIC immune receptor polypeptides. Optionally in combination with an engineered antigen receptor contemplated herein.

In one embodiment, T cells are activated at the same time that they are modified.

In various embodiments, a method of generating an immune effector cell comprises activating a population of cells comprising T cells and expanding the population of T cells. T cell activation can be accomplished by providing a primary stimulation signal through the T cell TCR/CD3 complex and by providing a secondary co-stimulation signal through an accessory molecule, e.g., CD28.

The TCR/CD3 complex may be stimulated by contacting the T cell with a suitable CD3 binding agent, e.g., a CD3 ligand or an anti-CD3 monoclonal antibody. Illustrative examples of CD3 antibodies include, but are not limited to, OKT3, G19-4, BC3, and 64.1.

In addition to the primary stimulation signal provided through the TCR/CD3 complex, induction of T cell responses requires a second, co-stimulatory signal. In particular embodiments, a CD28 binding agent can be used to provide a co-stimulatory signal. Illustrative examples of CD28 binding agents include but are not limited to: natural CD 28 ligands, e.g., a natural ligand for CD28 (e.g., a member of the B7 family of proteins, such as B7-1(CD80) and B7-2 (CD86); and anti-CD28 monoclonal antibody or fragment thereof capable of crosslinking the CD28 molecule, e.g., monoclonal antibodies 9.3, B-T3, XR-CD28, KOLT-2, 15E8, 248.23.2, and EX5.3D10.

In one embodiment, the molecule providing the primary stimulation signal, for example a molecule which provides stimulation through the TCR/CD3 complex and the co-stimulatory molecule are coupled to the same surface.

In certain embodiments, binding agents that provide stimulatory and co-stimulatory signals are localized on the surface of a cell. This can be accomplished by transfecting or transducing a cell with a nucleic acid encoding the binding agent in a form suitable for its expression on the cell surface or alternatively by coupling a binding agent to the cell surface.

In another embodiment, the molecule providing the primary stimulation signal, for example a molecule which provides stimulation through the TCR/CD3 complex and the co-stimulatory molecule are displayed on antigen presenting cells.

In one embodiment, the molecule providing the primary stimulation signal, for example a molecule which provides stimulation through the TCR/CD3 complex and the co-stimulatory molecule are provided on separate surfaces.

In a certain embodiment, one of the binding agents that provides stimulatory and co-stimulatory signals is soluble (provided in solution) and the other agent(s) is provided on one or more surfaces.

In a particular embodiment, the binding agents that provide stimulatory and co-stimulatory signals are both provided in a soluble form (provided in solution).

In various embodiments, the methods for making T cells contemplated herein comprise activating T cells with anti-CD3 and anti-CD28 antibodies.

In one embodiment, expanding T cells activated by the methods contemplated herein further comprises culturing a population of cells comprising T cells for several hours (about 3 hours) to about 7 days to about 28 days or any hourly integer value in between. In another embodiment, the T cell composition may be cultured for 14 days. In a particular embodiment, T cells are cultured for about 21 days. In another embodiment, the T cell compositions are cultured for about 2-3 days. Several cycles of stimulation/activation/expansion may also be desired such that culture time of T cells can be 60 days or more.

In particular embodiments, conditions appropriate for T cell culture include an appropriate media (e.g., Minimal Essential Media or RPMI Media 1640 or, X-vivo 15, (Lonza)) and one or more factors necessary for proliferation and viability including, but not limited to serum (e.g., fetal bovine or human serum), interleukin-2 (IL-2), insulin, IFN-γ, IL-4, IL-7, IL-21, GM-CSF, IL-10, IL-12, IL-15, TGFβ, and TNF-α or any other additives suitable for the growth of cells known to the skilled artisan.

Further illustrative examples of cell culture media include, but are not limited to RPMI 1640, Clicks, AIM-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells.

Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% C02).

In particular embodiments, PBMCs or isolated T cells are contacted with a stimulatory agent and co-stimulatory agent, such as anti-CD3 and anti-CD28 antibodies, generally attached to a bead or other surface, in a culture medium with appropriate cytokines, such as IL-2, IL-7, and/or IL-15.

In other embodiments, artificial APC (aAPC) made by engineering K562, U937, 721.221, T2, and C1R cells to direct the stable expression and secretion, of a variety of co-stimulatory molecules and cytokines. In a particular embodiment K32 or U32 aAPCs are used to direct the display of one or more antibody-based stimulatory molecules on the AAPC cell surface. Populations of T cells can be expanded by aAPCs expressing a variety of co-stimulatory molecules including, but not limited to, CD137L (4-1BBL), CD134L (OX40L), and/or CD80 or CD86. Finally, the aAPCs provide an efficient platform to expand genetically modified T cells and to maintain CD28 expression on CD8α T cells. aAPCs provided in WO 03/057171 and US2003/0147869 are hereby incorporated by reference in their entirety.

In a particular embodiment, polynucleotide encoding one or more DARIC immune receptor polypeptides and an engineered antigen receptor are introduced into the population of T cells. In a particular embodiment, polynucleotide encoding one or more DARIC immune receptor polypeptides is introduced into a population of T cells that express an engineered antigen receptor. The polynucleotides may be introduced into the T cells by microinjection, transfection, lipofection, heat-shock, electroporation, transduction, gene gun, microinjection, DEAE-dextran-mediated transfer, and the like.

In a preferred embodiment, polynucleotides are introduced into a T cell by viral transduction.

Illustrative examples of viral vector systems suitable for introducing a polynucleotide into an immune effector cell or CD34+ cell include but are not limited to adeno-associated virus (AAV), retrovirus, herpes simplex virus, adenovirus, vaccinia virus vectors for gene transfer.

In one embodiment, polynucleotides are introduced into a T cell by AAV transduction.

In one embodiment, polynucleotides are introduced into a T cell by retroviral transduction.

In one embodiment, polynucleotides are introduced into a T cell by lentiviral transduction.

In one embodiment, polynucleotides are introduced into a T cell by adenovirus transduction.

In one embodiment, polynucleotides are introduced into a T cell by herpes simplex virus transduction.

In one embodiment, polynucleotides are introduced into a T cell by vaccinia virus transduction.

H. Compositions and Formulations

The compositions contemplated herein may comprise one or more polypeptides, polynucleotides, vectors comprising same, genetically modified immune effector cells, bridging factors, etc. Compositions include but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" refers to a diluent, adjuvant, excipient, or vehicle with which the bridging factors, polypeptides, polynucleotides, vectors comprising same, or genetically modified immune effector cells are administered. Illustrative examples of pharmaceutical carriers can be sterile liquids, such as cell culture media, water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients in particular embodiments, include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Except insofar as any conventional media or agent is incompatible with the active ingredient, its use in the therapeutic compositions is contemplated. Supplementary active ingredients can also be incorporated into the compositions.

In one embodiment, a composition comprising a pharmaceutically acceptable carrier is suitable for administration to a subject. In particular embodiments, a composition comprising a carrier is suitable for parenteral administration, e.g., intravascular (intravenous or intraarterial), intraperitoneal or intramuscular administration. In particular embodiments, a composition comprising a pharmaceutically acceptable carrier is suitable for intraventricular, intraspinal, or intrathecal administration. Pharmaceutically acceptable carriers include sterile aqueous solutions, cell culture media, or dispersions. The use of such media and agents for pharmaceutically active substances is well known in the art. Except insofar as any conventional media or agent is incompatible with the bridging factors, polypeptides, polynucleotides, vectors comprising same, or genetically modified immune effector cells, use thereof in the pharmaceutical compositions is contemplated.

In particular embodiments, compositions contemplated herein comprise genetically modified T cells and a pharmaceutically acceptable carrier. A composition comprising a cell-based composition contemplated herein can be administered separately by enteral or parenteral administration methods or in combination with other suitable compounds to effect the desired treatment goals.

In particular embodiments, compositions contemplated herein comprise a bridging factor and a pharmaceutically acceptable carrier.

The pharmaceutically acceptable carrier must be of sufficiently high purity and of sufficiently low toxicity to render it suitable for administration to the human subject being treated. It further should maintain or increase the stability of the composition. The pharmaceutically acceptable carrier can be liquid or solid and is selected, with the planned manner of administration in mind, to provide for the desired bulk, consistency, etc., when combined with other components of the composition. For example, the pharmaceutically acceptable carrier can be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulfate, etc.). Other suitable pharmaceutically acceptable carriers for the compositions contemplated herein include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like.

Such carrier solutions also can contain buffers, diluents and other suitable additives. The term "buffer" as used herein refers to a solution or liquid whose chemical makeup neutralizes acids or bases without a significant change in pH. Examples of buffers contemplated herein include, but are not limited to, Dulbecco's phosphate buffered saline (PBS), Ringer's solution, 5% dextrose in water (D5W), normal/physiologic saline (0.9% NaCl).

The pharmaceutically acceptable carriers may be present in amounts sufficient to maintain a pH of the composition of about 7. Alternatively, the composition has a pH in a range from about 6.8 to about 7.4, e.g., 6.8, 6.9, 7.0, 7.1, 7.2, 7.3, and 7.4. In still another embodiment, the composition has a pH of about 7.4.

Compositions contemplated herein may comprise a nontoxic pharmaceutically acceptable medium. The compositions may be a suspension. The term "suspension" as used herein refers to non-adherent conditions in which cells are not attached to a solid support. For example, cells maintained as a suspension may be stirred or agitated and are not adhered to a support, such as a culture dish.

In particular embodiments, compositions contemplated herein are formulated in a suspension, where the modified T cells are dispersed within an acceptable liquid medium or solution, e.g., saline or serum-free medium, in an intravenous (IV) bag or the like. Acceptable diluents include, but are not limited to water, PlasmaLyte, Ringer's solution, isotonic sodium chloride (saline) solution, serum-free cell culture medium, and medium suitable for cryogenic storage, e.g., Cryostor® medium.

In certain embodiments, a pharmaceutically acceptable carrier is substantially free of natural proteins of human or animal origin, and suitable for storing a composition comprising a population of modified T cells. The therapeutic composition is intended to be administered into a human patient, and thus is substantially free of cell culture components such as bovine serum albumin, horse serum, and fetal bovine serum.

In some embodiments, compositions are formulated in a pharmaceutically acceptable cell culture medium. Such compositions are suitable for administration to human subjects. In particular embodiments, the pharmaceutically acceptable cell culture medium is a serum free medium.

Serum-free medium has several advantages over serum containing medium, including a simplified and better defined composition, a reduced degree of contaminants, elimination of a potential source of infectious agents, and lower cost. In various embodiments, the serum-free medium is animal-free, and may optionally be protein-free. Optionally, the medium may contain biopharmaceutically acceptable recombinant proteins. "Animal-free" medium refers to medium wherein the components are derived from non-animal sources. Recombinant proteins replace native animal proteins in animal-free medium and the nutrients are obtained from synthetic, plant or microbial sources. "Protein-free" medium, in contrast, is defined as substantially free of protein.

Illustrative examples of serum-free media used in particular compositions includes but is not limited to QBSF-60 (Quality Biological, Inc.), StemPro-34 (Life Technologies), and X-VIVO 10.

In a preferred embodiment, the compositions comprising modified T cells are formulated in PlasmaLyte.

In various embodiments, compositions comprising modified T cells are formulated in a cryopreservation medium. For example, cryopreservation media with cryopreservation agents may be used to maintain a high cell viability outcome post-thaw. Illustrative examples of cryopreservation media used in particular compositions includes, but is not limited to, CryoStor CS10, CryoStor CS5, and CryoStor CS2.

In one embodiment, the compositions are formulated in a solution comprising 50:50 PlasmaLyte A to CryoStor CS10.

In particular embodiments, the composition is substantially free of *mycoplasma*, endotoxin, and microbial contamination. By "substantially free" with respect to endotoxin is meant that there is less endotoxin per dose of cells than is allowed by the FDA for a biologic, which is a total endotoxin of 5 EU/kg body weight per day, which for an average 70 kg person is 350 EU per total dose of cells. In particular embodiments, compositions contemplated herein contain about 0.5 EU/mL to about 5.0 EU/mL, or about 0.5 EU/mL, 1.0 EU/mL, 1.5 EU/mL, 2.0 EU/mL, 2.5 EU/mL, 3.0 EU/mL, 3.5 EU/mL, 4.0 EU/mL, 4.5 EU/mL, or 5.0 EU/mL.

In particular embodiments, formulation of pharmaceutically-acceptable carrier solutions is well-known to those of skill in the art, as is the development of suitable dosing and treatment regimens for using the particular compositions described herein in a variety of treatment regimens, including e.g., enteral and parenteral, e.g., intravascular, intravenous, intrarterial, intraosseously, intraventricular, intracerebral, intracranial, intraspinal, intrathecal, and intramedullary administration and formulation. It would be understood by the skilled artisan that particular embodiments contemplated herein may comprise other formulations, such as those that are well known in the pharmaceutical art, and are described, for example, in *Remington: The Science and Practice of Pharmacy*, volume I and volume II. $22^{nd}$ Edition. Edited by Loyd V. Allen Jr. Philadelphia, PA: Pharmaceutical Press; 2012, which is incorporated by reference herein, in its entirety.

In particular embodiments, compositions comprise an amount of immune effector cells, including CAR T cells, that express one or more DARIC immune receptor polypeptides contemplated herein. As used herein, the term "amount" refers to "an amount effective" or "an effective amount" of cells comprising one or more DARIC immune receptor polypeptides contemplated herein, etc., to achieve a beneficial or desired prophylactic or therapeutic result, including clinical results.

A "prophylactically effective amount" refers to an amount of cells comprising one or more DARIC immune receptor polypeptides contemplated herein, etc., effective to achieve the desired prophylactic result. Typically, but not necessarily, since a prophylactic dose is used in subjects prior to or at an earlier stage of disease, the prophylactically effective amount is less than the therapeutically effective amount.

A "therapeutically effective amount" refers to an amount of cells comprising one or more DARIC immune receptor polypeptides contemplated herein that is effective to "treat" a subject (e.g., a patient). When a therapeutic amount is indicated, the precise amount of the compositions to be administered can be determined by a physician with consideration of individual differences in age, weight, tumor size, extent of infection or metastasis, and condition of the patient (subject). It can generally be stated that a pharmaceutical composition comprising the immune effector cells described herein may be administered at a dosage of $10^2$ to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mLs or less, even 250 mLs or 100 mLs or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some embodiments, particularly since all the infused cells will be redirected to a particular target antigen, lower numbers of cells, in the range of $10^6$/kilogram ($10^6$-$10^{11}$ per patient) may be administered. If desired, the treatment may also include administration of mitogens (e.g., PHA) or lymphokines, cytokines, and/or chemokines (e.g., IFN-γ, IL-2, IL-12, TNF-alpha, IL-18, and TNF-beta, GM-CSF, IL-4, IL-13, Flt3-L, RANTES, MIP1α, etc.) as described herein to enhance induction of the immune response.

Generally, compositions comprising the cells activated and expanded as described herein may be utilized in the treatment and prevention of diseases that arise in individuals who are immunocompromised. In particular, compositions contemplated herein are used in the treatment of cancer. In particular embodiments, the immune effector cells may be administered either alone, or as a pharmaceutical compositions in combination with carriers, diluents, excipients, and/or with other components such as IL-2 or other cytokines or cell populations.

In particular embodiments, pharmaceutical compositions comprise an amount of genetically modified T cells, in combination with one or more pharmaceutically or physiologically acceptable carriers, diluents or excipients.

In a particular embodiment, compositions comprise an effective amount of immune effector cells comprising one or more DARIC immune receptor polypeptides contemplated herein, alone or in combination with one or more therapeutic agents, such as radiation therapy, chemotherapy, transplantation, immunotherapy, hormone therapy, photodynamic therapy, etc. The compositions may also be administered in combination with antibiotics. Such therapeutic agents may be accepted in the art as a standard treatment for a particular disease state as described herein, such as a particular cancer. Exemplary therapeutic agents contemplated include cytokines, growth factors, steroids, NSAIDs, DMARDs, anti-inflammatories, chemotherapeutics, radiotherapeutics, therapeutic antibodies, or other active and ancillary agents.

In certain embodiments, compositions comprising immune effector cells comprising one or more DARIC immune receptor polypeptides contemplated herein may be administered in conjunction with any number of chemotherapeutic agents. Illustrative examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredepa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on cancers such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A variety of other therapeutic agents may be used in conjunction with the compositions described herein. In one embodiment, the composition comprising immune effector cells comprising one or more DARIC immune receptor polypeptides contemplated herein is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

Other exemplary NSAIDs are chosen from the group consisting of ibuprofen, naproxen, naproxen sodium, Cox-2 inhibitors such as VIOXX® (rofecoxib) and CELEBREX® (celecoxib), and sialylates. Exemplary analgesics are chosen from the group consisting of acetaminophen, oxycodone, tramadol of propoxyphene hydrochloride. Exemplary glucocorticoids are chosen from the group consisting of cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular) and minocycline.

Illustrative examples of therapeutic antibodies suitable for combination with the modified T cells comprising one or more DARIC immune receptor polypeptides contemplated herein, include but are not limited to, atezolizumab, avelumab, bavituximab, bevacizumab (avastin), bivatuzumab, blinatumomab, conatumumab, daratumumab, duligotumab, dacetuzumab, dalotuzumab, durvalumab, elotuzumab (Hu- Luc63), gemtuzumab, ibritumomab, indatuximab, inotuzumab, ipilimumab, lorvotuzumab, lucatumumab, milatuzumab, moxetumomab, nivolumab, ocaratuzumab, ofatumumab, pembrolizumab, rituximab, siltuximab, teprotumumab, and ublituximab.

In certain embodiments, the compositions described herein are administered in conjunction with a cytokine. By "cytokine" as used herein is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1 alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

I. Therapeutic Methods

The immune effector cells, including CAR T cells, comprising a DARIC immune receptor contemplated herein provide improved methods of adoptive immunotherapy for use in the prevention, treatment, and amelioration of, or for preventing, treating, or ameliorating at least one symptom associated with, a cancer, GVHD, an infectious disease, an autoimmune disease, an inflammatory disease, or an immunodeficiency.

The immune effector cells that comprise an engineered receptor and a DARIC immune receptor contemplated herein provide improved drug products for use in the prevention, treatment, or amelioration of at least one symptom of a cancer, GVHD, an infectious disease, an autoimmune disease, an inflammatory disease, or an immunodeficiency. As used herein, the term "drug product" refers to modified cells produced using the compositions and methods contemplated herein. In particular embodiments, the drug product comprises genetically modified immune effector cells, T cells comprising an engineered receptor, or CAR T cells further modified to express a DARIC immune receptor. Moreover, the modified T cells contemplated in particular embodiments provide safer and more efficacious adoptive cell therapies because they are resistant to T cell exhaustion and display increased durability and persistence in the tumor microenvironment that can lead to sustained therapy.

In particular embodiments, an effective amount of modified immune effector cells or T cells comprising an engineered receptor and a DARIC immune receptor are administered to a subject to prevent, treat, or ameliorate at least one symptom of a cancer, GVHD, an infectious disease, an autoimmune disease, an inflammatory disease, or an immunodeficiency.

In particular embodiments, a method of preventing, treating, or ameliorating at least one symptom of a cancer comprises administering the subject an effective amount of modified immune effector cells or T cells comprising a DARIC immune receptor and an engineered TCR, CAR, or other therapeutic transgene to redirect the cells to a tumor or cancer. The genetically modified cells are a more durable and persistent drug product because the cells are more resistant to immunosuppressive signals from the tumor microenvironment by virtue of transducing a chemically regulatable immunostimulatory signal.

In particular embodiments, the modified immune effector cells contemplated herein are used in the treatment of solid tumors or cancers.

In particular embodiments, the modified immune effector cells contemplated herein are used in the treatment of solid tumors or cancers including, but not limited to: adrenal cancer, adrenocortical carcinoma, anal cancer, appendix cancer, astrocytoma, atypical teratoid/rhabdoid tumor, basal cell carcinoma, bile duct cancer, bladder cancer, bone cancer, brain/CNS cancer, breast cancer, bronchial tumors, cardiac tumors, cervical cancer, cholangiocarcinoma, chondrosarcoma, chordoma, colon cancer, colorectal cancer, craniopharyngioma, ductal carcinoma in situ (DCIS) endometrial cancer, ependymoma, esophageal cancer, esthesioneuroblastoma, Ewing's sarcoma, extracranial germ cell tumor, extragonadal germ cell tumor, eye cancer, fallopian tube cancer, fibrous histiosarcoma, fibrosarcoma, gallbladder cancer, gastric cancer, gastrointestinal carcinoid tumors, gastrointestinal stromal tumor (GIST), germ cell tumors, glioma, glioblastoma, head and neck cancer, hemangioblastoma, hepatocellular cancer, hypopharyngeal cancer, intraocular melanoma, kaposi sarcoma, kidney cancer, laryngeal cancer, leiomyosarcoma, lip cancer, liposarcoma, liver cancer, lung cancer, non-small cell lung cancer, lung carcinoid tumor, malignant mesothelioma, medullary carcinoma, medulloblastoma, menangioma, melanoma, Merkel cell carcinoma, midline tract carcinoma, mouth cancer, myxosarcoma, myelodysplastic syndrome, myeloproliferative neoplasms, nasal cavity and paranasal sinus cancer, nasopharyngeal cancer, neuroblastoma, oligodendroglioma, oral cancer, oral cavity cancer, oropharyngeal cancer, osteosarcoma, ovarian cancer, pancreatic cancer, pancreatic islet cell tumors, papillary carcinoma, paraganglioma, parathyroid cancer, penile cancer, pharyngeal cancer, pheochromocytoma, pinealoma, pituitary tumor, pleuropulmonary blastoma, primary peritoneal cancer, prostate cancer, rectal cancer, retinoblastoma, renal cell carcinoma, renal pelvis and ureter cancer, rhabdomyosarcoma, salivary gland cancer, sebaceous gland carcinoma, skin cancer, soft tissue sarcoma, squamous cell carcinoma, small cell lung cancer, small intestine cancer, stomach cancer, sweat gland carcinoma, synovioma, testicular cancer, throat cancer, thymus cancer, thyroid cancer, urethral cancer, uterine cancer, uterine sarcoma, vaginal cancer, vascular cancer, vulvar cancer, and Wilms Tumor.

In particular embodiments, the modified immune effector cells contemplated herein are used in the treatment of solid tumors or cancers including, without limitation, liver cancer, pancreatic cancer, lung cancer, breast cancer, bladder cancer, brain cancer, bone cancer, thyroid cancer, kidney cancer, or skin cancer.

In particular embodiments, the modified immune effector cells contemplated herein are used in the treatment of various cancers including but not limited to pancreatic, bladder, and lung.

In particular embodiments, the modified immune effector cells contemplated herein are used in the treatment of liquid cancers or hematological cancers.

In particular embodiments, the modified immune effector cells contemplated herein are used in the treatment of B-cell malignancies, including but not limited to: leukemias, lymphomas, and multiple myeloma.

In particular embodiments, the modified immune effector cells contemplated herein are used in the treatment of liquid cancers including, but not limited to leukemias, lymphomas, and multiple myelomas: acute lymphocytic leukemia (ALL), acute myeloid leukemia (AML), myeloblastic, promyelocytic, myelomonocytic, monocytic, erythroleukemia, hairy cell leukemia (HCL), chronic lymphocytic leukemia (CLL), and chronic myeloid leukemia (CML), chronic myelomonocytic leukemia (CMML) and polycythemia vera, Hodgkin lymphoma, nodular lymphocyte-predominant Hodgkin lymphoma, Burkitt lymphoma, small lymphocytic lymphoma (SLL), diffuse large B-cell lymphoma, follicular lymphoma, immunoblastic large cell lymphoma, precursor B-lymphoblastic lymphoma, mantle cell lymphoma, marginal zone lymphoma, mycosis fungoides, anaplastic large cell lymphoma, Sézary syndrome, precursor T-lymphoblastic lymphoma, multiple myeloma, overt multiple myeloma, smoldering multiple myeloma, plasma cell leukemia, non-secretory myeloma, IgD myeloma, osteosclerotic myeloma, solitary plasmacytoma of bone, and extramedullary plasmacytoma.

Preferred cells for use in the methods contemplated herein include autologous/autogeneic ("self") cells, preferably hematopoietic cells, more preferably T cells, and more preferably immune effector cells.

In particular embodiments, methods comprising administering a therapeutically effective amount of modified immune effector cells contemplated herein or a composition comprising the same, to a patient in need thereof, alone or in combination with one or more therapeutic agents, are provided. In certain embodiments, the cells are used in the treatment of patients at risk for developing a cancer, GVHD, an infectious disease, an autoimmune disease, an inflammatory disease, or an immunodeficiency. Thus, particular embodiments comprise the treatment or prevention or amelioration of at least one symptom of a cancer, an infectious disease, an autoimmune disease, an inflammatory disease, or an immunodeficiency comprising administering to a subject in need thereof, a therapeutically effective amount of the modified immune effector cells contemplated herein.

In one embodiment, a method of treating a cancer, GVHD, an infectious disease, an autoimmune disease, an inflammatory disease, or an immunodeficiency in a subject in need thereof comprises administering an effective amount, e.g., therapeutically effective amount of a composition comprising modified immune effector cells contemplated herein. The quantity and frequency of administration will be determined by such factors as the condition of the patient, and the type and severity of the patient's disease, although appropriate dosages may be determined by clinical trials.

In one illustrative embodiment, the effective amount of modified immune effector cells provided to a subject is at least $2\times10^6$ cells/kg, at least $3\times10^6$ cells/kg, at least $4\times10^6$ cells/kg, at least $5\times10^6$ cells/kg, at least $6\times10^6$ cells/kg, at least $7\times10^6$ cells/kg, at least $8\times10^6$ cells/kg, at least $9\times10^6$ cells/kg, or at least $10\times10^6$ cells/kg, or more cells/kg, including all intervening doses of cells.

In another illustrative embodiment, the effective amount of modified immune effector cells provided to a subject is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, or about $10\times10^6$ cells/kg, or more cells/kg, including all intervening doses of cells.

In another illustrative embodiment, the effective amount of modified immune effector cells provided to a subject is from about $2\times10^6$ cells/kg to about $10\times10^6$ cells/kg, about $3\times10^6$ cells/kg to about $10\times10^6$ cells/kg, about $4\times10^6$ cells/kg to about $10\times10^6$ cells/kg, about $5\times10^6$ cells/kg to about $10\times10^6$ cells/kg, $2\times10^6$ cells/kg to about $6\times10^6$ cells/kg, $2\times10^6$ cells/kg to about $7\times10^6$ cells/kg, $2\times10^6$ cells/kg to about $8\times10^6$ cells/kg, $3\times10^6$ cells/kg to about $6\times10^6$ cells/kg, $3\times10^6$ cells/kg to about $7\times10^6$ cells/kg, $3\times10^6$ cells/kg to about $8\times10^6$ cells/kg, $4\times10^6$ cells/kg to about $6\times10^6$ cells/kg, $4\times10^6$ cells/kg to about $7\times10^6$ cells/kg, $4\times10^6$ cells/kg to about $8\times10^6$ cells/kg, $5\times10^6$ cells/kg to about $6\times10^6$ cells/kg, $5\times10^6$ cells/kg to about $7\times10^6$ cells/kg, $5\times10^6$ cells/kg to about $8\times10^6$ cells/kg, or $6\times10^6$ cells/kg to about $8\times10^6$ cells/kg, including all intervening doses of cells.

One of ordinary skill in the art would recognize that multiple administrations of the compositions contemplated in particular embodiments may be required to effect the desired therapy. For example, a composition may be administered 1, 2, 3, 4, 5, 6, 7, 8, 9, or 10 or more times over a span of 1 week, 2 weeks, 3 weeks, 1 month, 2 months, 3 months, 4 months, 5 months, 6 months, 1 year, 2 years, 5, years, 10 years, or more.

In certain embodiments, it may be desirable to administer activated T cells to a subject and then subsequently redraw blood (or have an apheresis performed), activate T cells therefrom, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, 100 cc, 150 cc, 200 cc, 250 cc, 300 cc, 350 cc, or 400 cc or more. Not to be bound by theory, using this multiple blood draw/multiple reinfusion protocol may serve to select out certain populations of T cells.

In one embodiment, a method of treating a subject diagnosed with a cancer, comprises removing immune effector cells from the subject, modifying the immune effector cells by introducing one or more vectors encoding an engineered antigen receptor and one or more DARIC immune receptors and producing a population of modified immune effector cells, and administering the population of modified immune effector cells to the same subject. In a preferred embodiment, the immune effector cells comprise T cells.

The methods for administering the cell compositions contemplated in particular embodiments include any method which is effective to result in reintroduction of ex vivo modified immune effector cells or on reintroduction of the modified progenitors of immune effector cells that on introduction into a subject differentiate into mature immune effector cells. One method comprises modifying peripheral blood T cells ex vivo by introducing one or more vectors encoding an engineered antigen receptor and one or more DARIC immune receptors and returning the transduced cells into the subject.

All publications, patent applications, and issued patents cited in this specification are herein incorporated by reference as if each individual publication, patent application, or issued patent were specifically and individually indicated to be incorporated by reference.

Although the foregoing embodiments have been described in some detail by way of illustration and example for purposes of clarity of understanding, it will be readily apparent to one of ordinary skill in the art in light of the teachings contemplated herein that certain changes and modifications may be made thereto without departing from the spirit or scope of the appended claims. The following examples are provided by way of illustration only and not by way of limitation. Those of skill in the art will readily recognize a variety of noncritical parameters that could be changed or modified in particular embodiments to yield essentially similar results.

EXAMPLES

Example 1

Rapamycin Induces IFNγ Expression in IL-18 Receptor Daric T Cells

IL-18 receptor (IL-18R) DARIC binding and signaling components were designed, constructed, and verified. An IL-18R DARIC lentiviral vector was constructed comprising an MNDU3 promoter operably linked to a polynucleotide encoding: a DARIC signaling component (CD8α-signal peptide, an FRB variant (T82L), and an IL-18R1 transmembrane and signaling domain); a P2A sequence; and a DARIC binding component (an Igκ-signal peptide, an FKBP12 domain, and a IL-18RAP transmembrane and signaling domain). An IL-18R DARIC-GFP lentiviral vector was constructed by appending another polynucleotide encoding a P2A sequence and GFP to the polynucleotide encoding the IL-18R1 signaling domain in aforementioned vector. T cells transduced with the IL-18R DARIC and IL-18R DARIC-GFP lentiviral vectors express the polypeptides shown in FIG. 1A. See, e.g., SEQ ID NOs: 1-4.

Figure 1B:
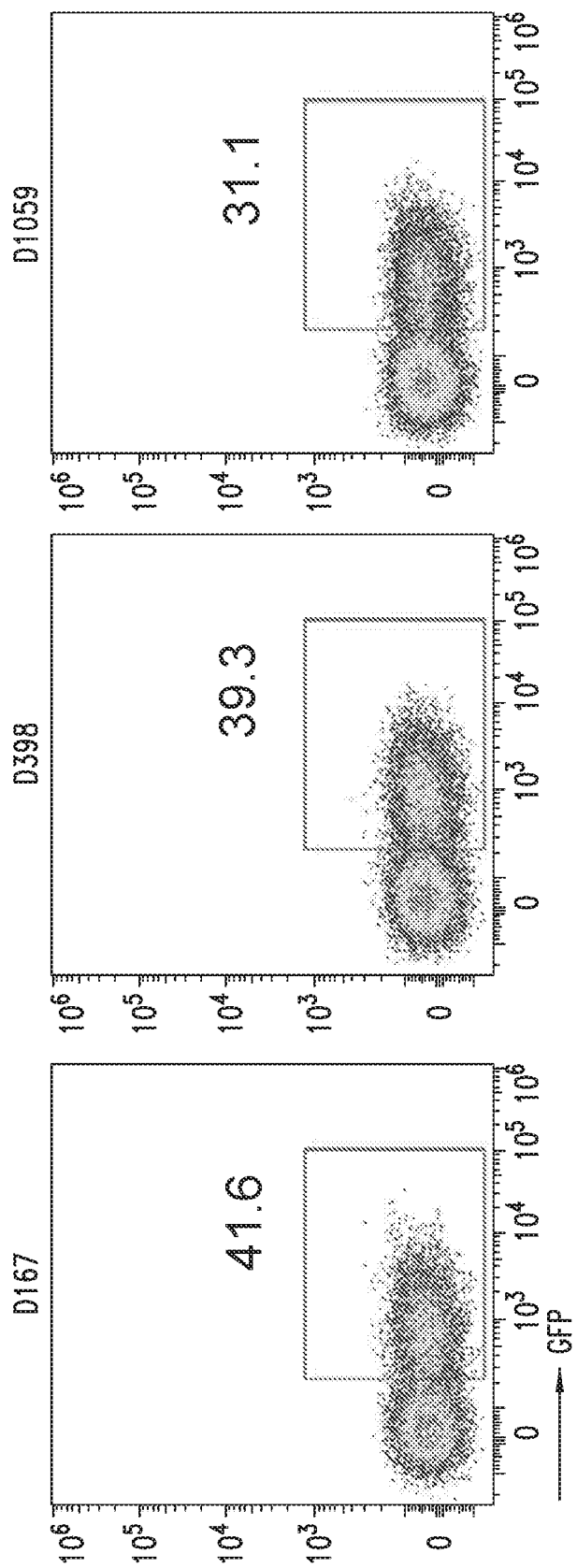
FIG. 1B shows GFP expression in donor PBMCs transduced with LVV encoding IL-18R-DARIC-GFP.

GFP expression was measured in donor PBMCs transduced with LVV encoding IL-18R-DARIC-GFP to assess transduction efficiency. FIG. 1B.

Figure 1C:
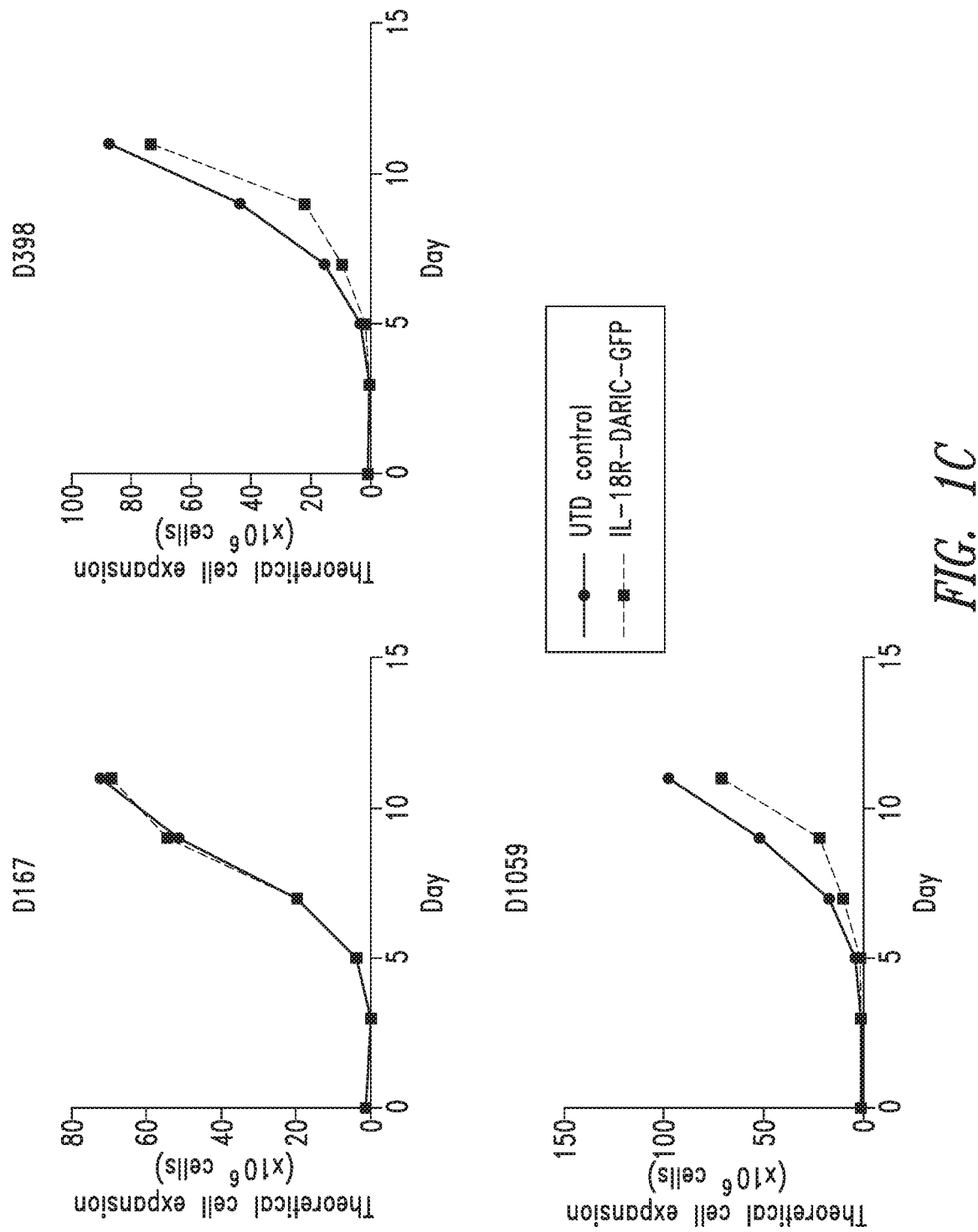
FIG. 1C shows growth curves for untransduced donor PBMCs and PBMCs transduced with LVV encoding IL-18R-DARIC-GFP.

Cell growth was measured in donor PBMCs transduced with LVV encoding IL-18R-DARIC-GFP. The transduced cells showed similar growth kinetics to Untransduced control PBMCs. FIG. 1C.

Figure 1D:
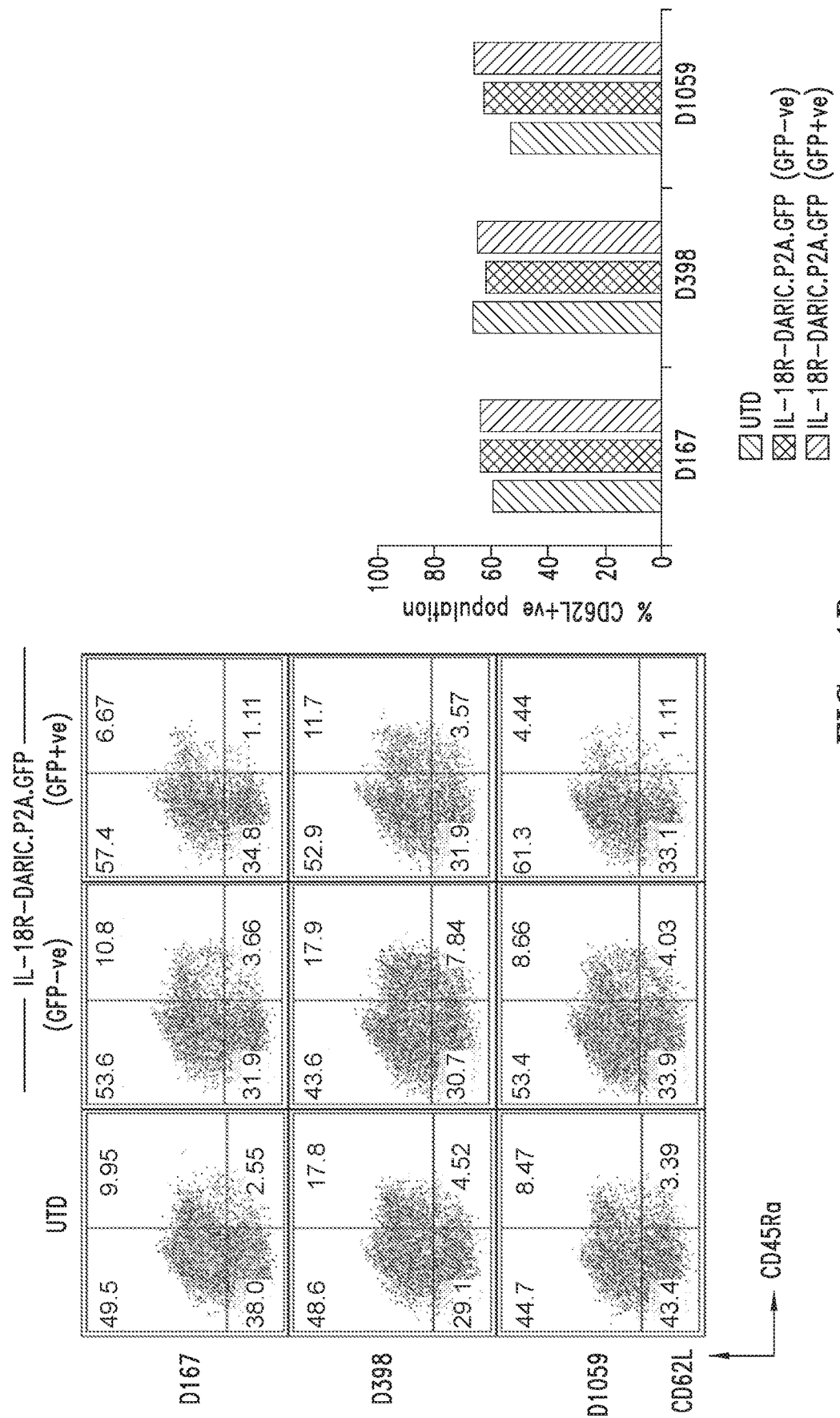
FIG. 1D shows CD62L and CD45Ra expression in untransduced donor PBMCs and PBMCs transduced with LVV encoding IL-18R-DARIC-GFP.

CD62L and CD45Ra expression were measure in donor PBMCs transduced with LVV encoding IL-18R-DARIC-GFP. T cell subset development as assessed by CD62L and CD45Ra expression was similar among IL-18R-DARIC-GFP transduced cells and untransduced controls. FIG. 1D.

Figure 2:
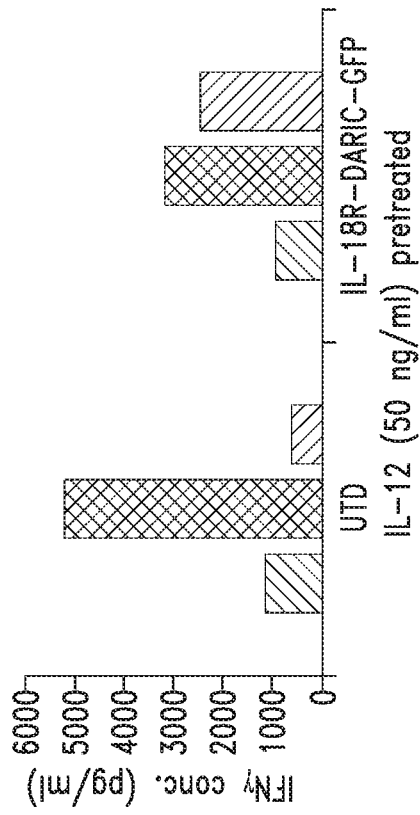
FIG. 2 shows IFNγ production in untransduced donor PBMCs and PBMCs transduced with LVV encoding IL-18R-DARIC-GFP and pre-treated with 50 ng/mL human recombinant IL-12 for 24 hours, and then subsequently cultured in medium only, medium with 100 ng/mL human recombinant IL-18 or medium with 1 nM rapamycin.
Figure 2:
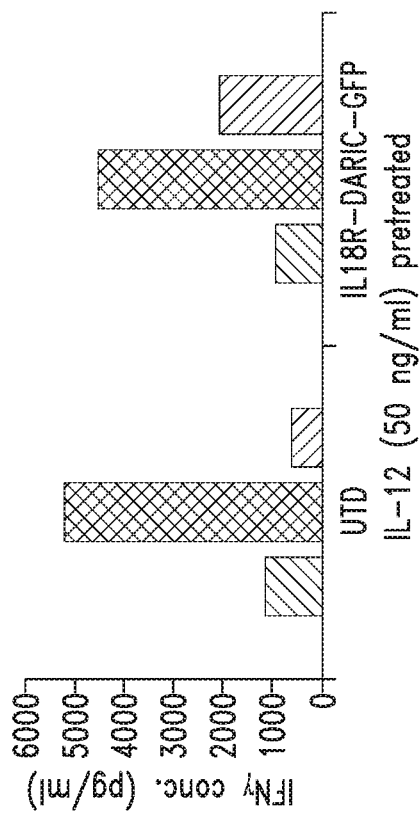
Figure 2:
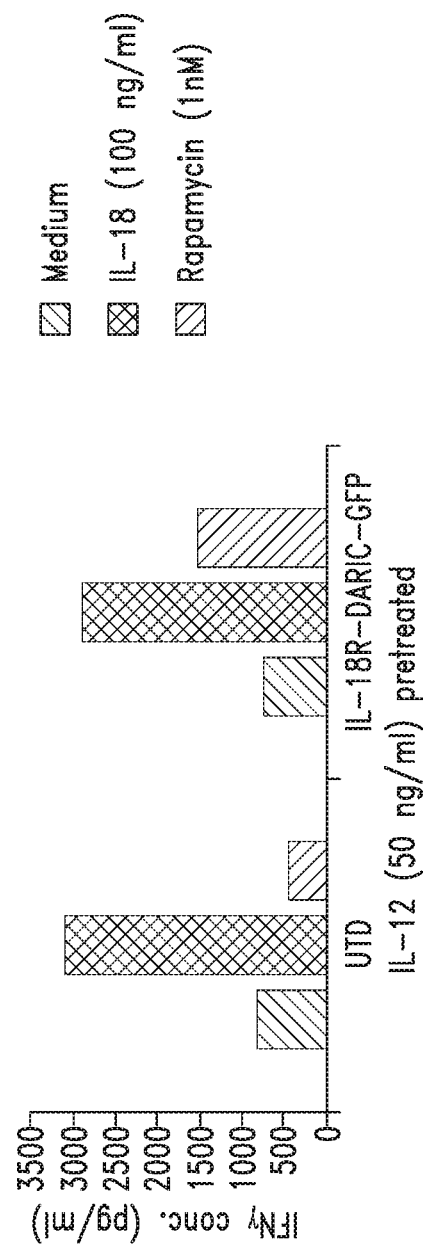

Donor PBMCs were transduced with LVV encoding IL-18R-DARIC-GFP. Transduced PBMCs and untransduced control PBMCs were pre-treated with 50 ng/mL human recombinant IL-12 for 24 hours. The treated cells were washed and cultured in medium only, medium with 100 ng/mL human recombinant IL-18 or medium with 1 nM rapamycin. T cells cultured in IL-18 showed increased IFNγ production in both untransduced controls and cells transduced with IL-18R-DARIC-GFP. In contrast, only cells transduced with IL-18R-DARIC-GFP showed increased IFNγ production when treated with rapamycin. FIG. 2.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A fusion polypeptide comprising:
   (a) a first polypeptide comprising, in the following order:
      (i) a first extracellular multimerization domain;
      (ii) a first transmembrane domain; and
      (iii) an IL-18R1 immune receptor intracellular signaling domain;
   (b) a polypeptide cleavage signal; and
   (c) a second polypeptide comprising, in the following order:
      (i) a second extracellular multimerization domain;
      (ii) a second transmembrane domain; and
      (iii) an IL-18RAP immune receptor intracellular signaling domain;
   wherein the first extracellular multimerization domain comprises an FKBP12-rapamycin binding (FRB) polypeptide and the second extracellular multimerization domain comprises an FK506 binding protein (FKBP12) polypeptide; or
   wherein the first extracellular multimerization domain comprises an FKBP12 polypeptide and the second extracellular multimerization domain comprises an FRB polypeptide; and
   wherein the fusion polypeptide has a sequence having at least 95% identity to SEQ ID NO: 5.

2. The fusion polypeptide of claim 1, wherein the first multimerization domain and the second multimerization domain associate with a bridging factor, wherein the bridging factor is rapamycin or a rapalog thereof.

3. The fusion polypeptide of claim 1, wherein the FRB polypeptide is FRB T2098L or FRB T89L.

4. The fusion polypeptide of claim 1, wherein:
   a) the first transmembrane domain and the second transmembrane domain are independently selected from the group consisting of: a CD4 transmembrane domain, a CD8α transmembrane domain, an amnionless (AMN) transmembrane domain, a CD28 transmembrane domain, a CD154 transmembrane domain, and a CD71 transmembrane domain; or
   b) the first transmembrane domain and the second transmembrane domain are independently selected from the group consisting of: a CD4 transmembrane domain and a CD8α transmembrane domain.

5. The fusion polypeptide of claim 1, wherein the polypeptide cleavage signal is a viral self-cleaving polypeptide selected from the group consisting of: a foot-and-mouth disease virus (FMDV) (F2A) peptide, an equine rhinitis A virus (ERAV) (E2A) peptide, a *Thosea asigna* virus (TaV) (T2A) peptide, a porcine teschovirus-1 (PTV-1) (P2A) peptide, a Theilovirus 2A peptide, and an encephalomyocarditis virus 2A peptide.

6. The fusion polypeptide of claim 1, wherein the first multimerization domain localizes extracellularly when the first polypeptide is expressed and the second multimerization domain localizes extracellularly when the second polypeptide is expressed.

7. A fusion polypeptide comprising the amino acid sequence of SEQ ID NO: 5.

* * * * *